United States Patent [19]

Stein et al.

[11] Patent Number: 5,414,132
[45] Date of Patent: May 9, 1995

[54] 1-ALKYL-2-HYDROXY-2-TRI-FLUOROMETHYL ETHYLAMINES

[75] Inventors: Mark M. Stein, Wilmington, Del.; Diane A. Trainor, Glen Mills, Pa.

[73] Assignee: Zeneca Inc., Wilmington, Del.

[21] Appl. No.: 940,932

[22] Filed: Sep. 4, 1992

Related U.S. Application Data

[60] Division of Ser. No. 491,757, Mar. 9, 1990, Pat. No. 5,194,588, which is a division of Ser. No. 5,538, Jan. 20, 1987, Pat. No. 4,910,190, which is a continuation-in-part of Ser. No. 821,150, Jan. 21, 1986, abandoned.

[30] Foreign Application Priority Data

| Jan. 22, 1985 | [GB] | United Kingdom | 01522 |
| Jan. 22, 1985 | [GB] | United Kingdom | 01523 |
| Jan. 22, 1985 | [GB] | United Kingdom | 01524 |

[51] Int. Cl.$^6$ .................................................. C07C 215/08
[52] U.S. Cl. .................................................. 564/503
[58] Field of Search ..................................... 564/503

[56] References Cited

U.S. PATENT DOCUMENTS

| 4,596,789 | 6/1986 | Dutta et al. | 514/18 |
| 5,166,154 | 11/1992 | Skiles et al. | 514/249 |
| 5,221,665 | 6/1993 | Skiles et al. | 514/18 |
| 5,232,928 | 8/1993 | Skiles et al. | 514/291 |

FOREIGN PATENT DOCUMENTS

| 0195212 | 9/1986 | European Pat. Off. |
| 2171103 | 8/1986 | United Kingdom |

OTHER PUBLICATIONS

Imperiali, B. & Abeles, R. H. *Biochemistry* (1986), 25, 3760.
Imperiali, B. & Ableles, R. H. *Tetrahedron Lett.* (1986), 27, 135.
Kingsbury, C. A., et al. *J. Chem. Soc. Perkin Trans. II* (1982), 867.
McBee, E. T., et al. *J. Amer. Chem. Soc.* (1956) 78, 4053.
Cook, D. J., et al, *J. Amer. Chem. Soc.* (1954), 76, 83.

*Primary Examiner*—Richard L. Raymond
*Attorney, Agent, or Firm*—Cushman Darby & Cushman

[57] ABSTRACT

The invention concerns pharmaceutically useful trifluoromethyl ketone substituted di-, tri- and tetra-peptide derivatives of the formulae Ia, Ib, Ic set out hereinafter, and salts thereof, which are inhibitors of human leukocyte elastase. Also described herein are pharmaceutical compositions containing a peptide derivative and processes and intermediates for use in the manufacture of the peptide derivatives.

2 Claims, No Drawings

1-ALKYL-2-HYDROXY-2-TRIFLUOROMETHYL ETHYLAMINES

This application is a divisional application of application Ser. No. 07/491,757, filed on Mar. 9, 1990, and now U.S. Pat. No. 5,194,588, which was a divisional application of Ser. No. 07/005,538, filed on Jan. 20, 1987, and now U.S. Pat. No. 4,910,190, which was itself a continuation-in-part of application 06/821,150, filed on Jan. 21, 1986, and now abandoned.

The present invention relates to certain trifluoromethyl ketone substituted peptide derivatives which are human leukocyte elastase (HLE) inhibitors making them useful whenever such inhibition is desired such as for research tools in pharmacological, diagnostic and related studies and in the treatment of tissue degenerative diseases such as pulmonary emphysema, atherosclerosis, rheumatoid arthritis and osteo arthritis in warm blooded animals. The invention also includes intermediates useful in the synthesis of these peptide derivatives, processes for preparing them, pharmaceutical compositions containing such peptide derivatives and methods for their use.

The substituted peptides of the present invention may be represented by the formulae Ia, Ib and Ic (set out hereinbelow proceeding the Examples with other formulae denoted by Roman numerals) wherein $R^1$ is alkyl;

$R^2$ and $R^5$ are alkyl, substituted alkyl, aryl, aralkyl, substituted aralkyl or substituted aryl;

$R^3$ is alkyl, substituted alkyl, cycloalkyl, substituted cycloalkyl, alkenyl, substituted alkenyl, aryl, substituted aryl, aralkyl, substituted aralkyl, an aliphatic heterocycle, substituted aliphatic heterocycle, an aromatic heterocycle or a substituted aromatic heterocycle;

$R^4$ and $R^6$ are hydrogen or methyl;

A is selected from the group consisting of

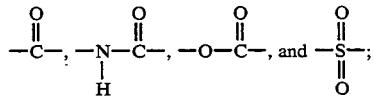

and
n is 0, 1 or 2;
and, where appropriate, the acid- and base-addition salts thereof.

Compounds of formulae Ia, Ib and Ic are referred to herein as dipeptides, tripeptides and tetrapeptides, respectively.

The compounds of the invention include those wherein $R^1$ is an alkyl group containing from 1 to 5 carbon atoms, and more preferably from 2 to 5 carbons;

$R^2$ and $R^5$ are each selected independently from the group consisting of:
(I) an alkyl group containing from 1 to 10 carbons;
(II) an alkyl group containing from 1 to 6 carbon atoms substituted by at least one member selected from the group consisting of:
(a) hydroxy;
(b) amino;
(c) alkylamino containing from 1 to 6 carbons;
(d) dialkylamino wherein each alkyl group contains from 1 to 6 carbons;
(e) alkanoyl containing from 1 to 6 carbons;
(f) arylcarbonyl wherein the aryl contains 6, 10 or 12 carbons;
(g) aralkanoyl containing 8 to 13 carbons;
(h) amido which may be attached to the alkyl group via either a nitrogen or carbon of said amido;
(i) alkylcarbonylamino wherein the alkyl group contains from 1 to 6 carbons;
(j) alkylaminocarbonyl wherein the alkyl group contains from 1 to 6 carbons;
(k) arylcarbonylamino wherein the aryl group contains 6, 10 or 12 carbons;
(l) aralkylcarbonylamino wherein the aralkyl group contains from 7 to 13 carbons;
(m) arylaminocarbonyl wherein the aryl group contains 6, 10 or 12 carbons;
(n) aralkylaminocarbonyl wherein the aralkyl group contains from 7 to 13 carbons;
(o) carboxy;
(p) aryloxycarbonyl wherein the aryl group contains 6, 10 or 12 carbons;
(q) aralkoxycarbonyl wherein the aralkoxy group contains from 7 to 13 carbons;
(r) alkanoyloxy containing from 1 to 6 carbons;
(s) aroyloxy wherein the aryl portion contains 6, 10 or 12 carbons;
(t) aralkanoyloxy containing from 8 to 14 carbons;
(u) alkylsulfonamido wherein the alkyl group contains from 1 to 6 carbons;
(v) aralkylsulfonamido wherein the aralkyl group contains from 7 to 13 carbons;
(w) arylsulfonamido wherein the aryl group contains 6, 10 or 12 carbons;
(x) acylsulfonamido (i.e., acylaminosulfonyl and sulfonylaminocarbonyl) (1 to 15 carbons) including acylsulfonamido wherein the acyl group contains 1 to 7 carbons when it is the terminal portion of the acylsulfonamide and provided that when the acylsulfonamido contains an aryl the aryl may be further substituted by a member selected from fluoro, chloro, bromo, iodo and nitro;
(y) alkoxycarbonyl wherein the alkoxy group contains from 1 to 6 carbons;
(z) aralkoxycarbonylamino containing from 8 to 13 carbons (e.g., benzyloxycarbonyl amino);
(aa) aryloxycarbonylamino wherein the aryloxy group contains 6, 10 or 12 carbons;
(bb) alkoxycarbonylamino wherein the alkyloxy group contains from 1 to 6 carbons;
(cc) aryl containing 6, 10 or 12 carbons (e.g., phenyl, biphenyl, naphthyl);
(dd) aryl containing 6, 10 or 12 carbons and substituted by 1 to 3 members selected from the group consisting of chloro, bromo, iodo, fluoro, trifluoromethyl, hydroxy, alkyl (1 to 6 carbons), alkoxy (1 to 6 carbons), alkoxycarbonyl (1 to 6 carbons), carboxy, 5-tetrazolo, and acylsufonamido (i.e. acylaminosulfonyl and sulfonylaminocarbonyl) (1 to 15 carbons) and provided that when the acylsulfonamido contains an aryl the aryl may be further substituted by a member selected from fluoro, chloro, bromo, iodo and nitro;
(ee) cycloalkyl containing from 3 to 15 carbons (e.g., cyclohexyl, adamantyl, norbornyl);
(ff) alkylureido wherein the alkyl group contains from 1 to 6 carbons;
(gg) aralkylureido containing from 8 to 13 carbons;

(hh) arylureido wherein the aryl group contains 6, 10 or 12 carbons; and (III) an aryl group of 6 carbons, e.g. phenyl;

R³ is selected from the group consisting of:

(I) an alkyl group containing from 1 to 12 carbons;

(II) an alkyl group containing from 1 to 12 carbons and from 1 to 4 hetero atoms each of which is selected independently from the group consisting of nitrogen and oxygen;

(III) an alkyl group containing from 1 to 12 carbons and, optionally, 1 to 4 hetero atoms each of which is selected independently from the group consisting of nitrogen and oxygen, and substituted on at least one of carbon or nitrogen by 1 to 3 members selected independently from the group consisting of:

For carbon:

(a) hydroxy, provided that it may not be on a carbon directly bonded to A;

(b) amino, provided that it may not be on a carbon directly bonded to A;

(c) alkylamino containing from 1 to 6 carbons, provided that it may not be on a carbon directly bonded to A;

(d) dialkylamino wherein each alkyl group contains from 1 to 6 carbons, provided that it may not be on a carbon directly bonded to A;

(e) alkanoyl containing from 1 to 6 carbons;

(f) arylcarbonyl wherein the aryl contains 6, 10 or 12 carbons;

(g) aralkanoyl containing 8 to 13 carbons;

(h) amido which may be attached to the alkyl group via either a nitrogen or carbon of said amido;

(i) alkylcarbonylamino wherein the alkyl group contains from 1 to 6 carbons;

(j) alkylaminocarbonyl wherein the alkyl group contains from 1 to 6 carbons;

(k) arylcarbonylamino wherein the aryl group contains 6, 10 or 12 carbons;

(k)-(1) arylcarbonylamino wherein the aryl group contains 6, 10 or 12 carbons and is substituted by a member selected from carboxy, alkoxycarbonyl, where alkoxy is 1 to 3 carbons, 5-tetrazolo, and acylsulfonamido (i.e. acylaminosulfonyl and sulfonylaminocarbonyl) containing 1 to 15 carbons and provided that when the acylsulfonamido contains an aryl the aryl may be further substituted by a member selected from fluoro, chloro, bromo, iodo and nitro;

(l) aralkylcarbonylamino wherein the aralkyl group contains from 7 to 13 carbons;

(l)-(1) aralkylcarbonylamino wherein the aralkyl group contains 7 to 13 carbons and is substituted on the aryl portion by a member selected from carboxy, alkoxycarbonyl, where the alkoxy has 1 to 3 carbons, 5-tetrazolo, and acylsulfonamido (i.e., acylaminosulfonyl and sulfonylaminocarbonyl) containing 1 to 15 carbons and provided that when the acylsulfonamido contains an aryl the aryl may be further substituted by a member selected from fluoro, chloro, bromo, iodo and nitro;

(m) arylaminocarbonyl wherein the aryl group contains 6, 10 or 12 carbons;

(n) aralkylaminocarbonyl wherein the aralkyl group contains from 7 to 13 carbons;

(o) carboxy;

(p) aryloxycarbonyl wherein the aryl group contains 6, 10 or 12 carbons;

(q) aralkoxycarbonyl wherein the aralkoxy group contains from 7 to 13 carbons;

(r) alkanoyloxy containing from 1 to 6 carbons;

(s) aroyloxy wherein the aryl portion contains 6, 10 or 12 carbons;

(t) aralkanoyloxy containing from 8 to 13 carbons;

(u) alkylsulfonamido wherein the alkyl group contains from 1 to 6 carbons;

(u)-(1) cycloalkylsulfonamido wherein the cycloalkyl portion contains 3 to 15 carbons (e.g., cyclohexyl, adamantyl, norbornyl);

(v) aralkylsulfonamido wherein the aralkyl group contains from 7 to 13 carbons;

(w) arylsulfonamido wherein the aryl group contains 6, 10 or 12 carbons;

(x) acylsulfonamido (i.e., acylaminosulfonyl and sulfonylaminocarbonyl) (1 to 15 carbons) including acylsulfonamido wherein the acyl group contains 1 to 7 carbons when it is the terminal portion of the acylsulfonamide, and provided that when the acylsulfonamido contains an aryl the aryl may be further substituted by a member selected from fluoro, chloro, bromo, iodo and nitro;

(y) alkoxycarbonyl wherein the alkoxy group contains from 1 to 6 carbons;

(z) aralkoxycarbonylamino containing from 8 to 13 carbons (e.g., benzyloxycarbonylamino);

(z)-(1) aralkylaminocarbonyloxy containing 8 to 13 carbons;

(z)-(2) aryloxy wherein the aryl contains 6, 10 or 12 carbons;

(z)-(3) aryloxy wherein the aryl contains, 6, 10 or 12 carbons and is substituted by a member selected from aminocarbonyl, aminocarbonylalkyl where the alkyl has 1 to 3 carbons, alkoxy carbonyl having 2 to 4 carbons, and carboxy;

(aa) aryloxycarbonylamino wherein the aryloxy group contains 6, 10 or 12 carbons;

(aa)-(1) arylaminocarbonyloxy wherein the aryl group contains 6, 10 or 12 carbons;

(bb) alkoxycarbonylamino wherein the alkyloxy group contains from 1 to 6 carbons;

(bb)-(1) alkoxycarbonylamino wherein the alkoxy group contains 1 to 6 carbons and is optionally bonded on carbon to a carbon of an aromatic heterocyclic group as described in (gg) under R³;

(bb)-(2) alkoxycarbonylamino wherein the alkoxy group contains 1 to 6 carbons substituted by an aliphatic heterocyclic group as described in (ff) under R³;

(bb)-(3) aryloxyalkylcarbonyl amino wherein the aryl contains 6 or 10 carbons and the alkyl has 1 to 6 carbons;

(bb)-(4) alkylaminocarbonyloxy wherein the alkyl group contains 1 to 6 carbons;

(cc) aryl containing 6, 10 or 12 carbons (e.g., phenyl, naphthyl, biphenyl);

(cc)-(1) aryloxy containing 6, 10 or 12 carbons;

(dd) aryl containing 6, 10 or 12 carbons and substituted by 1 to 3 members independently selected from the group consisting of chloro, bromo, iodo, fluoro, hydroxy, trifluoromethyl, alkyl (1 to 6 carbons), alkoxy (1 to 6 carbons), alkoxycarbonyl (2 to 6 carbons), carboxy, aminocarbonylalkyl (2 to 6 carbons), aminocarbonyl, 5-tetrazolo, and acylsulfonamido (i.e., acylaminosulfonyl and sulfonylaminocarbonyl) (1 to 15 carbons), and provided that when the acylsulfonamido contains an aryl the aryl may be further substituted by a member selected from fluoro, chloro, bromo, iodo and nitro;

(dd)-(1) aryloxy containing 6, 10 or 12 carbons and substituted on carbon by 1 to 3 members independently selected from the group consisting of chloro, bromo, iodo, fluoro, hydroxy, trifluoromethyl, alkyl (1 to 6 carbons), alkoxy (1 to 6 carbons), alkoxycarbonyl (2 to 6 carbons), carboxy, aminocarbonylalkyl (2 to 6 carbons), aminocarbonyl, 5-tetrazolo, acylsulfonamido (i.e., acylaminosulfonyl and sulfonylaminocarbonyl) (1 to 15 carbons) and provided that when the acylsulfonamido contains an aryl the aryl may be further substituted by a member selected from fluoro, chloro, bromo, iodo and nitro;

(ee) cycloalkyl containing from 3 to 15 carbons (e.g., cyclohexyl, adamantyl, norbornyl);

(ee)-(1) cycloalkyloxy containing from 3 to 15 carbons;

(ff) an aliphatic heterocyclic group of at least 4 atoms containing from 1 to 5 carbons and from 1 to 4 hetero atoms each of which is selected independently from the group consisting of nitrogen and oxygen (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 1 to 6 carbons, an aryloxycarbonyl group wherein the aryl group contains 6, 10 or 12 carbon atoms, an aralkyloxycarbonyl group wherein the aralkyl group contains from 7 to 13 carbons or an alkoxycarbonyl group wherein the alkyl group contains from 1 to 6 carbons;

(ff)-(1) an aliphatic heterocyclic oxy group wherein the oxy link the is bonded directly to a carbon atom of the aliphatic heterocyclic group of at least 5 atoms containing from 1 to 5 carbons and from 1 to 4 hetero atoms each of which is selected independently from the group consisting of nitrogen and oxygen, (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 1 to 6 carbons, an aryloxycarbonyl group wherein the aryl group contains 6, 10 or 12 carbons, an aralkyloxycarbonyl group wherein the aralkyl group contains from 7 to 13 carbons or an alkoxycarbonyl group wherein the alkyl group contains from 1 to 6 carbons;

(gg) an aromatic heterocyclic group of from 1 to 15 carbons and from 1 to 4 heteroatoms each of which is selected independently from the group consisting of sulfur, nitrogen and oxygen and which form 1 to 3 five or six-membered rings at least one of which is aromatic, and optionally, wherein up to 3 carbons of the aromatic ring(s) may be substituted with a member of the group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, aminocarbonylalkyl (2 to 6 carbons) and aminocarbonyl, and provided further that any nitrogen atom may be substituted by an alkyl group containing from 1 to 6 carbon atoms;

(gg)-(1) an aromatic heterocyclic oxy group wherein the oxy link is bonded directly to a carbon of an aromatic heterocyclic group of from 1 to 15 carbons and from 1 to 4 heteroatoms each of which is selected independently from the group consisting of sulfur, nitrogen and oxygen and which form 1 to 3 five or six-membered rings at least one of which is aromatic, and optionally, wherein up to 3 carbons of the aromatic ring(s) may be substituted with a member of the group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, aminocarbonylalkyl (2 to 6 carbons) and aminocarbonyl, and provided further that any nitrogen atom may be substituted by an alkyl group containing from 1 to 6 carbons;

(hh) alkylureido wherein the alkyl group contains from 1 to 6 carbon atoms;

(hh)-(1) cycloalkylureido wherein the cycloalkyl group contains 3 to 15 carbons;

(ii) aralkylureido wherein the aralkyl group contains from 7 to 13 carbons;

(jj) arylureido wherein the aryl group contains 6, 10 or 12 carbons;

(jj)-(1) arylureido wherein the aryl group contains 6, 10 or 12 carbons and is substituted by 1 to 3 members selected independently from the group consisting of chloro, bromo, iodo, fluoro, hydroxy, trifluoromethyl, alkyl (1 to 6 carbons), alkoxy (1 to 6 carbons), alkoxycarbonyl (2 to 6 carbons), carboxy, aminocarbonylalkyl (2 to 6 carbons), aminocarbonyl, 5-tetrazolo, and acylsulfonamido (i.e., acylaminosulfonyl and sulfonylaminocarbonyl) (1 to 15 carbons) including acylsulfonamido wherein the acyl group contains 1 to 7 carbons when it is the terminal portion of the acylsulfonamide and provided that when the acylsulfonamido contains an aryl the aryl may be further substituted by a member selected from fluoro, chloro, bromo, iodo and nitro;

For nitrogen:
(a) alkyl of 1 to 3 carbons;
(b) alkanoyl containing from 2 to 6 carbon atoms;
(c) arylcarbonyl wherein the aryl contains 6, 10 or 12 carbons;
(d) aralkanoyl containing 8 to 14 carbons;
(e) formyl;
(f) an aliphatic heterocyclic group wherein the amino link is bonded directly to a carbon of an aliphatic heterocyclic group defined in (ff) for the carbon substituents;
(g) an aromatic heterocyclic group wherein the amino link is bonded directly to a carbon of the aromatic heterocyclic group defined in (gg) for the carbon substituents;
(IV) an aryl group containing 6, 10 or 12 carbons;
(V) an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, alkoxycarbonyl containing from 2 to 6 carbons, carboxy, alkylcarbonylamino wherein the alkyl group contains 1 to 6 carbons, 5-tetrazolo, and acylsulfonamido (i.e., acylaminosulfonyl and sulfonylaminocarbonyl) containing from 1 to 15 carbons, and provided that when the acylsulfonamido contains an aryl the aryl may be further substituted by a member selected from fluoro, chloro, bromo, iodo and nitro;

(VI) a cycloalkyl group containing from 3 to 15 carbons (e.g., cyclohexyl, adamantyl, norbornyl);

(VI)-(1) a cycloalkyl group containing from 3 to 15 carbons (e.g., cyclohexyl, adamantyl, norbornyl), substituted by a member selected from the group consisting of carboxy and alkoxycarbonyl wherein the alkoxy group contains 1 to 4 carbons;

(VII) an aliphatic heterocyclic group of at least 5 atoms containing from 1 to 5 carbons and from 1 to 4 hetero atoms each of which is selected independently from the group consisting of nitrogen and oxygen, (e.g., morpholine, piperazine) which may be substituted at any nitrogen with a member selected from the group consisting of an alkyl group containing from 1 to 6 carbon atoms, an alkanoyl group containing from 1 to 6 carbons, an aryloxycarbonyl group wherein the aryl group contains 6, 10 or 12 carbons, an aralkoxycarbonyl group wherein the aralkyl group contains from 7 to 13 carbons and an alkoxycarbonyl group containing from 2 to 7 carbons, provided that when A is OCO or NHCO then A must be bonded to a carbon atom of the aliphatic heterocyclic group;

(VIII) an aromatic heterocyclic group of from 1 to 15 carbons and from 1 to 4 heteroatoms each of which is selected independently from the group consisting of sulfur, nitrogen and oxygen, and which form 1 to 3 five or six-membered rings at least one of which is aromatic, and optionally, wherein up to 3 carbons of the aromatic ring(s) may be substituted at any carbon atom with a member of the group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, and provided further that any nitrogen may be substituted by an alkyl group containing from 1 to 6 carbons, provided that when A is OCO or NHCO then A must be bonded to a carbon of the aromatic heterocycle;

(IX) an alkenyl group of 2 to 10 carbons, having at least one double bond; and (X) an alkenyl group of 2 to 10 carbons, having at least one double bond and substituted by a member selected from the group consisting of
 (a) aryl of 6 or 10 carbons;
 (b) aryl of 6 or 10 carbons substituted by 1 to 3 members selected independently from the group consisting of chloro, bromo, iodo, fluoro, hydroxy, trifluoromethyl, alkyl (1 to 6 carbons), alkoxy (1 to 6 carbons), alkoxycarbonyl (2 to 6 carbons), carboxy, 5-tetrazolo, and acylsulfonamido (i.e., acylaminosulfonyl and sulfonylaminocarbonyl) (1 to 15 carbons) and provided that when the acylsulfonamido contains an aryl the aryl may be further substituted by a member selected from fluoro, chloro, bromo, iodo and nitro; and
 (c) ureidocarbonyl;

$R^4$ and $R^6$ are each independently selected from hydrogen or methyl;

n is 0, 1 or 2; and

A is selected from the group consisting of

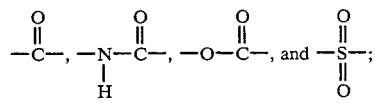

and where appropriate, the acid- and base-addition salts thereof.

Particular values for compounds of the invention include the following members of the groups defined above:

$R^1$ is an alkyl group containing 3 carbons;

$R^2$ and $R^5$ are each selected independently from the group consisting of:
 (I) an alkyl group containing from 1 to 4 carbons;
 (II) an alkyl group containing from 1 to 4 carbons substituted by at least one member selected from the group consisting of:
  (e) alkanoyl containing from 1 to 3 carbons;
  (f) arylcarbonyl wherein the aryl contains 6 or 10 carbons (e.g., phenyl or naphthyl);
  (g) aralkanoyl containing 8 carbons (e.g., phenylacetyl);
  (h) amido which may be attached to the alkyl group via either a nitrogen or carbon of said amido;
  (i) alkylcarbonylamino wherein the alkyl group contains from 1 to 2 carbons;
  (j) alkylaminocarbonyl wherein the alkyl group contains from 1 to 2 carbons;
  (k) arylcarbonylamino wherein the aryl group contains 6 carbons (e.g., phenyl);
  (l) aralkylcarbonylamino wherein the aralkyl group contains 7 carbons;
  (m) arylaminocarbonyl wherein the aryl group contains 6 carbons;
  (n) aralkyaminocarbonyl wherein the aralkyl group contains 7 carbons;
  (o) carboxy;
  (p) aryloxycarbonyl wherein the aryl group contains 6 carbons;
  (q) aralkoxycarbonyl wherein the aralkoxy group contains 7 carbons;
  (r) alkanoyloxy containing from 1 to 2 carbons;
  (s) aroyloxy wherein the aryl portion contains 6 carbons;
  (t) aralkanoyloxy containing 8 carbons;
  (u) alkylsulfonamido wherein the alkyl group contains from 1 to 6 carbons;
  (v) aralkylsulfonamido wherein the aralkyl group contains from 7 to 13 carbons (e.g., 1-naphthylmethylsulfonylamino or 4-phenylbutylsulfonylamino);
  (w) arylsulfonamido wherein the aryl group contains 6 or 10 carbons;
  (x) acylsulfonamido containing 1 to 15 carbons (e.g. phenylsulfonylaminocarbonyl);
  (y) alkoxycarbonyl wherein the alkoxy group contains from 1 to 2 carbons;
  (z) aralkoxycarbonylamino wherein the aralkoxy group contains 7 carbons (e.g., benzyloxycarbonylamino);

(aa) aryloxycarbonylamino wherein the aryloxy group contains 6 carbons;
(bb) alkoxycarbonylamino wherein the alkyloxy group contains from 1 to 3 carbons;
(cc) aryl containing 6 or 10 carbons (e.g., phenyl or naphthyl);
(dd) aryl containing 6 or 10 carbons and substituted by 1 to 3 members selected from the group consisting of chloro, bromo, iodo, fluoro, trifluoromethyl, hydroxy, alkyl (1 to 2 carbons), alkoxy (1 to 2 carbons), alkoxycarbonyl (2 to 3 carbons), carboxy, 5-tetrazolo and acylsufonamido (1 to 15 carbons);
(ee) cycloalkyl containing from 3 to 15 carbons (e.g., cyclohexyl, adamantyl, norbornyl).
(ff) alkylureido wherein the alkyl group contains from 1 to 2 carbons;
(gg) aralkylureido wherein the aralkyl group contains 7 carbons;
(hh) arylureido wherein the aryl group contains 6 or 10 carbons; and
(III) an aryl group of 6 carbons;

$R^3$ is selected from the group consisting of:
(I) an alkyl group containing from 1 to 12 carbons;
(II) an alkyl group containing from 1 to 12 carbons and from 1 to 4 hetero atoms each of which is selected independently from the group consisting of nitrogen and oxygen;
(III) an alkyl group containing from 1 to 12 carbons and, optionally, 1 to 4 hetero atoms each of which is selected independently from the group consisting of nitrogen and oxygen, and substituted on at least one of carbon or nitrogen by 1 to 3 members selected independently from the group consisting of:

For carbon:
(e) alkanoyl containing from 1 to 6 carbons;
(f) arylcarbonyl wherein the aryl contains 6, 10 or 12 carbons;
(g) aralkanoyl containing 8 to 13 carbons;
(h) amido which may be attached to the alkyl group via either a nitrogen or carbon of said amido;
(i) alkylcarbonylamino wherein the alkyl group contains from 1 to 6 carbons;
(j) alkylaminocarbonyl wherein the alkyl group contains from 1 to 6 carbons;
(k) arylcarbonylamino wherein the aryl group contains 6 or 10 carbons;
(k)-(1) arylcarbonylamino wherein the aryl group contains 6 or 10 carbons and is substituted by a member selected from carboxy, alkoxycarbonyl, where alkoxy is 1 to 3 carbons, 5-tetrazolo, and acylsulfonamido containing 1 to 15 carbons;
(l) aralkylcarbonylamino wherein the aralkyl group contains from 7 to 13 carbons;
(l)-(1) aralkylcarbonylamino wherein the aralkyl group contains 7 to 13 carbons and is substituted on the aryl portion by a member selected from carboxy, alkoxycarbonyl, where the alkoxy has 1 to 3 carbons, 5-tetrazolo, and acylsulfonamido containing 1 to 15 carbons;
(m) arylaminocarbonyl wherein the aryl group contains 6 or 10 carbons;
(n) aralkylaminocarbonyl wherein the aralkyl group contains from 7 to 13 carbons;
(o) carboxy;
(p) aryloxycarbonyl wherein the aryl group contains 6 or 10 carbons;
(q) aralkoxycarbonyl wherein the aralkoxy group contains from 7 to 13 carbons;
(r) alkanoyloxy containing from 2 to 3 carbons;
(s) aroyloxy wherein the aryl portion contains 6 or 10 carbons;
(t) aralkanoyloxy containing from 8 to 13 carbons;
(u) alkylsulfonamido wherein the alkyl group contains from 1 to 6 carbons;
(u)-(1) cycloalkylsulfonamido wherein the cycloalkyl portion contains 3 to 15 carbons (e.g., the cycloalkyl may be cyclohexyl, adamantyl, norbornyl), e.g., 1-adamantylsulfonylamino;
(v) aralkylsulfonamido wherein the aralkyl group contains from 7 to 13 carbons;
(w) arylsulfonamido wherein the aryl group contains 6 or 10 carbons;
(x) acylsulfonamido containing 1 to 15 carbons;
(y) alkoxycarbonyl wherein the alkoxy group contains from 1 to 3 carbons;
(z) aralkoxycarbonylamino containing from 8 to 13 carbons (e.g., benzyloxycarbonylamino);
(z)-(1) aralkylaminocarbonyloxy wherein the aralkyl group contains 7 to 13 carbons;
(z)-(2) aryloxy wherein the aryl contains 6, 10 or 12 carbons;
(z)-(3) aryloxy wherein the aryl contains 6, 10 or 12 carbons and is substituted by a member selected from aminocarbonyl, aminocarbonylalkyl where the alkyl has 1 to 3 carbons, alkoxycarbonyl having 2 to 4 carbons, and carboxy;
(aa) aryloxycarbonylamino wherein the aryloxy group contains 6 or 10 carbons;
(aa)-(1) arylaminocarbonyloxy wherein the aryl group contains 6 or 10 carbons;
(bb) alkoxycarbonylamino wherein the alkyloxy group contains from 1 to 6 carbons;
(bb)-(1) alkoxycarbonylamino wherein the alkoxy group contains 1 to 6 carbons and is optionally bonded to a carbon of an aromatic heterocyclic group as described in (gg) under $R^3$;
(bb)-(2) alkoxycarbonylamino wherein the alkoxy group contains 1 to 6 carbons substituted by an aliphatic heterocyclic group as described in (ff) under $R^3$;
(bb)-(3) aryloxyalkylcarbonylamino wherein the aryl contains 6 or 10 carbons and the alkyl has 1 to 6 carbons;
(bb)-(4) alkylaminocarbonyloxy wherein the alkyl group contains 1 to 6 carbons;
(cc) aryl containing 6 or 10 carbons (e.g., phenyl or naphthyl);
(cc)-(1) aryloxy containing 6 or 10 carbons;
(dd) aryl containing 6, 10 or 12 carbons and substituted by 1 to 3 members independently selected from the group consisting of chloro, bromo, iodo, fluoro, hydroxy, trifluoromethyl, alkyl (1 to 6 carbons), alkoxy (1 to 6 carbons), alkoxycarbonyl (2 to 6 carbons), carboxy, aminocarbonylalkyl (2 to 6 carbons), aminocarbonyl, 5-tetrazolo, and acylsulfonamido (1 to 15 carbons);
(dd)-(1) aryloxy containing 6, 10 or 12 carbons and substituted by 1 to 3 members independently selected from the group consisting of chloro, bromo, iodo, fluoro, hydroxy, trifluoromethyl, alkyl (1 to 6 carbons), alkoxy (1 to 6 carbons), alkoxycarbonyl (2 to 6 carbons), carboxy, acylsulfonamido (1 to 15 carbons), aminocarbonylalkyl (2 to 6 carbons), aminocarbonyl and 5-tetrazolo;

(ee) cycloalkyl containing from 3 to 15 carbons (e.g., cyclohexyl, adamantyl or norbornyl);

(ee)-(1) cycloalkyloxy containing from 3 to 15 carbons;

(ff) an aliphatic heterocyclic group of at least 5 atoms containing from 1 to 5 carbons and from 1 to 4 hetero atoms each of which is selected independently from the group consisting of nitrogen and oxygen (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 2 to 6 carbons, an aryloxycarbonyl group wherein the aryl group contains 6, 10 or 12 carbons, an aralkyloxycarbonyl group wherein the aralkyl group contains from 7 to 13 carbons or an alkoxycarbonyl group wherein the alkyl group contains from 1 to 6 carbons;

(ff)-(1) an aliphatic heterocyclic oxy group wherein the oxy link is bonded directly to a carbon of an aliphatic heterocyclic group of at least 5 atoms containing from 1 to 5 carbons and from 1 to 4 hetero atoms each of which is selected independently from the group consisting of nitrogen and oxygen, wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 2 to 6 carbons, an aryloxycarbonyl group wherein the aryl group contains 6, 10 or 12 carbons, an aralkyloxycarbonyl group wherein the aralkyl group contains from 7 to 13 carbons or an alkoxycarbonyl group wherein the alkyl group contains from 1 to 6 carbons (e.g., morpholine, piperazine);

(gg) an aromatic heterocyclic group of from 1 to 15 carbons and from 1 to 4 heteroatoms each of which is selected independently from the group consisting of sulfur, nitrogen and oxygen and which form 1 to 2 five or six-membered rings at least one of which is aromatic, and optionally, wherein up to 3 carbons of the aromatic ring(s) may be substituted with a member of the group consisting of fluoro, chloro, bromo, iodo, trifluoromethyl, alkyl containing methyl, alkoxy containing from 1 to 2 carbons, alkanoyl containing from 2 to 3 carbons, carboxy, aminocarbonylalkyl (2 to 6 carbons) and aminocarbonyl, and provided further that any nitrogen atom may be substituted by an alkyl group containing from 1 to 6 carbons;

(gg)-(1) an aromatic heterocyclic oxy group wherein the oxy link is bonded directly to a carbon atom of an aromatic heterocyclic group of from 1 to 15 carbons and from 1 to 4 heteroatoms each of which is selected independently from the group consisting of sulfur, nitrogen and oxygen and which form 1 to 2 five or six-membered rings at least one of which is aromatic, and optionally, wherein up to 3 carbons of the aromatic ring(s) may be substituted with a member of the group consisting of fluoro, chloro, bromo, iodo, trifluoromethyl, methyl, alkoxy containing from 1 to 2 carbons, alkanoyl containing from 2 to 3 carbons, carboxy, aminocarbonylalkyl (2 to 6 carbons) and aminocarbonyl, and provided further that any nitrogen atom may be substituted by an alkyl group containing from 1 to 6 carbons;

(hh) alkylureido wherein the alkyl group contains from 1 to 6 carbons;

(hh)-(1) cycloalkylureido wherein the cycloalkyl group contains 3 to 15 carbons;

(ii) aralkylureido wherein the aralkyl group contains from 7 to 13 carbons;

(jj) arylureido wherein the aryl group contains 6 or 10 carbons;

(jj)-(1) arylureido wherein the aryl group contains 6 or 10 carbons and is substituted by 1 to 3 members independently selected from the group consisting of chloro, bromo, iodo, fluoro, hydroxy, trifluoromethyl, alkyl (1 to 6 carbons), alkoxy (1 to 6 carbons), alkoxycarbonyl (2 to 6 carbons), carboxy, acylsulfonamido (1 to 15 carbons), aminocarbonylalkyl (2 to 6 carbons), aminocarbonyl and 5-tetrazolo;

For nitrogen:

(a) alkyl of 1 to 3 carbons;

(b) alkanoyl containing from 2 to 6 carbons;

(c) arylcarbonyl wherein the aryl contains 6, 10 or 12 carbons;

(d) aralkanoyl containing 8 to 13 carbons;

(e) formyl;

(f) an aliphatic heterocyclic amino group wherein the amino link is bonded directly to a carbon of an aliphatic heterocyclic group defined in (ff) for the carbon substituents;

(g) an aromatic heterocyclic amino group wherein the amino link is bonded directly to a carbon of the aromatic heterocyclic group defined in (gg) for the carbon substituents;

(IV) an aryl group containing 6 or 10 carbons;

(V) an aryl group containing 6 or 10 carbons suitably substituted by 1 to 3 members selected independently from the group consisting of fluoro, chloro, bromo, iodo, trifluoromethyl, alkyl containing from 1 to 6 carbons, alkoxy containing from 1 to 6 carbons, alkoxycarbonyl containing from 2 to 6 carbons, carboxy, alkylcarbonylamino wherein the alkyl group contains 1 to 6 carbons, 5-tetrazolo, and acylsulfonamido containing from 1 to 15 carbons (e.g., 4-[(4-chlorophenyl)sulfonylaminocarbonyl]phenyl or 4-[(4-bromophenyl)sulfonylaminocarbonyl]phenyl);

(VI) a cycloalkyl group containing from 3 to 15 carbons (e.g., cyclohexyl, adamantyl or norbornyl);

(VI)-(1) a cycloalkyl group containing from 3 to 15 carbons (e.g., cyclohexyl, adamantyl or norbornyl), substituted by a member selected from the group consisting of carbon and alkoxycarbonyl wherein the alkoxy group contains 1 to 4 carbons;

(VII) an aliphatic heterocyclic group of at least 5 atoms containing from 1 to 5 carbons and from 1 to 4 hetero atoms each of which is selected independently from the group consisting of nitrogen and oxygen, (e.g., morpholine, piperazine), which may be substituted at any nitrogen with a member selected from the group consisting of methyl, an alkanoyl group containing from 2 to 6 carbons, an aryloxycarbonyl group wherein the aryl group contains 6 or 10 carbons, an aralkoxycarbonyl group wherein the aralkyl group contains 7 carbons and an alkoxycarbonyl group containing from 2 to 3 carbons, provided that when A is OCO or NHCO, then A must be bonded to a carbon of the aliphatic heterocyclic group;

(VIII) an aromatic heterocyclic group of from 1 to 15 carbons and from 1 to 4 heteroatoms each of which is selected independently from the group consisting of sulfur, nitrogen and oxygen, and which form 1 to 2 five or six-membered rings at least one of which is aromatic, and optionally, wherein up to 3 carbons of the aromatic ring(s) may be substituted at any carbon atom with a member of the group consisting of fluoro, chloro, bromo, iodo, trifluoromethyl, methyl, alkoxy containing from 1 to 2 carbons, alkanoyl containing from 2 to 3 carbons, carboxy, and provided further that any nitrogen may be substituted by an alkyl group containing from 1 to 6 carbons, provided that when A is OCO or NHCO then A must be bonded to a carbon of the aromatic heterocycle;

(IX) an alkenyl group of 2 to 10 carbons, having at least one double bond;

(X) an alkenyl group of 2 to 10 carbons, having at least one double bond and substituted by a member selected from the group consisting of
(a) aryl of 6 or 10 carbons;
(b) aryl of 6 or 10 carbons substituted by 1 to 3 members selected independently from the group consisting of chloro, bromo, iodo, fluoro, hydroxy, trifluoromethyl, alkyl (1 to 6 carbons), alkoxy (1 to 6 carbons), alkoxycarbonyl (2 to 6 carbons), carboxy, acylsulfonamido (1 to 15 carbons) and 5-tetrazolo; and
(c) ureidocarbonyl;

$R^4$ and $R^6$ are each hydrogen;
n=1; and
A is selected from the group consisting of

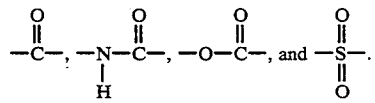

More particular values include:
$R^1$ selected to be isopropyl;
$R^2$ selected from the group consisting of:
(I) an alkyl group containing 2 to 3 carbons;
(II)
  (q) ethyl substituted by aralkoxycarbonyl wherein the aralkoxy group contains 7 carbons;
  (w) butyl substituted by an arylsulfonamido wherein the aryl portion has 6 carbons;
  (x) ethyl substituted by acylsulfonamido containing 7 carbons (e.g., 2-(phenylsulfonylaminocarbonyl)ethyl);
  (z) butyl substituted by aralkyloxycarbonylamino wherein the aralkoxy portion contains 7 carbons, (e.g., benzyloxycarbonylamino);
  (cc) methyl substituted by an aryl containing 6 carbons; and
(III) aryl containing 6 carbons;
$R^3$ selected from the group consisting of:
(I) branched alkyl containing 4 carbons;
(II) an alkyl group containing 5 carbons and 2 oxygens;
(III)
  (k) ethyl substituted by arylcarbonylamino wherein the aryl portion contains 6 carbons;
  (l) ethyl substituted by an aralkylcarbonylamino wherein the aralkyl portion contains 13 carbons;
  (n) ethyl substituted by aralkylaminocarbonyl wherein the alkyl contains 7 carbons;
  (o) an alkyl group containing 2 or 10 carbons and substituted by carboxy;
  (w) an alkyl group containing 5 carbons and substituted by arylsulfonamido wherein the aryl portion contains 6 carbons;
  (x) ethyl substituted by an acylsulfonamido selected from the group consisting of 2-(methylsulfonylaminocarbonyl)ethyl, 2-(phenylsulfonylaminocarbonyl)ethyl, 2-[(1-adamantyl)sulfonylaminocarbonyl]ethyl, and 2-[(1-naphthyl)sulfonylaminocarbonyl]ethyl;
  (y) an alkyl group containing 2 or 10 carbons and substituted by methoxycarbonyl;
  (z) an alkyl group containing 2 to 5 carbons and substituted by aralkoxycarbonyl wherein the aralkoxy portion contains 7 carbons;
  (aa) an alkyl containing 5 carbons and substituted by aryloxycarbonylamino wherein the aryloxy portion contains 6 carbons;
  (bb) ethyl substituted by alkoxycarbonylamino wherein the alkyl group contains 4 carbons; and an alkyl containing 5 carbons and substituted by an alkyloxycarbonylamino wherein the alkoxy group contains 2 carbons and is substituted on the terminal carbon via a direct link to a carbon atom of an aromatic heterocycle containing 5 carbons and 1 nitrogen;
  (bb)-(3) a propyl group substituted by an aryloxyalkylcarbonylamino wherein the aryl group contains 6 carbons and the alkyl group is methyl;
  (cc) methyl or butyl substituted by aryl containing 6 carbons; and a branched alkyl group containing 5 carbons and substituted by 2 aryl groups each containing 6 carbons;
  (dd) a member selected from the group consisting of an alkyl containing 1 or 2 carbons and substituted with an aryl containing 6 carbons wherein the aryl is further substituted by carboxy; methyl substituted by an aryl containing 6 carbons wherein the aryl is further substituted by methoxycarbonyl; ethyl substituted by an aryl containing 6 carbons wherein the aryl is further substituted by ethoxycarbonyl; and ethyl substituted by an aryl containing 6 carbons wherein the aryl is further substituted by an acylsulfonamido containing 7 carbons;
  (ee) ethyl substituted by a cycloalkyl containing 10 carbons, (e.g., 1-adamantylethyl);
  (ff) ethyl substituted by an aliphatic heterocycle containing 4 carbons, 1 nitrogen and 1 oxygen (e.g., 2-(4-morpholinyl)ethyl);
  (gg) an alkyl containing 1 to 2 carbons and substituted by an aromatic heterocycle containing 4 carbons and 1 sulfur (e.g., (2-thiophenyl)methyl or 2-(3-thiophenyl)ethyl); and ethyl substituted by an aromatic heterocycle containing 5 carbons and 1 nitrogen;
  (jj)-(1) an alkyl group containing 5 carbons and substituted by an arylureido wherein the aryl portion contains 6 carbons and wherein the aryl portion is further substituted by ethoxycarbonyl or carboxy;

(zz) propyl substituted by aryloxy wherein the aryl contains 6 carbons; a branched alkyl group containing 5 carbons and substituted by 2 aryloxy groups each containing 6 carbons;

(zzz) methyl or propyl substituted by an aryloxy containing 6 carbons wherein the aryloxy is further substituted by aminocarbonyl; and methyl substituted by an aryloxy containing 6 carbons wherein the aryloxy is further substituted by ethoxycarbonyl;

(IV) an aryl group containing 6 or 10 carbons, e.g., phenyl or naphthyl;

(V) an aryl group containing 6 carbons substituted by a member selected from the group consisting of fluoro, hydroxy, carboxy, methoxy, ethoxy, methoxycarbonyl, ethoxycarbonyl, methylcarbonylamino, an acylsulfonamido containing 2 carbons, (e.g., 4-(methylsulfonaminocarbonyl)phenyl), an acylsulfonamido containing 7 carbons (e.g., 4-(phenylsulfonylaminocarbonyl)phenyl, 4-[(4-chlorophenyl)sulfonylaminocarbonyl]phenyl, or [(4-bromophenyl)sulfonylaminocarbonyl]phenyl), an acylsulfonamido containing 11 carbons (e.g., 4(1-naphthylsulfonylaminocarbonylphenyl), an acylsulfonamido containing 14 carbons (e.g., 4-(4-bromophenylsulfonylamino(benzyl)carbonyl)phenyl); and an aryl group containing 6 carbons and substituted by 2 chloros;

(VI) a cycloalkyl containing 10 carbons (e.g., 1-adamantyl);

(VI)-(1) a cycloalkyl containing 5 carbons and substituted by carboxy or ethoxycarbonyl; and (X) an ethenyl group substituted by a member s elected from the group consisting of carboxy, ethoxycarbonyl, ureidocarbonyl (e.g., Z-2-(aminocarbonylamino)ethenyl)), acylsulfonamidophenyl (e.g.,2-[4-[(4-chlorophenyl)sulfonylaminocarbonyl]phenyl]ethenyl), and 4-carboxyphenyl (e.g., E-2-(4-carboxyphenyl)ethenyl;

$R^4$ selected as hydrogen;

$R^5$ selected from the group consisting of:

(I) n-butyl;

(II)(q) ethyl substituted by aralkoxycarbonyl wherein the aralkoxy contains 7 carbons; and (II)(z) butyl substituted by aralkyloxycarbonylamino wherein the aralkyl group contains 7 carbons;

A is as defined above; and n=1.

The following provisos apply to the compounds of this invention:

(1) alkyls may be straight or branched chain;

(2) no carbon of an alkyl may be directly bonded to two heteroatoms;

(3) no heteroatom may be directly bonded to a sulfur, nitrogen or oxygen; and (4) alkenyls of IX and X for $R^3$ may not be 1,1-disubstituted, and a carbon of a double bond may not be directly bonded to an oxygen or nitrogen.

The salts of the compounds of formulae Ia, Ib and Ic include pharmaceutically-acceptable base- or acid-addition salts such as those made with a mineral acid, e.g., hydrochloric, or an organic acid such as citric, maleic, fumaric or acetic. Base-addition salts include those made with alkali metal hydroxides such as sodium hydroxide, alkali metal carbonates and bicarbonates, alkaline earth hydroxides and organic amine salts. Such salts may be prepared by dissolving the peptide derivative in a mixture of water and a water-miscible organic solvent, adding an aqueous solution of the base and recovering the salt from the aqueous solution.

The preferred compounds of the present invention are of the S configuration (i.e., that of the naturally occurring L-amino acids) at chiral centers identified by * in formulae IIa, IIb, and IIc below. The methods of synthesis described below in Methods A and B provide a diastereomeric mixture as a result of the presence of the products with both the R and the S configurations at the chiral center identified by the symbol Δ. The methods of separation and synthesis described below in Methods C and D provide compounds which are substantially enantiomerically and diastereomerically pure. The preferred compounds are those assigned the S configuration at the center identified by the symbol Δ.

As will be appreciated by those skilled in the art, the activity of the individual isomers is not the same and, it is therefore preferred to utilize the more active isomer. The present invention includes both the diastereomeric mixture and the active S and R isomers.

As will be appreciated by those skilled in the art, the trifluoromethyl ketones can exist as solvates, particularly hydrates, represented by formulae IIIa, IIIb and IIIc, and these are encompassed by the present invention.

It is preferred to prepare the peptide derivatives of the present invention from commercially available alpha amino acids (i.e., those in which the $NH_2$ group is attached to the carbon atom next to the —COOH group). Because of this the preferred $R^2$ and $R^5$ substitutents in the above formulae for tri- and tetrapeptide derivatives are those obtained from one of the following amino acids: alanine, valine, norvaline, leucine, isoleucine, norleucine, phenylalanine, tryptophan, tyrosine, asparagine, glutamine, aspartic acid, glutamic acid, lysine, threonine, serine, α-aminobutyric acid, and phenylglycine.

Preferred groups of compounds include those listed as the main title for each of Examples 6, 11, 15–18, 20–28, 51–56, 58, 59, 62, 63, 65, 68, 71, 72, 74, 75, 77–79, 82, 84–91, 93–111, 114, 115, 117, 119 and 121–126. Of these the ones for Examples 16, 24, 27, 52, 58, 71, 74, 77–79, 85, 89, 93–96, 98, 100, 104–107, 110, 114, 115, 119 and 123–125 are more preferred and those of Examples 77, 95, 104, 114 and 115 are the most preferred.

According to a further feature of the invention there are provided pharmaceutical compositions comprising a pharmaceutically-effective amount of at le ast one peptide derivative of formulae Ia, Ib or Ic and a pharmaceutically-acceptable diluent or carrier.

The compounds of formulae Ia, Ib and Ic can be prepared as follows:

Method A

Stage 1 is the preparation of the aminoalcohol of formula V (conveniently isolated as the hydrochloride salt). Henry condensation (McBee, E. T., et al, *J. Amer. Chem. Soc.*, 78:4053 (1956))of an appropriate nitroalkane of formula $R^1CH_2NO_2$ (prepared by standard methods if not otherwise available) with trifluoroacetaldehyde ethyl hemiacetal of formula [$CF_3CH(OH)OCH_2CH_3$] provides a nitroalcohol of formula VI which is obtained as a mixture of two racemic diastereomers ([2(RS),3(RS)] and [2(RS),3(SR)]). (For example, see Example 1b.) Reduction of the nitro group in a compound of formula VI with an appropriate reducing agent affords a compound of formula V as a mixture of two racemic diastereomers ([2(RS),3(RS)]

and [2(RS),3(SR)]). (For example, see Example 1c.) This amine salt is used directly for further synthesis.

Stage 2 is the conversion of a compound of formula V into key intermediates of formulae IVa, and IVb and IVc using methods commonly known to those skilled in the art, such as those described in M. Bodanszky, *Principles of Peptide Synthesis*, Springer-Verlag, Berlin, (1984), and *The Peptides. Analysis, Synthesis and Biology* (ed. E. Gross and J. Meienhofer), Vols. 1–5, (Academic Press, New York) 1979–1983. Use of appropriately N-protected cyclic amino acids (such as CBZ-proline), followed by peptide coupling procedures and appropriate amino deprotection affords compounds of formula IVa. Similar coupling with appropriate N-protected dipeptide acids and tripeptide acids and deprotection affords compounds of formulae IVb and IVc, respectively. In addition, compounds of formula IVa can be converted into compounds of formulae IVb or IVc by utilizing the same peptide methodology. The products obtained as here described are mixtures ([2(RS), 3(RS)] and [2(RS),3(SR)]) unless a separation is carried out.

Stage 3 is the conversion of intermediates of formulae IVa, IVb, or IVc into intermediates of formulae VIIa, VIIb or VIIc by their reaction with appropriate reagents for the formation of amides, ureas, urethanes, and sulfonamides including acid chlorides, anhydrides, mixed anhydrides, isocyanates, carbonates such as 4-nitrophenyl carbonates (prepared as described in Kunz, H. et al., *Agew. Chem. Int. Ed.* (Eng), 22, 783–784 (1983), chloroformates, sulfonyl chlorides, and sulfinyl chlorides. The products obtained as here described are mixtures ([2(RS),3(SR)] and [2(RS),3(RS)]) unless a separation is carried out.

As will be clear to one skilled in the art, the order of steps in Stage 2 and 3 may be altered if appropriate considerations relative to coupling methods, racemization, deprotection methods, etc. are followed. Thus, under appropriate conditions intermediates of formula VIIa may also be prepared directly from compounds of formula V; intermediates of formula VIIb may also be prepared directly from compounds of formulae V or IVa; and intermediates of formula VIIc may also be prepared directly from compounds of formulae V, IVa, or IVb.

Stage 4 is the oxidation of intermediates of formulae VIIa, VIIb or VIIc using oxidation methods well known in the literature to provide products of formulae Ia, Ib or Ic, respectively. Methods which are useful include the use of oxalylchloride, DMSO and a tertiary amine (see Marx, M. et al., *J. Org. Chem.*, 49,788–793 (1984) with the best results being obtained with 10–20 equivalents of oxidizing agent), the use of acetic anhydride and DMSO, the use of chromium trioxide pyridine complex in methylene chloride, and the use of Dess-Martin periodinane [1,1,1-triacetoxy-2,1-benzoxiodol-3(3H)-one] (method of Dess, D. B. et al, *J. Org. Chem.*, 48, 4155–56 (1983)). The preferred method is the use of Dess-Martin periodinane. Unless they have been separated, the products Ia, Ib and Ic obtained by this method will contain a mixture [3(RS)] which will consist substantially of two diastereomers if the centers corresponding to those indicated with an * in formulae IIa, IIb, and IIc, respectively, are substantially enantiomerically pure.

Stage 5 is the conversion of products of formulae Ia, Ib or Ic into other products of formulae Ia, Ib or Ic and includes saponification, coupling, and deprotecting reactions. The stereochemistry of the product mixture is the same as that of Stage 4.

As will be clear to one skilled in the art, alternative sequences of steps to products of formulae Ia, Ib or Ic may be followed if appropriate considerations relative to coupling methods, racemization, deprotection methods, etc. are followed. For example, in analogy to Stage 3, intermediates of formulae IVa, IVb or IVc may be converted into compounds corresponding to intermediates of formulae VIIa, VIIb or VIIc but in which the portion corresponding to formula A is protected or not fully elaborated. Deprotection or final elaboration of the portion corresponding to formula A may then be carried out before the oxidation step to provide intermediates of formulae VIIa, VIIb or VIIc. Alternatively, an oxidation step corresponding to Stage 4 may be carried out and the portion corresponding to formula A of the resulting trifluormethyl ketones may be deprotected or elaborated (analogously to Step 5) to provide corresponding products of formula Ia, Ib or Ic.

Method B is a preferred method relative to Method A

Stage 1 involves separation of the mixture of racemic diastereomers of formula VI obtained as the product of Method A, Stage 1, by fractional distillation and crystallization to obtain a nitro alcohol of formula VI as a substantially pure racemic diastereomer [2(RS),3(SR)] substantially free of the other racemic diastereomer [2(RS),3(RS)]. Reduction of the nitro group by the preferred method of hydrogenation over a 10% palladium on carbon catalyst provides a compound of formula V as one racemic diastereomer [2(RS),3(SR)] substantially free of the other racemic diastereomer. (It will be appreciated by one skilled in the art that, alternatively, the diastereomer [2(RS),3(RS)] may also be used for the production of compounds of this invention.)

Stage 2 is the same as in Method A but uses the amine of formula V prepared as described in Method B, Stage 1. The products obtained by this method are substantially pure [2(RS),3(SR)] mixtures.

Stage 3 is the same as in Method A but uses the product prepared according to Method B, Stage 2. The products obtained by this method are substantially pure [2(RS),3(SR)] mixtures.

As in Method A, the order of steps in Stage 2 and Stage 3 may be altered under appropriate conditions.

Stage 4 is the same as Stage 4 of Method A. The product mixture obtained is the same as the product mixture obtained in Method A, Stage 4.

Stage 5 is the same as that of Method A, Stage 5.

Method C is a method for direct synthesis of individual ("resolved") isomers of formulae Ia, Ib, and Ic which are substantially free of the other diastereomers, for example, for products corresponding to IIa, IIb, and IIc in which the centers corresponding to * and a are all S Stage 1 involves resolution of the racemate of formula V prepared according to Method B, Stage 1. After the free base corresponding to V is liberated, resolution is carried out by formation of the diastereomeric salts with D-tartaric acid and separation of those salts by fractional crystallization. The desired amine is then obtained from the separated salts by freeing the base to afford, for example, the free base corresponding to 2(R)3(S) in a compound of formula V. The product thus obtained is substantially enantiomerically and diastereomerically pure.

Stages 2 and 3 are substantially the same as Stages 2 and 3 in Methods A and B, but limited to methods which will avoid racemization of centers which correspond to those marked * in formulae IIa, IIb, and IIc. The products thus obtained are essentially enantiomerically and diastereomerically pure.

Stage 4 is limited to methods which will avoid racemization at the centers labelled * and Δ in formulae IIa, IIb and IIc. The preferred method is the use of Dess-Martin periodinane. The products Ia, Ib and Ic thus obtained are essentially enantiomerically and diastereomerically pure.

Stage 5 is limited to methods which will avoid racemization at the centers labelled * and Δ in formulae IIa, IIb and IIc.

Method D

Stage 1 is a separation of compounds of formulae Ia, Ib or Ic prepared by Methods A or B which are diastereomeric mixtures (owing to the 3(RS) center) into their single isomers which are substantially diastereomerically and enantiomerically pure. The preferred method for completing this separation is the use of preparative chromatography, e.g. medium pressure liquid chromotography (MPLC) and high pressure liquid chromatography (HPLC).

Stage 2 is the same as Stage 5, Method C.

Inhibition Measurements

The potency of compounds of the invention to act as elastase inhibitors was initially determined by the ability of a compound of the invention to inhibit the action of human leukocyte elastase (HLE) on a low molecular weight peptide substrate. The potency of an inhibitor is evaluated by obtaining a kinetic determination of the dissociation constant, $K_i$, of the complex formed from the interaction of the inhibitor with HLE. The substrate used was the anilide methoxysuccinyl-alanyl-alanyl-prolyl-valine-p-nitroanilide as described by Ko Nakajima et al. in the *J. Biol. Chem.*, 254:4027–4032 (1979) and by T. Teshima et al. in *J. Biol. Chem.*, 257:No. 9, 5085–5091 (1982). The HLE enzyme used in these studies may be obtained from Elastin Products of St. Louis, Missouri or can be purified according to B. R. Viscarello et al. in *Preparative Biochemistry*, Vol. 13, pages 57–67, (1983) as follows, all work having been done in a cold room at 4° C.

Salt Extraction-DNase Treatment: The starting material, 193 g of purulent sputum, was homogenized with 200 ml of cold distilled water and centrifuged at 30,000×gravity for 20 min. at 4° C. The supernatant was discarded and the pellet extracted with high salt and treated with DNase as per the method of D. Y. Twumasi et al. in *J. Biol. Chem.*, 252: 1917–1926 (1977). Chromatography on Elastin Agarose: The precipitate from the DNase digest was taken up in two 40 ml portions of 50 mM Tris, 1.0 M NaCl, pH 8; the suspension was centrifuged and the resulting supernatant applied directly to a column of soluble elastin-Sepharose 4B (2.5×20 cm). The column was washed with equilibrating buffer (50 mM Tris, 50 mM NaCl, pH8.0) until the optical density at 280 nm ($OD_{280}$) of the eluate returned to baseline. Additional contaminating protein was eluted with two column volumes of 50 mM acetate, 1.0 M NaCl, pH 5.0. Elastase and cathepsin G (HLC-G) were finally eluted with 50 mM acetate, 1.0 M NaCl, 20% DMSO, pH 5.0. The column was developed at 6 ml/min with the collection of 10 ml fractions. The active fractions were pooled, dialyzed vs. two 6 liter changes of 50 mM acetate, 0.1 M NaCl, pH 5.5, and concentrated to 40 ml on an Amicon® ultrafiltration unit (YM-10 membrane). CM-Chromatography: The concentrated active fraction was applied to a column of CM-Sephadex® C-50 (2.2×10 cm) previously equilibrated with 50 mM acetate, 0.1M NaCl, pH 5.5 and the column was then washed with this buffer to remove contaminating protein. Elution was continued with 50 mM acetate, 0.2M NaCl, pH 5.5 and resulted in the displacement of a peak of activity assayed against Bz—Phe—Val—Arg—pNA. HLE was next eluted with the acetate buffer containing 0.45M NaCl, while elution of HLC—G required the presence of 1.0M NaCl in the buffer as described by R. Martodam et al. in *Preparative Biochemistry*, Vol. 9, pages 15–31 (1979). This column was developed at 30 ml/hr with the collection of 5.5 ml fractions. From the thus purified HLE, a standard rate of production of p-nitroaniline was measured at 25° C spectrophotometrically in the visible spectrum at 410 nanometers with automatic data acquisition from a Cary 210 spectrophotometer obtained from Varian Associates. Reactions were initiated by injection of 10 microliters of the HLE solution into a 3 milliliter cuvette containing 2.89 milliliters of buffer (10 millimolar sodium phosphate, 500 millimolar NaCl, pH 7.6), 50 microliters substrate solution in DMSO, and 50 microliters of DMSO. Initial, steady-state reaction velocities of p-nitroaniline production were calculated by a fit of the experimental data to a linear dependence on time by linear least squares. This velocity, determined with no inhibitor present, was used as a standard in the calculation of inhibitor $K_i$ values.

In general, the peptide derivatives of the present invention were found to be "slowbinding" inhibitors of HLE and therefore required special methods of analysis to accurately determine $K_i$ values for their inhibition of HLE (see Williams, J. W. and Morrison, J. F., *Meth. Enz.* 63, 437 (1979) for a description of these methods.) In a typical experiment, 2.89 ml of buffer (10 millimolar sodium phosphate, 500 millimolar sodium chloride, pH 7.6), 50 microliters of inhibitor solution in DMSO, and 50 microliters of substrate solution in DMSO were added to a 3 milliliter cuvette. The cuvette was stoppered, inverted several times to mix its contents and maintained at (25° C.) in the spectrophotometer. After a period of five minutes to allow the reaction solution to come to thermal equilibrium, 10 microliters of stock enzyme solution were added to the cuvette to initiate the reaction. Duplicate or triplicate runs were done at zero inhibitor concentration and at least three non-zero inhibitor concentrations. $K_i$ values were calculated according to methods outlined in the above reference by Williams and Morrison. The $K_i$ values for selected compounds were less than $10^{-7}$ M.

Animal Models

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with Brevital. Phosphate buffered saline (PBS) pH 7.4, either alone or containing 400 ξg of human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them either with or at various times prior to administration of HLE to determine their utility in preventing an HLE lesion. Compounds of this invention produced statistically significant reductions in wet lung weight and total lavagable cells relative to HLE alone. Compounds of the present invention exhibited activity in at least one of the tests described above under Inhibition Measurement or Animal Model. It should be noted that there was not always a direct correlation between the activities of the compounds measured as $K_i$ values in the Inhibition Measurement test and the reduced values for total lavagable cells and wet lung weights relative to the administration of HLE alone obtained in the Animal Model test. It is thought that the Animal Model test is more predictive of the activity of such compounds in the treatment of emphysema.

Pharmacokinetics: Male Syrian hamsters (80 to 120 g) are injected intravenously with the test compound. Prior to injection and at varying time periods thereafter, they are lightly anesthetized with ether and blood samples of approximately 0.2 ml each are withdrawn by cardiac puncture. The blood is expressed into 2 ml centrifuge tubes and allowed to clot for one hour. The sample is then centrifuged and the serum removed.

Drug levels are determined by first inactivating endogenous elastase inhibitors by incubation of 50 microliters of serum with an equal volume of buffer containing 5 mg/ml bovine pancreatic trypsin for 5 min. The trypsin inactivated serum (10 microliters) is then added to a 0.52 ml cuvette containing buffer made 20 nM with respect to HLE. After an additional 30 min. incubation, the reaction is started by the addition of substrate (350 microliters) (MeOSuc—Ala—Ala—Pro—Val—pNA, 1.6 mm) and the reaction monitored spectrophotometrically at a wavelength of 410 nM. For comparative purposes, serum persistence of the test compounds is determined in the following manner:

Percent inhibition of serum samples is calculated as follows:

$$\text{percent inhibition} = \frac{V_o - V_i}{V_o} \times 100$$

where Vo is the velocity obtained in the presence of control serum and Vi is the velocity of the inhibited reaction. Data are expressed as log percent inhibition vs. time post inhibitor administration. An approximate serum half-life ($t\frac{1}{2}$) is calculated from the resultant curve.

The compounds of the present invention may be administered to a warm-blooded animal in need thereof, particularly a human, for the treatment of conditions of pulmonary emphysema, atherosclerosis, rheumatoid arthritis, and osteo arthritis, in particular for emphysema. The mode of administration may be oral, parenteral, including the subcutaneous deposit by means of an osmotic pump, or via a powdered or liquid aerosol. These may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice e.g. as described in U.S. Pat. No. 3,755,340. For parenteral administration, a 1 to 10 ml intravenous, intramusular or subcutaneous injection would be given containing about 0.02 to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA). In a powdered aerosol, compounds of the invention may be administered in the same manner as cromolyn sodium via a Spinhaler ® turbo-inhaler device obtained from Fisons Corp. of Bedford, Mass. at a rate of about 0.1 to 50 mg per capsule, 1 to 8 capsules being administered daily for an average human. Each capsule to be used in the Spinhaler ® contains the required amount of a compound of the invention with the remainder of the 20 mg capsule being a pharmaceutically-acceptable carrier such as lactose. In a liquid aerosol, the compounds of the invention are administered at the rate of about 100 to 1000 micrograms per "puff" or activated release of a standard volume of propellant. The liquid aerosol would be given at the rate of 1 to 8 puffs per day with variation in dosages due to the severity of the condition being treated, the weight of the patient and the particle size distribution of the aerosol since smaller particles will achieve greater lung penetration. Propellants, e.g., a fluorinated hydrocarbon or isobutane, containers, valves and actuators for liquid aerosols are described by L. Lachman et al. in "The Theory and Practice of Industrial Pharmacy", Lea and Febiger, Philadelphia (1976).

In the following Examples and throughout the specification, the following abbreviations and conventions are used: atm (atmospheres); bp (boiling point); °C. (degrees Celsius) with all temperatures being in °C. unless otherwise noted; g (grams); hr (hours); mg (milligrams); min (minutes); ml (milliliters); l (liters); mol (moles); mmol (millimoles); mp (melting point); bp (boiling point); N (normal); nm (nanometers); nM (nanomolar); satd or sat'd (saturated); aq (aqueous); conc (concentrated); ×(times); room temperature (20°–23°); DCC (1,3-dicyclohexylcarbodiimide); DMF (dimethylformamide); DMSO (dimethyl sulfoxide); Et$_2$O (diethyl ether); EtOAc (ethyl acetate); HOAc (acetic acid); HOBT (1-hydroxybenzotriazole); MeOH (methyl alcohol); EtOH (ethyl alcohol ); Pd/C (palladium on charcoal catalyst ); pNA (paranitroanilide); THF (tetrahydrofuran); CBZ (benzyloxycarbonyl); t-BOC (tertiarybutyloxycarbonyl); DMF (dimethylformamide); TEA (triethylamine); DCC (1,3-dicyclohexylcarbodiimide); AcOH (acetic acid); S.M. (starting material); NMM (N-methylmorpholine); ≦ (less than or equal to); TEA (triethylamine); TFA (trifluoroacetic acid); Ac$_2$O (acetic anhydride); CDI (carbonyldiimidazole); WSCDI (water soluble carbodiimide:1-ethyl-3-(3-dimethylaminopropyl)carbodiimidehydrochloride); DMAP (4-dimethylaminopyridine); Dess-Martin periodinane (1,1,1-triacetoxy-2,1-benzoxiodol-3(3H)-one); HCl gas (gaseous HCl)—otherwise, HCl is an aqueous solution; Rh/C (rhodium on charcoal catalyst); φ (phenyl group); TLC (thin layer chromatography on silica gel unless otherwise specified); $R_f$ (relative mobility in TLC); MPLC (medium pressure liquid chromatography); HPLC (high pressure liquid chromatography), $t_R$ (HPLC retention time in min), FR (HPLC flow rate in ml/min); Col A (Zorbax ® ODS analytical column, 4.6 mm×25 cm); Col B (Phenomenex ® Zorbax ® C.-8 analytical column, 4.6 mm×35 cm); Col C (Altex Ultrasphere ®/Octyl 10 mm I.D.×25 cm 5 micron analytical and preparative column); flash chromatography (flash column chromatography on silica gel unless otherwise specified); suction chromatography (suction column chromatography on silica gel). In addition, C, H, N, etc. (the conventional symbols for the elements) are used; 133.3 Pascals=1 Torr as a conversion factor with 760 Torr =14.7 pounds per square inch (psi); $^1$H NMR (nuclear magnetic resonance) spectra were obtained using either a 80 MHz or 250 MHz instrument and tetramethylsilane (TMS) as an internal standard (the solvent for the particular example is noted in the example), δ (parts per million downfield from TMS); with s (singlet); d (doublet); dd (doublet of doublets); m (multiplet). Nomenclature: For uniformity and clarity, "amino acid sequence type" names are used whenever possible. In addition, amines of formula V, nitro compounds of formula VI, and the N-substituents of C-terminal amides of formulae I, II, III, IV, and VII which are formally derived from V are numbered as shown in formula V, VI and the partial formulae set out following them.

When needed or as noted, various examples were repeated if more material was required.

EXPLOSION WARNING: The nitro alcohols of formula VI and their nitroalkane precursors are potentially explosive. The compound of formula VI, $R^1$=CH(CH$_3$)$_2$ (Examples 1b and 4b) is thermally unstable and on a small scale, has been observed to decompose with considerable violence in the range 170°–180° C. Samples of the material have been safely distilled at reduced pressure (95°–105° C./2.0 torr). Recommendtions for safe distillation include keeping the oil bath below 110° C., never taking still residues below 15% of the orginal crude volume, and conducting the distillation behind a safety screen.

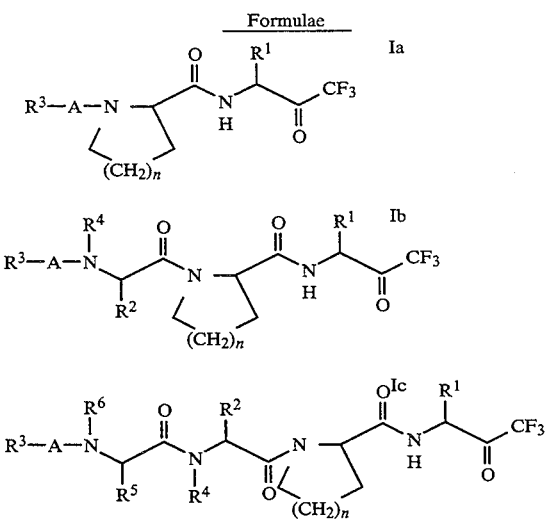

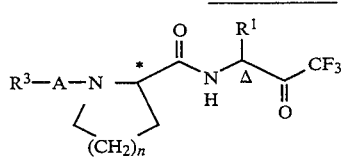

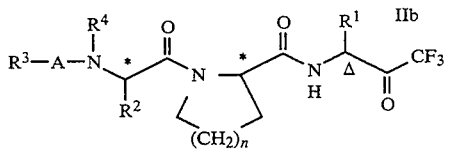

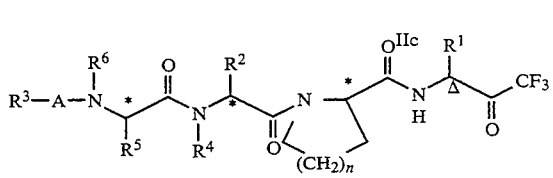

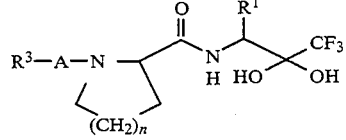

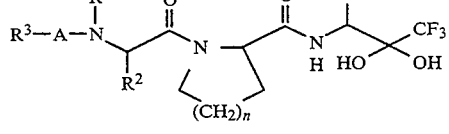

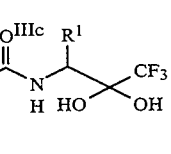

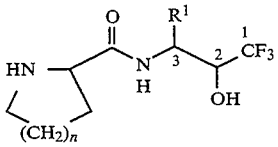

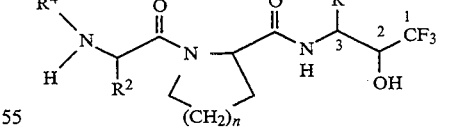

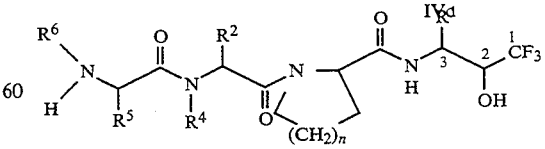

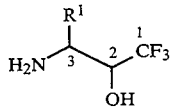

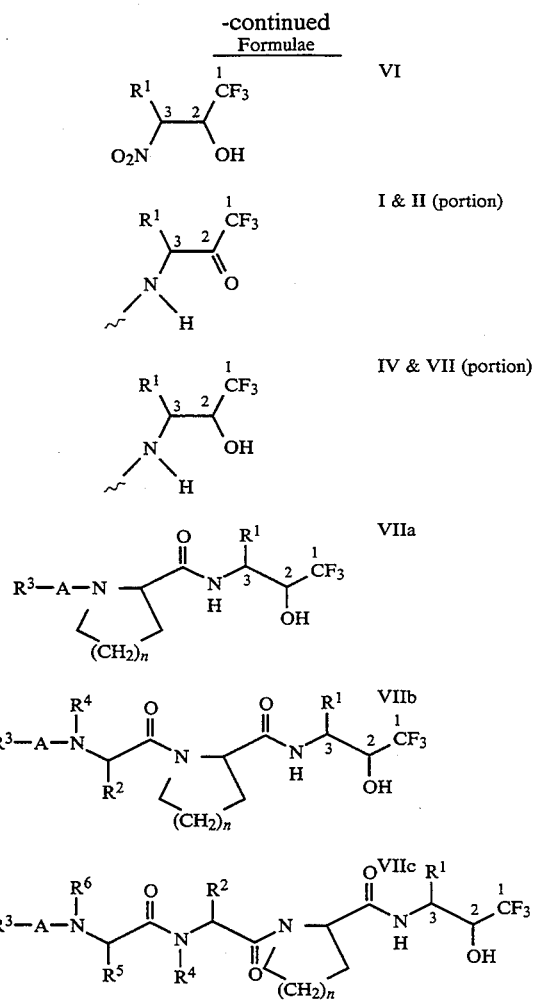

-continued
Formulae

VI

I & II (portion)

IV & VII (portion)

VIIa

VIIb

VIIc

EXAMPLE 1

2
(RS),3(SR)-3-Amino-4-methyl-1,1,1-trifluoro-2-pentanol hydrochloride salt a. 2-Methyl-1-nitropropane 1-Iodo-2-methylpropane (94.0 g, 0.51 mol) was added dropwise to a pre-cooled (0° C.) suspension of AgNO2 (100.0 g, 0.65 mol) in Et2O (180 ml). The reaction was protected from light and stirred overnight as it was allowed to warm to room temperature. The reaction mixture was filtered through Celite ®. The filtrate was concentrated under vacuum and the residue was distilled under vacuum (caution: potentially explosive) to give the product (37.7 g, 0.366 mol); b.p. 61°–65° C. at 6913.6 Pascals (52 mm Hg).

b.
2(RS),3(SR)-4-Methyl-3-nitro-1,1,1-trifluoro-2-pentanol

See EXPLOSION WARNING

1-Nitro-2-methylpropane (37.7 g, 0.366 mol) from Example 1a, trifluoroacetaldehyde ethyl hemiacetal (58.5 g, 0.366 mol, 90% purity) and K2CO3 (3.4 g, 0.025 mol) were mixed and stirred at 60° C. for 3 hr. and then at room temperature for 3 days. Brine (75 ml) and 1N aqueous HCl (50 ml) were added and the lower organic layer separated. The aqueous layer was extracted with Et2O (twice with 250 ml each) and the combined organic layers were washed with brine, dried over Na2SO4, filtered and concentrated under vacuum. The residue was purified by flash chromatography on silica gel with a gradient elution of CH2Cl2:hexane (50:50), CH2Cl2:hexane (75:25), CH2Cl2 (100%) and MeOH:CH2Cl2 (5:95) to give the product (44.9 g); TLC, R$_f$=0.65, silica gel, EtOAc: CHCl3 (5:95).

c.
2(RS),3(SR)-3-Amino-4-methyl-1,1,1-trifluoro-2-pentanol hydrochloride salt

A solution of a portion of the product of Example 1b (37.0 g, 0.184 mol) in Et2O (200 ml) was added dropwise to a suspension of lithium aluminum hydride (22.0 g, 0.58 mol) in Et2O (800 ml). The reaction mixture was stirred for 45 min. and a saturated aqueous solution of Na2SO4 (110 ml) was carefully added. The resulting suspension was filtered; the filtrate was treated with ethereal HCl and concentrated under vacuum to give the product (37.6 g) which was used without further purification. $^1$H NMR data (CD3COCD3)(250 MHz): 1.2δ, m, 6H; 2.3δm, 1H; 3.58δ, m, 1H; 4.98δ, m, 2H; 7.78δ, m, (NH2).

EXAMPLE 2

2(RS),3(SR)-N-[3-(4-Methyl-1,1,1-trifluoro-2-hydroxypentyl)]-L-prolinamide a. 2
(RS),3(SR)-1-[(Phenylmethoxy)carbonyl]-N-[3-(4-methyl-1,1,1-trifluoro-2-hydroxypentyl)]-L-prolinamide A solution of isobutyl chloroformate (11.01 g, 0.08 mol) in dry THF (30 ml) was added dropwise over 5 min to a pre-cooled solution (−15° C.) of CBZ-L-proline (19.21 g, 0.077 mol) and N-methylmorpholine (8.18 g, 0.081 mol) in THF (300 ml) under a nitrogen atmosphere. The reaction mixture was stirred at −15° C. for 15 min. The reaction temperature was then reduced to −40° C. and a solution of a portion of the product of Example 1c (16.00 g, 0.077 mol) and N-methylmorpholine (8.18 g, 0.081 mol) in THF (200 ml) was added dropwise to the reaction. The reaction mixture was stirred at −40° C. for 1 hr. and then allowed gradually to warm to room temperature and stirred for an additional hour. The reaction was filtered and concentrated under vacuum. The resulting syrup was dissolved in CHCl3, and washed with aqueous 20% citric acid (twice with 75 ml each). The organic layer was concentrated under vacuum to give the crude product as a white cloudy syrup. The crude product was triturated with ether: hexane (1:2) to give 3 crops of the product as a white powder (17.11 g); TLC, R$_f$=0.47, silica gel, MeOH:CHCl3 (3:97); m.p., 152°–154° C.; HPLC, t$_R$=14.06, 16.63, 18.23, 19.00, Zorbax ® ODS analytical column, H2O:CH3CN (70:30), flow rate=3 ml/min.

b.
2(RS),3(SR)-N-[3-(4-Methyl-1,1,1-trifluoro-2-hydroxypentyl)]-L-prolinamide

The product of Example 2a (2.00 g, 4.97 mmol) was dissolved in absolute ethanol (50 ml), 10% Pd/C (0.5 g) was added and the reaction mixture was hydrogenolyzed (310126.53 Pascals, 45 psi hydrogen) for 3 hr. at room temperature. The reaction mixture was filtered through Celite ® and the solvent was removed under vacuum to give the product (1.36 g) which was used without further purification.

EXAMPLE 3

2(RS),3(SR)-L-Valyl-N-[3-(4-methyl-1,1,1-trifluoro-2-hydroxypentyl)]-L-prolinamide a. N-[(Phenylmethoxy)carbonyl]-L-valyl-L-proline methyl ester

1-Hydroxybenzotriazole (163.3 g, 1.2 mol) was added to a pre-cooled (0° C.) solution of N-benzyloxycarbonyl-L-valine (151.8 g, 0.6 mol) in DMF (1.3 liter) and stirred for 15 min. A suspension of L-proline methyl ester hydrochloride (100.0 g, 0.6 mol) and TEA (64.2 g, 0.63 mol) in DMF (0.7 liter) was added, followed by DCC (137.1 g, 0.66 mol). The reaction mixture was stirred for 3 hr. at 0° C. and then at room temperature for 3 days. The reaction mixture was filtered and the filtrate concentrated under vacuum. The residue was mixed with EtOAc (0.75 liter) and filtered. The filtrate was washed successively with 20% aqueous citric acid (0.75 liter), saturated aqueous $NaHCO_3$, and brine. The organic phase was dried over $MgSO_4$, filtered and concentrated under vacuum to give the crude product (271.3 g). The product was purified by flash chromatography on silica gel using a gradient elution starting with $CH_2Cl_2$ and finishing with $MeOH:CH_2Cl_2$ (4:96) to give the product (218.1 g); TLC, $R_f=0.48$, silica gel, $MeOH:CHCl_3$(5:95).

b. N-[(Phenylmethoxy)carbonyl]-L-valyl-L-proline

To a solution of a portion of the product of Example 3a (158.8 g, 0.438 mol) in MeOH (1.6 liter) was added 1N aqueous NaOH (500 ml) and the solution stirred at room temperature for 17 hr. 1N aqueous NaOH (100 ml) was added and stirring continued for 5 hr. Additional 1N aqueous NaOH (50 ml) was added and the reaction was stirred overnight. The reaction was concentrated under vacuum to remove the MeOH. $H_2O$ (1.0 liter) was added and the aqueous solution extracted with $Et_2O$. The aqueous solution was acidified with 1N aqueous HCl (700 ml) and extracted with EtOAc. The EtOAc extracts were washed with brine, dried over $Na_2SO_4$, filtered and concentrated under vacuum to give the product (159.2 g); TLC, $R_f=0.34$, silica gel, $MeOH:CHCl_3$: AcOH (5:94:1).

c. 2(RS),3(SR)-[(Phenylmethoxy)carbonyl]-L-valyl-N-[3-(4-methyl-1,1,1-trifluoro-2-hydroxypentyl)]-L-prolinamide Isobutylchloroformate (77.3 g, 0.566 mol) was added to a pre-cooled (−15° C.) solution of N-methylmorpholine (59.25 g, 0.566 mol) and the product of Example 3b (197.2 g, 0.566 mol) in dry THF (2.5 liters) and the reaction stirred for 10 min. The temperature was reduced to −40° C. and N-methylmorpholine (59.25 g, 0.566 mol) was added, followed by the dropwise addition of a solution of the product of Example 1c (117.5 g, 0.566 mol) in THF (2.5 liter). The reaction was allowed to warm to room temperature and stirred for three days. The reaction mixture was filtered and the filtrate concentrated under vacuum. The residue was dissolved in EtOAc and washed successively with $H_2O$, 1N aqueous HCl and brine. The organic layer was dried over $Na_2SO_4$, filtered and concentrated to give the crude product (267.8 g). The product was purified by flash chromatography on silica gel using a gradient elution of THF:toluene (5:95) to THF:toluene (25:75) to give the product (183.8 g); TLC, $R_f=0.4$, silica gel, THF:toluene (20:80).

d. 2(RS),3(SR)-L-Valyl-N-[3-(4-methyl-1,1,1-trifluoro-2-hydroxypentyl)]-L-prolinamide A mixture of a portion of the product of Example 3c (36.7 g, 0.073 mol) and 10% Pd/C (10%, 50% water wet) in EtOH (0.6 liter) was hydrogenated on a Parr shaker (303,924 Pascals, 3 atm $H_2$). After 1 hr. the reaction vessel was evacuated and re-pressurized with $H_2$. After an additional 0.5 hr. the reaction mixture was filtered through Celite ® and concentrated under vacuum to give the product (26.0 g); TLC, $R_f=0.16$, silica gel, $MeOH:CHCl_3$ (5:95).

EXAMPLE 4

2(RS),3(SR)-3-Amino-4-methyl-1,1,1-trifluoro-2-pentanol hydrochloride salt a. 2-Methyl-1-nitropropane

An alternative method for making the compound of Example 1a is as follows.

A 5-liter, 3-necked, round-bottomed flask was equipped with a mechanical stirrer, thermometer, addition funnel and $N_2$ inlet. The flask was charged with $AgNO_2$ (1006.8 g, 6.54 mol) in $Et_2O$ (2.5 liter), and isobutyl iodide (927.2 g, 5.03 mol) was placed in the addition funnel. Both the flask and the addition funnel were wrapped in aluminum foil to protect the reaction from light. After the stirred suspension was cooled to approximately 5° C. (ice bath), dropwise addition of the iodide over a 2 hr period was begun. The reaction temperature was maintained at or less than 5° C. throughout the course of the addition. When the addition was complete, the reaction vessel was packed in ice and allowed to warm slowly to room temperature overnight. NMR analysis of an aliquot taken from the reaction mixture after 48 hr of stirring demonstrated that all of the isobutyl iodide had been consumed. The reaction mixture was filtered through Celite ® to remove silver salts and the filter cake was washed with $Et_2O$ (3×500 ml). The combined filtrates were dried $MgSO_4$, filtered and concentrated on a rotary evaporator (bath temp=35° C.) to about 600 ml. Fractional distillation (atmospheric pressure) (caution: potentially explosive) gave the purified nitro compound (350.4 g, 68% yield); b.p. 135°–142° C.

b. 2(RS),3(SR)-4-Methyl-3-nitro-1,1,1-trifluoro-2-pentanol

See EXPLOSION WARNING

A 3-liter, 3-necked, round-bottomed flask equipped with a mechanical stirrer and $N_2$ inlet was charged with $K_2CO_3$ (470.0 g, 3.4 mol), the product of Example 4a (350.0 g, 3.4 mol) and finally trifluoroacetaldehyde ethyl hemiacetal (708.0 g, 4.4 mol). The mixture was vigorously stirred at room temperature for 76 hr, at which time $^1$H-NMR demonstrated the nearly complete consumption of the nitroalkane. The reaction mixture was diluted with $CH_2Cl_2$ and filtered. The filtrate was treated with aqueous HCl until pH=3. The layers were separated and the aqueous layer was washed with $CH_2Cl_2$ (500 ml). The combined $CH_2Cl_2$ portions were washed with $H_2O$ (1 liter) and brine (1 liter). Drying ($MgSO_4$) and concentration gave 854.6 g of crude product as a yellow oil. $^1$H-NMR showed the two diastereomeric nitro alcohols (present in the ratio of about 3:1 as quantified by integration of the alcohol protons) which consistently appear in the range δ6.0–6.5 when run in acetone-d$_6$ contaminated by solvents and small amounts of starting materials.

Distillation at reduced pressure gave the following fractions:

|   | Wt. | BP (°C.) |   |
|---|---|---|---|
| A | 191.7 g | 42°–50° C./atm. | S.M. + solvents |
| B | 34.8 g | 35°/1 torr–45°/.5 torr |   |
| C | 213.6 g | 45°/.5 torr–95°/1.5 torr |   |
| D | 337.8 g | 95°/1.5 torr–105°/2 torr |   |
| E | 114.0 g | trap volatiles |   |

To simplify purifications in subsequent synthetic steps, an effort was made at this point to obtain the major diastereomeric pair in a substantially pure state and to advance only this material through the sequence. The major diastereomeric pair crystallizes from the mixture of diastereomers, as well as from cold pentane, to yield colorless needles. Thus, fraction C from the above distillation was allowed to crystallize overnight in a refrigerator. The product was collected, washed with cold pentane and dried for several hours in a vacuum oven (Caution! This material is somewhat volatile and significant quantities can be lost under extended vacuum treatment) to give 52.0 g of substantially pure material. The fractions known (by NMR) to contain significant quantities of the desired isomer were repetitively treated in this fashion (and redistilled to provide new fractions further enriched in the desired diastereomer) to eventually obtain a total of 197.7 g of substantially pure nitro alcohol. This amount represents the type of work done, but it does not reflect the upper limit of the yield.

c. 2(RS),3(SR)-3-Amino-4-methyl-1,1,1-trifluoro-2-pentanol hydrochloride salt Anhydrous EtOH (232 ml) was added to 10% Pd/C catalyst (2.30 g) under N$_2$*. The product of Example 4b (22.93 g, 0.144 mol) was added and the resultant mixture was placed on a Parr hydrogenation apparatus (about 480,000 Pascals, 55 psi H$_2$) overnight. Catalyst was removed by filtration through Celite ®. The filter cake was then washed with EtOH. HCl gas was bubbled through the combined filtrates until approximately 8 g (about 0.22 mol) were absorbed. The solution was concentrated on a rotary evaporator and the resultant residue was concentrated several times from Et$_2$O to obtain a white solid. The solid was washed with Et$_2$O and dried overnight in a vacuum oven to yield 20.79 g (88%) of amine hydrochloride. For the m.p., with slow heating the material softens at 90° C. and melts at 118°–120° C. When a sample is plunged into a bath preheated to 110° C., it melts instantaneously.

*Less active catalysts (e.g., 10% Pd/BaSO$_4$, wet 10% Pd/C) or insufficient reaction times may lead to the production of one or more by-products.

EXAMPLE 5

2 (RS),3(SR)-L-valyl-N-[3-(4-methyl-1,1,1-trifluoro-2-hydroxypentyl)]-L-prolinamide a. N-[(Phenylmethoxy)carbonyl]-L-valyl-L-proline methyl ester

A solution of CBZ-L-Valine (100.0 g, 0.40 mol) in DMF (1 liter, dried over sieves) was added to a 3-liter, 3-necked, round-bottomed flask equipped with a mechanical stirrer, N$_2$ inlet and a thermometer. The reaction was cooled to 0° C. and HOBT hydrate (108.1 g, 0.80 mol) was added. Approximately 15 min of stirring were allowed before adding a DMF (500 ml) slurry of L-proline methylester hydrochloride (66.2 g, 0.40 mol) and TEA (41.8 g, 0.42 mol) in one portion. Additional DMF (500 ml) was used to complete the transfer of the slurry. DCC (90.8 g, 0.44 mol) was added to the reaction and was washed down with DMF (100 ml). The reaction was stirred for 3 hr at 0° C. before allowing it to warm to room temperature and stir for 3 days. The reaction mixture was then filtered and the filtrate concentrated at reduced pressure. The filter cake was washed with EtOAc (3×1 liter), and concentration of the resultant filtrate gave material that was combined with the residue from concentration of the DMF solution. The combined product mixture (about 2.5 liters) was diluted with Et$_2$O (2 liters) and stored in the refrigerator overnight. Precipitate was removed by filtration. When the filtrate was washed with 1N HCl (1 liter), additional precipitate formed and was removed by filtration. The filtrate was then washed with 1N HCl (1 liter), H$_2$O (0.5 liter), saturated NaHCO$_3$ (2×1 liter) and brine (0.5 liter). Drying MgSO$_4$ and concentration gave 587.2 g of crude product. This material was flash chromatographed on silica gel (3.5 kg) with gradient elution (CH$_2$Cl$_2$ to 5% MeOH:CH$_2$Cl$_2$ (5:95). Mixed fractions were subjected to repeated chromatography to remove impurities. Combination of the fractions containing the desired product gave 500.7 g (87%) of material contaminated with a small amount of low R$_f$ impurity; TLC, R$_f$=0.37, silica gel, Et$_2$O: hexane (3:1); R$_f$=0.53, silica gel, MeOH:CHCl$_3$ (5:95).

b. N-[(Phenylmethoxy)carbonyl]-L-valyl-L-proline

A methanolic (4 liters) solution of the product of Example 5a (500.7 g, 1.38 mol) was added to a 12-liter, 3-necked, round-bottomed flask equipped with a mechanical stirrer and an N$_2$ inlet. To the stirred solution was added 1N NaOH (1.4 liters), bringing the pH to approximately 13. After the reaction had stirred for 3 hr, the pH dropped to 11. Additional 1N NaOH (0.1 liter) was used to bring the pH to 12 and the reaction was stirred overnight at room temperature. MeOH was removed from the reaction mixture by concentration on a rotary evaporator. During the course of the solvent removal, a total of 1 liter of H$_2$O was added to reduce the concentration of the base. The aqueous solution was washed with Et$_2$O before acidifying with 1N HCl (1.5 liters) to a pH of approximately 3.5. The layers were separated and the aqueous layer was extracted with EtOAc (3×1 liter). The combined organics were washed with brine (1 liter), dried (MgSO$_4$) and concentrated to give 493.0 g (100%) of product as a white solid; TLC, R$_f$=0.51, silica gel, MeOH:CHCl$_3$ (5:95) with added AcOH.

c.
2(RS),3(SR)-[(Phenylmethoxy)carbonyl]-L-valyl-N-[3-(4-methyl-1,1,1-trifluoro-2-hydroxypentyl)]-L-prolinamide The product of Example 5b (105.3 g, 0.302 mol) was dissolved in dry THF (1.5 liters) under $N_2$ in a 3-liter, 3-necked, round-bottomed flask equipped with a mechanical stirrer, thermometer, $N_2$ inlet and an addition funnel. The solution was cooled to $-35°$ C. and treated with 1 equivalent (34 ml, 0.309 mol) of NMM. Isobutyl chloroformate (39 ml, 0.307 mol) was added dropwise over 20 min while maintaining the temperature $\leq -35°$ C. After the addition was complete, the reaction was stirred for 1 hr at $-35°$ C. A second equivalent of NMM (34 ml) was added. The product of Example 4c (62.8 g, 0.302 mol) in THF (300 ml) was then added at such a rate that the temperature was maintained at $\leq -35°$ C. After the addition was complete, the temperature was kept $\leq -35°$ C. for 1 hr before the mixture was allowed to warm to room temperature with stirring overnight. The reaction mixture was filtered and the filter cake was washed with THF (1 liter). The combined filtrates were concentrated to give 189 g of crude product. This material was flash chromatographed on silica gel (5000 ml) and eluted with THF:toluene (1:9). Once product began to elute, the solvent polarity was altered in gradient fashion: THF:toluene (15:85); THF:toluene (20:80); and, finally MeOH:THF:toluene (2.5:30:70) (MeOH use was minimized to prevent the elution of low $R_f$ impurities). Concentration of the column fractions followed by drying under vacuum overnight gave 12.0 g (8%) of slightly impure product and 131.6 g (87%) of substantially pure material. (NOTE: Solutions of this material when taken to complete dryness yielded a foam that eventually solidified under extended vacuum treatment. Care had been taken to accomplish this operation in a large enough flask to accomodate the expansion of the foam.) TLC, $R_f$=0.25, silica gel, MeOH:CHCl$_3$ (5:95); $R_f$=0.37, silica gel, THF:toluene (20:80). When the material is spotted lightly, the two isomers resolved to give spots at $R_f$=0.37 and $R_f$=0.46, silica gel, THF:toluene (20:80).

(NOTE: Maintenance of the internal temperatures quoted in this procedure appears to be crucial for obtaining substantially pure product.)

d.
2(RS),3(SR)-L-Valyl-N-[3-(4-methyl-1,1,1-trifluoro-2-hydroxypentyl)]-L-prolinamide The product of Example 5c (131.6 g, 0.262 mol) was dissolved in EtOH (750 ml) and combined with 10% Pd/C catalyst (50% $H_2O$, 13.0 g) under $N_2$ in a large Parr hydrogenation bottle. The reaction mixture was shaken under a 480,000 Pascals, 55 psi atmosphere of $H_2$ on a Parr apparatus. Repressurizing with $H_2$ was continued until no further uptake was observed. Examination of the reaction by TLC showed complete consumption of starting material. The reaction mixture was filtered through Celite ® and concentrated to a foam. This material was triturated with $Et_2O$, filtered, and dried to give 81.4 g (84%) of light grey solid; TLC, $R_f$=0.41, silica gel, CHCl$_3$:MeOH (10:1).

EXAMPLE 6

3S(orR)-Phenylmethoxycarbonyl-L-valyl-N-[3-(1,1,1-trifluoro-4-methyl-2-oxopentyl)]-L-prolinamide
(Formula Ib, $R^1$=CH(CH$_3$)CH$_3$, $R^2$=CH(CH$_3$)CH$_3$, $R^3$=$\phi$CH$_2$, $R^4$=H, A=OCO, n=1)

a. 2R,3S-3-Amino-1,1,1-trifluoro-4-methyl-2-pentanol D-tartaric acid salt

Amine hydrochloride (20 g) generated as in Example 4e was dissolved in $H_2O$ and neutralized with solid NaHCO$_3$. The aqueous solution was extracted several times with $CH_2Cl_2$. The combined extracts were dried (Na$_2$SO$_4$) and concentrated to yield the amine free base (14.04 g) as a white solid. This material was combined with D-tartaric acid (12.31 g) in boiling anhydrous EtOH (100 ml), and the resultant cloudy solution was filtered hot through filter paper. The solution was first cooled slowly to room temperature overnight and then placed in the refrigerator for several hours. Precipitate was collected on a fritted funnel, washed with cold EtOH, and dried overnight in a vacuum oven at 40°. A sample of the dried white solid (4.56 g) melted at 127°-130°. Most of this material (4.05 g) was dissolved in boiling EtOH (20 ml), and the solution was slowly cooled to room temperature. The white gel-like solid which deposited was collected in a sintered glass funnel and washed with several portions of EtOH. Vacuum oven drying at 40° C. for several hours gave a white solid, m.p., 132°-134° C.

b. 2S,3S-[(Phenylmethoxy)carbonyl]-L-valyl-N-[3-(1,1,1-trifluoro-2-hydroxy-4-methylpentyl)]-L-prolinamide
(Formula VIIb, $R^1$=CH(CH$_3$)CH$_3$, $R^2$=CH(CH$_3$)CH$_3$, $R^3$=$\phi$CH$_2$, $R^4$=H, A=OCO, n=1)

Acid prepared according to Example 5b (1.00 g, 2.87 mmol) was dissolved in dry THF (16 ml) under $N_2$ in a 50-ml, 3-necked, round-bottom flask equipped with a thermometer, $N_2$ inlet, septum and a magnetic stir bar. NMM (0.34 ml, 3.09 mmol) was added and the resultant stirred solution was cooled to an internal temperature of $-35°$. Isobutyl chloroformate (0.37 ml, 2.85 mmol) was added over 2 min, never allowing the internal temperature to rise above $-35°$. The reaction was stirred for 1 hr at $-45°$ to $-35°$. The D-tartarate salt from Example 6a (0.92 g, 2.86 mmol) in a mixture of THF (5 ml) and DMSO (2 ml) was treated with NMM (0.68 ml) and the cloudy solution was added to the reaction mixture at such a rate that the temperature was kept below $-40°$. The reaction was stirred at $-45°$ to $-15°$ for 1 hr before it was allowed to warm to room temperature overnight. The mixture was diluted with CHCl$_3$ and then washed ($H_2O$, sat'd aq NaHCO$_3$), dried (Na$_2$SO$_4$), and concentrated to give the title product (1.15 g, 80%) as a white solid. The $^1$H-NMR spectrum of this material in DMSO-d$_6$ exhibited a doublet at $\delta$6.43, which is the appropriate chemical shift of the alcohol proton in material with the assigned relative configuration.

c.
3S(orR)-Phenylmethoxycarbonyl-L-valyl-N-[3-(1,1,1-trifluoro-4-methyl-2-oxopentyl)]-L-prolinamide
(Formula Ib, $R^1$=CH(CH$_3$)CH$_3$, $R^2$=CH(CH$_3$)CH$_3$, $R^3$=$\phi$CH$_2$, $R^4$=H, A=OCO, n=1).

A portion of the alcohol generated in Example 6b (0.25 g, 0.5 mmol) was dissolved in $CH_2Cl_2$ and treated with Dess-Martin periodinane (0.42 g, 0.99 mmol) in a single portion. TFA (0.08 ml, 1.04 mmol) was added, and the slightly turbid mixture was allowed to stir overnight. A white suspension formed in the reaction mixture. Starting material was substantially absent as demonstrated by TLC. Water containing $Na_2S_2O_3$ (0.78 g) and $NaHCO_3$ (0.42 g) was added and stirred with the reaction mixture. When the organic layer eventually was cleared of the white solid suspension, it was separated from the aqueous phase. The organic layer was washed (sat'd aq $NaHCO_3$), dried ($Na_2SO_4$), and concentrated to give an oil. This material redissolved and was concentrated from $Et_2O$/hexane to give a white solid (0.21 g, 84% yield). Recrystallization from hot $Et_2O$/hexane yielded a substantially pure sample of the title compound as a substantially pure isomer which exhibited a single peak on HPLC with a retention time identical with that of an authentic sample of the title product prepared as described in Example 117; HPLC, $t_R=5.65$, Col A, $H_2O:CH_3CH$ (55:45), FR=2.0

EXAMPLE 7

1-[2-(Tricyclo[3.3.1.1$^{3,7}$]dec-1-yl)ethoxycarbonyl]-N-[3(RS)-3-(4-methyl-1,1,1-trifluoro-2-oxopentyl)]-L-prolinamide a. 4-Nitrophenyl 2-[tricyclo(3.3.1.1$^{3,7}$)dec-1-yl]-ethyl carbonate To a solution of p-nitrophenyl chloroformate (1.17 g, 5.82 mmol) in $Et_2O$ (25 ml) at 0° C. was added pyridine (5 ml) followed by addition of 2-(1-adamantyl)ethanol (1.00 g, 5.54 mmol) in $Et_2O$ (20 ml) dropwise over 1 hr. The resulting mixture was stirred at room temperature for 12 hr. and partitioned between $H_2O$ and $Et_2O$. The ethereal layer was washed with 5% aqueous HCl, pH 7.0 phosphate buffer, dried over $MgSO_4$, filtered and the solvents removed under vacuum. The crude product was purified by flash chromatography on silica gel eluting with EtOAc:hexane (5:95) to give the product (1.10 g) as a white powder; TLC, $R_f=0.29$, silica gel, EtOAc:hexane (5:95).

b. 1-[2-(Tricyclo[3.3.1.1$^{3,7}$]dec-1-yl)ethoxycarbonyl]-N-[2(RS),3(SR)-3-(4-methyl-1,1,1-trifluoro-2-hydroxypentyl)]-L-prolinamide A solution of the product of Example 7a (731.0 mg, 2.98 mmol), a product using the procedure of Example 2b (500 mg, 1.80 mmol) and $K_2CO_3$ (2.57 g, 18.6 mmol) in DMF (50 ml) was stirred at room temperature for 18 hr., filtered and the solvent removed under vacuum. The residue was taken up in EtOAc, washed with 3 portions of 10% aqueous NaOH, dried over solid $K_2CO_3:Na_2SO_4$ (10:90), filtered and the solvent removed at reduced pressure. The crude product was chromatographed on silica gel eluting with MeOH:CHCl$_3$ (1:99). The resulting solid was washed with hexane to give the product (340 mg) as a white solid; HPLC, $t_R=5.86$, 6.38, Zorbax ® ODS analytical column, Flow rate=2 ml/min, CH$_3$CN:H$_2$O:TFA (70:30:0.1)

c. 1-[2-(Tricyclo[3.3.1.1$^{3,7}$]dec-1-yl)ethoxycarbonyl]-N-3(RS)-[3-(4-methyl-1,1,1-trifluoro-2-oxopentyl)]-L-prolinamide To a solution of oxalyl chloride (1.09 g, 8.60 mmol) in dry $CH_2Cl_2$ (15 ml) cooled to $-43°$ C. was added DMSO (1.37 g, 17.3 mmol) in dry $CH_2Cl_2$ (10 ml) dropwise over 15 min. The solution was stirred for 10 min. and the product of Example 7b (340 mg, 0.72 mmol) was added in the same manner over 30 min. After stirring the solution at $-43°$ C. for an additional 1 hr, TEA (4.80 ml, 34.5 mmol) was slowly added and the solution allowed to warm slowly to room temperature and was stirred for 2 hr. The solution was diluted with $CH_2Cl_2$, washed with 10% aqueous HCl, 5% aqueous NaOCl, dried over solid $K_2CO_3:Na_2SO_4$ (10:90), filtered and the solvent removed under vacuum. The crude product was purified by 2 successive flash chromatographies on silica gel eluting with MeOH:CHCl$_3$ (0.1:99.9) and EtOAc:hexane (1:5), respectively, to give the product (130 mg) as a white solid; TLC, $R_f=0.50$, silica gel, MeOH:CHCl$_3$ (5:95); HPLC, $t_R=5.31$, Zorbax ® ODS analytical column, flow rate=2 ml/min, CH$_3$CN:H$_2$O:TFA (70:30:.01).

Analysis calculated for: $C_{24}H_{35}N_2F_3O_4 \cdot 0.25H_2O$: C, 60.43; H, 7.50; N, 5.87. Found: C, 60.50; H, 7.45; N, 5.74.

EXAMPLE 8

3(RS)-1-(4-Phenylbutylcarbonyl)-N-[3-(4-methyl-1,1,1-trifluoro-2-oxopentyl)]-L-prolinamide a. 2(RS),3(SR)-1-(4-Phenylbutylcarbonyl)-N-[3-(4-methyl-1,1,1-trifluoro-2-hydroxypentyl)]-L-prolinamide A solution of 5-phenylvaleric acid (0.330 g, 1.86 mmol) and N-methylmorpholine (0.280 g, 2.79 mmol) in THF (100 ml) was cooled to $-15°$ C. A solution of isobutyl chloroformate (0.280 g, 2.05 mmol) in THF (5 ml) was added dropwise and the mixture was stirred at $-15°$ C. for 10 min., after which the temperature was lowered to $-40°$ C. and a solution of a product made using the procedure of Example 2b (0.500 g, 1.86 mmol) in THF (25 ml) was added dropwise. The mixture was stirred for 1 hr at $-40°$ C. and overnight at room temperature. The mixture was filtered and the filtrate concentrated under vacuum. The crude product was purified by flash chromatography on silica gel eluting with MeOH:CHCl$_3$ (3:97) to give the product (0.60 g) as a white solid; TLC, $R_f=0.40$–0.51, silica gel, MeOH:CHCl$_3$ (3:97).

b. 3(RS)-1-(4-Phenylbutylcarbonyl)-N-[3-(4-methyl-1,1,1-trifluoro-2-oxopentyl)]-L-prolinamide A solution of DMSO (4.22 g, 54.0 mmol) in dry $CH_2Cl_2$ (80 ml) was added dropwise over 10 min to a pre-cooled ($-60°$ C.), stirred solution of oxalyl chloride (3.43 g, 27.0 mmol) in $CH_2Cl_2$ (10 ml) under a nitrogen atmosphere. The temperature never exceeded $-55°$ C. during the addition. The mixture was stirred at $-60°$ C. for 15 min. and a solution of the product of Example 8a (0.580 g, 1.35 mmol) in $CH_2Cl_2$ (100 ml) was added dropwise over 10 min. at $-60°$ C. The reaction mixture was stirred at $-60°$ C. for 1 hr. Diisopropylethylamine (6.98 g, 54.0 mmol) was added dropwise over 10 min at $-60°$ C. The reaction mixture was stirred for 1 hr as it warmed to room temperature. The reaction mixture was washed successively with two portions of 1N aqueous HCl and brine, and concentrated under vacuum to give the crude product (0.85 g) as an orange syrup. The crude product was purified by three successive flash chromatographies on silica gel eluting respectively with, 1) MeOH:CHCl$_3$ (3:97), 2) MeOH:CHCl$_3$ (3:97), and 3) $Et_2O$: hexane (90:10) to give the product (319 mg) as a white foam; TLC, $R_f$=0.33– 0.40, silica gel, Et$_2$O: hexane (90:10); HPLC, $t_R$=17.93, 18.55, Zorbax® ODS analytical column, H$_2$O:CH$_3$CN (55:45), flow rate=2 ml/min.

Analysis calculated for: C$_{22}$H$_{29}$N$_2$O$_3$F$_3$.1.25H$_2$O: C, 58.85; H, 7.07; N, 6.24. Found: C, 58.91; H, 6.83; N, 6.13.

EXAMPLE 9

3
(RS)-1-[(Phenylmethoxy)carbonyl]-N-[3-(4-methyl-1,1,1-trifluoro-2-oxopentyl)]-L-prolinamide A solution of dimethylsulfoxide (0.890 g, 11.4 mmol) and dry methylene chloride (5 ml) was added dropwise to a stirred solution of oxalyl chloride (0.75 g, 5.9 mmol) and dry methylene chloride (5 ml) at −60° C. under nitrogen. The reaction mixture was allowed to warm to −25° C., then a solution of a product made using the process of Example 2a (0.200 g, 0.497 mmol) and dry methylene chloride (5 ml) was added. The resultant mixture was stirred at −25° C. for 0.5 hr. Triethylamine (1.94 g, 19.2 mmol) was added and the reaction mixture was allowed to warm to room temperature. The reaction mixture was filtered. The filtrate was evaporated. The residue was dissolved in chloroform. The chloroform solution was washed successively with 1N aqueous HCl, then brine and dried over Na$_2$SO$_4$. The solution was filtered. The solvent was removed under vacuum to give the crude product (0.147 g). The crude product was purified by flash chromatography on silica gel with an eluent of CHCl$_3$: MeOH (97:3) to give the product (0.11 g); TLC, $R_f$=0.25, CHCl$_3$:EtOAc (90:10).

Analysis calculated for: C$_{19}$H$_{23}$F$_3$N$_2$O$_4$. 1.5H$_2$O: C, 53.39; H, 6.13; N, 6.55. Found: C, 53.55; H, 5.78; N, 6.56.

EXAMPLE 10

2(RS),3(SR)-L-Valyl-N-[3-(4-methyl-1,1,1-trifluoro-2-hydroxypentyl)]-L-prolinamide a. N-[(Phenylmethoxy)carbonyl]-L-valyl-L-proline methyl ester The procedure of Example 3a was repeated.

b. N-[(Phenylmethoxy)carbonyl]-L-valyl-L-proline

The procedure of Example 3b was repeated using the material from Example 10a.

c. 2-Methyl-1-nitropropane

The procedure of Example 1a was repeated.

d.
2(RS),3(SR)-4-Methyl-3-nitro-1,1,1-trifluoro-2-pentanol

The procedure of Example 1b was repeated using the material from Example 10c.

e.
2(RS),3(SR)-3-Amino-4-methyl-1,1,1-trifluoro-2-pentanol hydrochloride salt

The procedure of Example 1c was repeated using the material from Example 10d.

f. 2
(RS),3(SR)-[(Phenylmethoxy)carbonyl]-L-valyl-N-[3-(4-methyl-1,1,1-trifluoro-2-hydroxypentyl -L-prolinamide The process of Example 3c was repeated using the compounds from Examples 10b and 10e.

g. 2
(RS),3(SR)-L-Valyl-N-[3-(4-methyl-1,1,1-trifluoro-2-hydroxypentyl)]-L-prolinamide The process of Example 3d was repeated using the compound from Example 10f.

EXAMPLE 11

3(RS)-[(Phenylmethoxy)carbonyl]-L-valyl-N-[3-(4-methyl-1,1,1-trifluoro-2-oxopentyl)]-L-prolinamide a.-f. Steps a-f were repeated as explained in Examples 10a-f g.
3(RS)-[(Phenylmethoxy)carbonyl]-L-valyl-N-[3-(4-methyl-1,1,1-trifluoro-2-oxopentyl)]-L-prolinamide A solution of DMSO (12.46 g, 159.50 mmol) in dry CH$_2$Cl$_2$ (12 ml) was added dropwise over 10 min. to a pre-cooled (−60° C.), stirred solution of oxalyl chloride (10.12 g, 79.75 mmol) in CH$_2$Cl$_2$ (160 ml) under a nitrogen atmosphere. The temperature of the reaction never exceeded −50° C. during the addition. A solution of the alcohol in Example 11f (2.00 g, 3.99 mmol) in CH$_2$Cl$_2$ (160 ml) was added dropwise over 10 min. at −60° C. The reaction mixture was stirred at −60° C. for 1 hour. Diisopropylethylamine (20.62 g, 159.50 mmol) was added dropwise over 10 min. at −60° C. The reaction mixture was stirred for 1 hr. as it warmed to room temperature. The reaction mixture was washed with 1N aqueous HCl, then brine, and then concentrated under vacuum to give the crude product as an orange syrup (2.76 g). The crude product was purified with three successive flash chromatographies on silica gel eluting respectively with 1) ether:hexane (80:20), 2) MeOH:CHCl$_3$ (2.5:97.5), 3) MeOH:CHCl$_3$ (2.5: 97.5) to give the product as a white foam (0.88 g); TLC, $R_f$=0.45, silica gel, MeOH:CHCl$_3$ (3:97); HPLC, $t_R$=6.45, 11.10, Zorbax® ODS analytical column, H$_2$O: CH$_3$CN (55:45) with 0.1% trifluoroacetic acid, flow rate=2 ml/min.

Analysis calculated for: C$_{24}$H$_{32}$N$_3$O$_5$F$_3$.0.5 H$_2$O: C, 56.68; H, 6.54; N, 8.26. Found: C, 56.58; H, 6.52; N, 8.21.

EXAMPLE 12

3(RS)-[2-(2-Oxopyrrolidinyl)ethoxycarbonyl]-L-valyl-N-[3-(4-methyl-1,1,1-trifluoro-2-oxypentyl)]-L-prolinamide a. 4-Nitrophenyl-2-(2-oxopyrrolidinyl)ethyl carbonate N-(2-hydroxyethyl)pyrrolidone (3.00 g, 23.2 mmol) was dissolved in diethyl ether (20 ml) under a nitrogen atmosphere and stirred at room temperature. A solution of p-nitrophenyl chloroformate (4.68 g, 23.2 mmol) in diethyl ether (25 ml) was added dropwise to the mixture over 2 hr. The mixture was stirred for an additional 2 hr. at room temperature. The mixture was concentrated under vacuum to give the crude product (7.90 g). The crude product was purified by flash chromatography on silica gel with MeOH:CHCl$_3$ (5:95) to give the product as a white powder (4.62 g); TLC, $R_f$=0.51, silica gel, MeOH:CHCl$_3$ (3:97).

b.
2(RS),3(SR)-[2-(2-Oxopyrrolidinyl)ethoxycarbonyl]-L-valyl-N-[3-(4-methyl-1,1,1-trifluoro-2-hydroxypentyl)]-L-prolinamide Potassium carbonate (2.820 g, 40.80 mmol) was added to a solution of ethyl-2-pyrrolidone-p-nitrophenyl carbonate (1.20 g, 4.08 mmol) and a product made using the procedure of Example 3d (1.50 g, 4.08 mmol) in DMF (100 ml) at room temperature under a nitrogen atmosphere. The reaction was stirred overnight. The reaction mixture was diluted with EtOAc and the excess $K_2CO_3$ was filtered. The filtrate was concentrated under vacuum to give a residue which was dissolved in EtOAc and washed successively with aqueous 10% $NaHCO_3$, water, aqueous 5% citric acid, and brine. The organic phase was dried over $Na_2SO_4$, filtered and concentrated under vacuum to give the crude alcohol. The alcohol was purified using flash chromatography on silica gel with $MeOH:CHCl_3$ (5:95) to give the product (0.72 g); TLC, $R_f=0.46$, silica gel, MeOH: $CHCl_3$ (7:93).

c.
3(RS)-[2-(2-Oxopyrrolidinyl)ethoxycarbonyl]-L-valyl-N-[3-(4-methyl-1,1,1-trifluoro-2-oxypentyl)]-L-prolinamide A solution of DMSO (4.310 g, 55.20 mmol) in dry $CH_2Cl_2$ (6 ml) was added dropwise over 10 min. to pre-cooled ($-60°$ C.), stirred solution of oxalyl chloride (3.500 g, 27.60 mmol) in $CH_2Cl_2$ (80 ml) under a nitrogen atmosphere. The temperature of the reaction never exceeded $-50°$ C. during the addition. A solution of the alcohol from Example 12b (0.720 g, 1.38 mmol) in $CH_2Cl_2$ (80 ml) was added dropwise over 10 min. at $-60°$ C. The reaction mixture was stirred at $-60°$ C. for 1 hr. A solution of diisopropylethyl amine (7.13 g, 55.2 mmol) in $CH_2Cl_2$ (50 ml) was added dropwise over 10 min. at $-60°$ C. The reaction mixture was stirred for 1 hr. as it warmed to room temperature. The reaction mixture was washed with 1N aqueous HCl and brine and then concentrated under vacuum to give the crude product as an orange syrup. The crude product was purified by flash chromatography on silica gel with $MeOH:CHCl_3$ (5:95) to give the product as white foam (0.43 g) ; TLC, $R_f=0.33$, silica gel, $MeOH:CHCl_3$ (5:95); HPLC, $t_R=3.50$, 4.63, Zorbax ® ODS analytical column, $H_2O:CH_3CN$ (55:45), flow rate=1 ml/min.

Analysis calculated for: $C_{23}H_{35}N_4O_6F_3 \cdot H_2O$: C, 51.29; H, 6.92; N, 10.40. Found: C, 51.20, H, 6.86; N, 10.03.

EXAMPLE 13

3(RS)-[2-Methoxycarbonyl)ethylcarbonyl]-L-valyl-N-[3-(4-methyl-1,1,1-trifluoromethyl-2-oxopentyl)]-L-prolinamide a. N-Benzyloxycarbonyl-L-valyl-L-proline t-butyl ester A solution of N-benzyloxycarbonyl-L-valine (56.25 g, 0.244 mol) and HOBT (60.67 g, 0.45 mol) in DMF (565 ml) was cooled to 5° C. DCC (50.89 g, 0.247 mol) was added in one portion. The mixture was stirred an additional 15 min. at 5° C. and then L-proline t-butyl ester (38.36 g, 0.224 mol) was added. The mixture was stirred an additional 2 hr. at 5° C. then for 48 hr. at room temperature. The mixture was filtered and concentrated under vacuum. The oily residue was dissolved in EtOAc (1 liter) and washed successively with 20% aqueous citric acid, saturated aqueous $NaHCO_3$ and brine. The organic phase was dried over $Na_2SO_4$, filtered and concentrated under vacuum to afford the product (92.0 g) as a white foam; TLC, $R_f=0.9$, silica gel, $CHCl_3:EtOAc$ (85:15).

b. L-Valyl-L-proline t-butyl ester

A mixture of the product of Example 13a (92.0 g, 0.227 mol) and 10% Pd/C (10 g) in EtOH (1 liter) was hydrogenated on a Parr shaker for 6 hr. at 413,793.1 Pascals, 60 psi at room temperature. The mixture was filtered through Celite ® and concentrated under vacuum to afford the product (62 g) as a viscous yellow oil; TLC, $R_f=0.3$, silica gel, $MeOH:CHCl_3$ (10:90).

c.
N-[2-(Methoxycarbonyl)ethylcarbonyl]-L-valyl-L-proline-1,1-dimethylethyl ester 1N aqueous NaOH (8.0 ml) was added to a precooled (0° C.) solution of the product of Example 13b (2.1 g, 7.8 mmol) in $CH_2Cl_2$ (60 ml). The mixture was stirred and 3-carbomethoxypropionyl chloride (0.96 ml, 7.8 mmol) was added. The reaction was stirred vigorously for 15 min. at 0° C. The solution was removed from the ice bath, diluted with $H_2O$ (30 ml) and acidified with 1N aqueous HCl. The organic layer was separated and the aqueous layer was extracted with $CH_2Cl_2$. The organic layers were combined, dried over $Na_2SO_4$, filtered, and concentrated under vacuum. The resulting residue was purified by flash chromatography on a column of silica gel eluting with $Et_2O$ followed by EtOAc to give the product (2.68 g); TLC, $R_f=0.28$, silica gel, $Et_2O$.

d.
N-[2-(Methoxycarbonyl)ethylcarbonyl]-L-valyl-L-proline

Trifluoroacetic acid (11.0 ml, 143 mmol) was added to a solution of the product of Example 13c (2.68 g, 6.98 mmol) in $CH_2Cl_2$ (11 ml). The mixture was stirred for 4 hr. and concentrated under vacuum to give the product (2.13 g) which was used without further purification.

e.
2(RS),3(SR)-[2-(Methoxycarbonyl)ethylcarbonyl]-L-valyl-N-[3-(4-methyl-1,1,1-trifluoro-2-hydroxypentyl)]-L-prolinamide Isobutylchloroformate (0.85 ml, 6.5 mmol) was added to a pre-cooled ($-15°$ C.) solution of N-methylmorpholine (0.71 ml, 6.5 mmol) and the product of Example 13d (2.13 g, 6.5 mmol) in THF (50 ml). The reaction was stirred for 10 min. and the temperature reduced to $-50°$ C. A suspension of N-methylmorpholine (0.71 ml, 6.5 mmol) and a product made using the procedure of Example 1c (1.39 g, 6.5 mmol) in THF (50 ml) was added in one portion and the reaction stirred overnight as it warmed to room temperature. The reaction was filtered and the filtrate concentrated under vacuum. The residue was taken up in EtOAc and washed successively with 1N aqueous HCl and brine. The organic layer was dried over $Na_2SO_4$, filtered and concentrated under vacuum. The resulting residue was purified by flash chromatography on silica gel eluting with $MeOH:CHCl_3$ (5:95) to give the product (1.92 g); TLC, $R_f=0.24$, silica gel, $MeOH:CHCl_3$ (5:95).

f.
3(RS)-[2-(Methoxycarbonyl)ethylcarbonyl]-L-valyl-N-[3-(4-methyl-1,1,1-trifluoro-2-oxopentyl)]-L-prolinamide A solution of DMSO (11.2 ml, 0.158 mol) in CH$_2$Cl$_2$ (12 ml) was added slowly to a pre-cooled (−60° C.) solution of oxalyl chloride (6.9 ml, 0.079 mol) in CH$_2$Cl$_2$ (160 ml). A solution of the product of Example 13e (1.90 g, 3.95 mmol) in CH$_2$Cl$_2$ (160 ml) was added to the reaction mixture and stirred for 1 hr. at −60° C. Diisopropylethylamine (28.0 ml, 0.158 mol) was added slowly and the reaction was allowed to warm to ambient temperature. The solution was washed with 1N aqueous HCl (2×80 ml) and brine. The organic layer was dried over Na$_2$SO$_4$, filtered and concentrated to give the crude product (3.5 g). The product was purified by filtration through silica gel with EtOAc followed by flash chromatography on silica gel using MeOH: CHCl$_3$ (5:95) to give the product (1.49 g); TLC, R$_f$=0.31, silica gel, MeOH:CHCl$_3$ (5:95); Diagnostic $^1$H NMR shifts (CD$_3$SOCD$_3$, 250 MHz): 0.9, m, 12H; 3.54, s, 3H; 3.54–3.68, m, 2H; 4.34, m, 1H; 4.40, m, 1H; 4.48 , dd, ½H; 4.58 , dd, ½H; 8.1 , d, 1H; 8.58 , dd, 1H.

EXAMPLE 14

3(RS)-[(2-Carboxyethyl)carbonyl]-L-valyl-N-[3-(4-methyl-1,1,1-trifluoro-2-oxopentyl)]-L-prolinamide 1N aqueous NaOH (0.92 ml) was added to a solution of the product of Example 13f (0.20 g, 0.42 mmol) in MeOH (10 ml) and the reaction was stirred overnight at ambient temperature. 1N aqueous HCl (1 ml) was added and the reaction mixture was concentrated under vacuum to remove MeOH. The aqueous solution remaining was extracted with EtOAc and the organic layer was washed with brine, dried over Na$_2$SO$_4$, filtered and concentrated under vacuum to give the product (0.18 g); TLC, R$_f$=0.2, silica gel, MeOH: CHCl$_3$:TFA (5:94:1); HPLC, t$_R$=2.9, 5.86, Applied Science Absorbosphere ® C8, 4.6 mm×10 cm, CH$_3$CN:H$_2$O: TFA (20:80:0.1), flow rate=1.6 ml/min.

EXAMPLE 15

3(RS)-[(4-(Ethoxycarbonyl)phenyl)aminocarbonyl]-L-valyl-N-[3-(4-methyl-1,1,1-trifluoro-2-oxopentyl)]-L-prolinamide a. 2 (RS),3(SR)-[(4-Ethoxycarbonylphenyl)aminocarbonyl]-L-valyl-N-[3-(4-methyl-1,1,1-trifluoro-2-hydroxypentyl)]-L-prolinamide A solution of ethyl 4-isocyanatobenzoate (0.86 g, 4.5 mmol) in CHCl$_3$ (2 ml) was added dropwise to a solution of a product made using the procedure of Example 3d (1.65 g, 4.5 mmol) in CHCl$_3$ (20 ml) and the reaction was stirred overnight at ambient temperature. The reaction was concentrated under vacuum to give the crude product. The product was purified by flash chromatography on silica gel using MeOH:CHCl$_3$ (2.5: 97.5) and MeOH:CHCl$_3$ (5:95) as eluents to give the product (1.76 g); TLC, R$_f$=0.34, silica gel, MeOH: CHCl$_3$ (5:95).

b. 3 (RS)-[(4-Ethoxycarbonylphenyl)aminocarbonyl]-L-valyl-N-[3-(4-methyl-1,1,1-trifluoro-2-oxopentyl)]-L-prolinamide A solution of DMSO (4.5 ml, 63 mmol) in CH$_2$Cl$_2$ (5 ml) was added slowly to a pre-cooled (−60° C.) solution of oxalyl chloride (2.75 ml, 31.5 mmol) in CH$_2$Cl$_2$ (60 ml). The reaction was stirred for 15 min. at −60° C. A solution of the product of Example 15a (1.76 g, 3.15 mmol) in CH$_2$Cl$_2$ (60 ml) was added to the reaction mixture and stirred for 1 hr. at −60° C. Diisopropylethylamine (11 ml, 63 mmol) was added slowly and the reaction was allowed to warm to ambient temperature. The solution was washed with 1N aqueous HCl (2×60 ml) and brine. The organic layer was dried over Na$_2$SO$_4$, filtered and concentrated under vacuum to give the crude product (2.3 g). The product was purified by flash chromatography on silica gel using a step gradient of CHCl$_3$, MeOH:CHCl$_3$ (2.5:97.5) and MeOH:CHCl$_3$ (5:95) to give the product (0.91 g); TLC, R$_f$=0.42, silica gel, MeOH:CHCl$_3$ (5:95); HPLC, t$_R$= 6.77, 11.27, Zorbax ® ODS analytical column, CH$_3$CN:H$_2$O (45:55), flow rate=2 ml/min.

EXAMPLE 16

3(RS)-[(4-Carboxyphenyl)aminocarbonyl]-L-valyl-N-[3-(4-methyl-1,1,1-trifluoro-2-oxopentyl)]-L-prolinamide 1N aqueous NaOH (1 ml) was added to a solution of the product of Example 15b (0.48 g, 0.86 mmol) in MeOH:H$_2$O (8 ml:7 ml). The reaction was stirred for 3 hr., additional 1N aqueous NaOH was added (1 ml) and the reaction was stirred overnight at ambient temperature. 1N aqueous HCl (2.5 ml) was added and the methanol was removed under vacuum. H$_2$O (10 ml) was added to the residue and extracted with EtOAc (2×50 ml). The combined organic layers were washed with brine, dried over Na$_2$SO$_4$, filtered and concentrated under vacuum to give the product (0.42 g); TLC, R$_f$=0.17, silica gel, MeOH:CHCl$_3$:AcOH (5:94:1); HPLC, t$_R$=2.38, 2.78, Zorbax ® ODS analytical column, CH$_3$CN:H$_2$O (30:70), flow rate=1 ml/min.

EXAMPLE 17

3(RS)-[(4-Phenylbutyl)carbonyl]-L-valyl-N-[3-(4-methyl-1,1,1-trifluoro-2-oxopentyl)]-L-prolinamide a. 2 (RS),3(SR)-[(4-Phenylbutyl)carbonyl]-L-valyl-N-[3-(4-methyl-1,1,1-trifluoro-2-hydroxypentyl)]-L-prolinamide DCC (0.906 g, 4.4 mmol) was added to a solution of 5-phenylvaleric acid (0.728 g, 4.08 mmol), a product made using the procedure of Example 3d (1.5 g, 4.08 mmol) and HOBT (1.19 g, 8.8 mmol) in THF (75 ml) at 0° C. The mixture was stirred and allowed to slowly warm to room temperature overnight. The mixture was concentrated under vacuum and the resulting residue was taken up in CHCl$_3$ (60 ml) and washed successively with 20% aqueous citric acid (30 ml), H$_2$O (30 ml), 5% aqueous NaHCO$_3$ (30 ml) and brine (30 ml). The organic phase was collected, dried over Na$_2$SO$_4$, filtered and concentrated under vacuum to give the crude product (2.0 g). Purification by flash chromatography on silica gel eluting with MeOH:CHCl$_3$ (5:95) gave the product (1.0 g) as a white foam; TLC, R$_f$=(0.5–0.55), silica gel, MeOH: CHCl$_3$ (5:95).

b.
3(RS)-[(4-Phenylbutyl)carbonyl]-L-valyl-N-[3-(4-methyl-1,1,1-trifluoro-2-oxopentyl)]-L-prolinamide A solution of DMSO (3.4 ml, 48 mmol) in dry CH$_2$Cl$_2$ (4 ml) was added dropwise to a stirred solution of oxalyl chloride (2.10 ml, 24 mmol) in dry CH$_2$Cl$_2$ (50 ml) cooled to −60° C. under a N$_2$ atmosphere. The solution was stirred at −60° C. for 15 min. A solution of the product of Example 17a (1.00 g, 1.89 mmol) in dry CH$_2$Cl$_2$ (30 ml) was added slowly, keeping the solution temperature below −50° C. The mixture was stirred at (−50° C.) for 1 hr. Diisopropylethylamine (8.48 ml, 48 mmol) was added dropwise and the reaction mixture was allowed to warm slowly to room temperature. The reaction mixture was washed successively with 1N aqueous HCl and brine. The organic phase was collected, dried with Na$_2$SO$_4$, filtered and concentrated under vacuum to give the crude ketone. The ketone was purified by 3 successive flash chromatographies with silica gel and eluents of (MeOH:CHCl$_3$ (5:95), CHCl$_3$ (100%)—MeOH:CHCl$_3$ (3:97), and Et$_2$O (100%)—MeOH:Et$_2$O (10:90) to give the final product (0.2 g) as a white waxy solid; HPLC, t$_R$=6.80, 8.90, Zorbax ® ODS column; H$_2$O:CH$_3$CN:TFA (40:60:0.1), flow rate=0.75 ml/min.

Analysis calculated for: C$_{27}$N$_3$O$_4$F$_3$H$_{38}$.0.5 H$_2$O: C, 60.65; H, 7.35; N, 7.85. Found: C, 60.68; H, 7.30; N, 7.67.

EXAMPLE 18

3(RS)-2-[2-(Tricyclo[3.3.1.1$^{3,7}$]dec-1-yl)ethoxycarbonyl]-L-valyl-N-[3-(4-methyl-1,1,1-trifluoro-2-oxopentyl)]-L-prolinamide a. 4-Nitrophenyl 2-(tricyclo[3.3.1.1$^{3,7}$]dec-1-yl)ethyl carbonate

A product was obtained using the process of Example 7a.

b.
2(RS),3(SR)-[2(Tricyclo[3.3.1.1$^{3,7}$]dec-1-yl)ethoxycarbonyl]-L-valyl-N-[3-(4-methyl-1,1,1-trifluoro-2-hydroxypentyl)]- L-prolinamide A solution of the product of Example 18a (0.758 g, 2.19 mmol), a product made using the procedure of Example 3d (0.768 g, 2.09 mmol) and K$_2$CO$_3$ (2.89 g, 20.9 mmol) in DMF (75 ml) was stirred at room temperature for 18 hr., filtered, and the solvents removed under vacuum. The residue was diluted with ethyl acetate, washed with 3 portions of 10% aqueous NaOH and brine, dried over solid K$_2$CO$_3$:Na$_2$SO$_4$ (10:90), filtered and the solvents removed at reduced pressure. The crude product was purified by flash chromatography on silica gel, eluting with MeOH:CHCl$_3$ (2:98) to give the product (0.965 g) as a white foam; TLC, R$_f$=0.14 and 0.18, silica gel, MeOH:CHCl$_3$ (2:98).

c.
3(RS)-[2-(Tricyclo[3.3.1.1$^{3,7}$]dec-1-yl)ethoxycarcarbonyl]-L-valyl-N-[3-(4-methyl-1,1,1-trifluoro-2-oxopentyl)]-L-prolinamide To a solution of oxalyl chloride (2.14 g, 16.8 mmol) in dry CH$_2$Cl$_2$ (30 ml) cooled to −43° C. was added DMSO (2.66 g, 33.6 mmol) in CH$_2$Cl$_2$ (20 ml) dropwise over 1 hr., followed by addition of the product of Example 18b (0.965 g, 1.68 mmol) in the same manner over 30 min. After stirring the solution at −43° C. an additional 1 hr., triethylamine (8.50 g, 84.0 mmol) was added and the solution allowed to warm slowly to room temperature. The solution was diluted with CH$_2$Cl$_2$, washed with 5% aqueous HCl, 5% aqueous NaOCl, dried over MgSO$_4$, filtered and the solvent removed under vacuum. The crude product was purified by flash chromatography on silica gel eluting with CHCl$_3$ after pretreating silica gel with MeOH:CHCl$_3$ (1:99) to give the product (410 mg) as a white foam; TLC, R$_f$=0.39, silica gel, MeOH:CHCl$_3$ (2:98); HPLC t$_R$=8.12 and 10.75, Zorbax ® ODS column, flow rate=1.5 ml/min., CH$_3$CN:H$_2$O:TFA (70:30: 0.1).

Analysis calculated for: C$_{29}$H$_{44}$N$_3$F$_3$O$_5$.0.75 H$_2$O: C, 59.52; H, 7.83; N, 7.18. Found: C, 59.48; H, 7.70; N, 7.17.

EXAMPLE 19

3(RS)-[(2-Methoxyethoxy)ethoxycarbonyl]-L-valyl-N-[3-(4-methyl-1,1,1-trifluoro-2-oxopentyl)]-L-prolinamide a. 2-(2-Methoxyethoxy)ethyl 4-nitrophenyl carbonate

To a solution of p-nitrophenyl chloroformate (2.00 g, 9.92 mmol) in Et$_2$O (50 ml) at 0° C. was added pyridine (8 ml), followed by addition of 2-(2-methoxyethoxy)ethanol (1.14 g, 9.45 mmol) in Et$_2$O (25 ml) dropwise over 1 hr. The resulting mixture was stirred at room temperature for 12 hr. and partitioned between H$_2$O and Et$_2$O. The ethereal layer was washed with 5% aqueous HCl, pH 7.0 phosphate buffer, dried over MgSO$_4$, filtered and the solvents removed under vacuum. The crude product was purified by flash chromatography on silica gel eluting with EtOAc:hexane (30:70) to give the product (1.30 g) as a clear colorless oil; TLC, R$_f$=0.11, silica gel, EtOAc:hexane (30:70).

b.
2(RS),3(SR)-[(2-Methoxyethoxyethoxy)carbonyl]-L-valyl-N-[3-(4-methyl-1,1,1-trifluoro-2-hydroxypentyl)]-L-prolinamide A solution of the product from Example 19a (1.11 g, 3.90 mmol), a product made using the procedure of Example 3d (1.37 g, 3.72 mmol), and K$_2$CO$_3$ (5.14 g, 37.2 mmol) in DMF (100 ml) was stirred at room temperature for 18 hr., filtered and the solvents removed under vacuum. The residue was taken up in ethyl acetate, washed with 3 portions of 10% aqueous NaOH and brine, dried over solid K$_2$CO$_3$:Na$_2$SO$_4$ (10:90), filtered and the solvents removed under vacuum. The crude product was purified by flash chromatography on silica gel, eluting with EtOAc after pretreating the silica gel with TEA:hexane (1:9) to give the product (1.13 g) as a clear colorless glass; TLC, R$_f$=0.43 and 0.48, silica gel, MeOH:CHCl$_3$ (1:9).

Analysis calculated for: C$_{22}$H$_{38}$N$_3$O$_7$F$_3$: C, 51.45; H, 7.45; N, 8.18. Found: C, 51.48, H, 7.35; N, 8.01.

c.
3(RS)-[(2-Methoxyethoxy)ethoxycarbonyl]-L-valyl-N-[3-(4-methyl-1,1,1-trifluoro-2-oxopentyl)]-L-prolinamide To a solution of oxalyl chloride (3.26 g, 2.57 mmol) in dry CH$_2$Cl$_2$ (70 ml) cooled to −43° C. was added DMSO (4.07 g, 51.4 mmol) in CH$_2$Cl$_2$ (20 ml) dropwise over 1 hr., followed by the addition of the product of Example 19b (1.10 g, 2.14 mmol) in CH$_2$Cl$_2$ (25 ml) in the same manner over 30 min. After stirring the solution at −43° C. for an additional 1 hr., TEA (10.80 g, 107.0 mmol) was added and the solution allowed to warm slowly to room temperature. The solution was diluted with CH$_2$Cl$_2$, washed with 5% aqueous HCl, 5% aqueous NaOCl, dried over MgSO$_4$, filtered and the solvents removed under vacuum. The crude product was purified by flash chromatography on silica gel, eluting with MeOH:CHCl$_3$ (2:98) to give the product (420 mg) as a clear, light yellow syrup; TLC, $R_f$=0.32 and 0.37, silica gel, MeOH:CHCl$_3$ (5:95); HPLC, $t_R$=7.38 and 9.55, Zorbax® ODS analytical column, flow rate=0.5 ml/min, CH$_3$CN:H$_2$O: TFA (50:50:0.1).

Analysis calculated for: C$_{22}$H$_{36}$N$_3$O$_7$F$_3$ 0.75 H$_2$O: C, 50.33; H, 7.20; N, 8.00. Found: C, 50.34; H, 7.21; N, 7.58.

EXAMPLE 20

3(RS) -[(4-Methoxyphenyl)carbonyl]-L-valyl-N-[3-(4-methyl-1,1,1-trifluoro-2-oxopentyl)]-L-prolinamide a.

2(RS),3(SR)-[(4-Methoxyphenyl)carbonyl]-L-valyl-N-[3-(4-methyl-1,1,1-trifluoro-2-hydroxypentyl)]-L-prolinamide To a solution of a product made using the procedure of Example 3d (1.50 g, 4.08 mmol) and TEA (2.06 g, 20.4 mmol) in CHCl$_3$ (50 ml) cooled to 0° C., was added 4-methoxybenzoyl chloride (0.766 g, 4.49 mmol) in CHCl$_3$ (40 ml) dropwise over 1 hr. and the solution stirred at room temperature overnight. The solvents were removed under vacuum and the residue taken up in EtOAc, washed with 5% aqueous HCl, 20% aqueous NaOH, dried over solid K$_2$CO$_3$:Na$_2$SO$_4$ (10:90), filtered, and the solvents removed under vacuum. The crude product was purified by flash chromatography on silica gel, eluting with MeOH:CHCl$_3$ (5:95) to give the product (1.84 g) as a white foam; TLC, $R_f$=0.33, silica gel, MeOH:CHCl$_3$ (5:95).

Analysis calculated for: C$_{24}$H$_{34}$O$_5$N$_3$F$_3$ 0.3 H$_2$O: C, 56.86; H, 6.88; N, 8.29. Found: C, 56.80; H, 6.88; N, 8.07.

b.

3(RS)-[(4-Methoxyphenyl)carbonyl]-L-valyl-N-[3-(4-methyl-1,1,1-trifluoro-2-oxopentyl)]-L-prolinamide To a solution of oxalyl chloride (3.79 g, 29.9 mmol) in dry CH$_2$Cl$_2$ (50 ml) cooled to −43° C. was added DMSO (4.73 g, 59.8 mmol) in CH$_2$Cl$_2$ (20 ml) dropwise over 40 min., followed by addition of the product of Example 20a (1.50 g, 2.99 mmol) in CH$_2$Cl$_2$ (20 ml) in the same manner over 30 min. After stirring the solution at −43° C. for an addition 1 hr., TEA (15.10 g, 149.5 mmol) was added and the solution allowed to warm slowly to room temperature. The solution was diluted with CH$_2$Cl$_2$, washed with 5% aqueous HCl, 5% aqueous NaOCl, dried over MgSO$_4$, filtered and the solvents removed under vacuum. The crude product was purified by flash chromatography on silica gel, eluting with EtOAc: hexane (1:1) after pretreating the silica gel with TEA:hexane (10:90) to give the product (489 mg) as a white foam; TLC, $R_f$=0.15 and 0.19silica gel, MeOH:CHCl$_3$ (2:98); HPLC $t_R$=6.62 and 9.72, Zorbax® ODS column, flow rate=1 ml/min., CH$_3$CN:H$_2$O:TFA (50:50:0.1).

Analysis calculated for: C$_{24}$H$_{32}$O$_5$N$_3$F$_3$: C, 57.71; H, 6.46; N, 8.41. Found: C, 57.39; H, 6.67; N, 8.18.

EXAMPLE 21

3 (RS)-N$^2$,N$^6$-Di [(phenylmethoxy)carbonyl]-L-lysyl-N-[3-(4-methyl-1,1,1-trifluoro-2-oxopentyl)]-L-prolinamide a.

2(RS),3(SR)-N-[3-(4-Methyl-1,1,1-trifluoro-2-hyadroxypentyl)]-L-prolinamide

A product using the process of Example 2b was obtained.

b. 2(RS),3(SR)-N$^2$,N$^6$-Di [(phenylmethoxy)carbonyl]-L-lysyl-N-[3-(4-methyl-1,1,1-trifluoro-2-hydroxypentyl)]-L-prolinamide DCC (0.84 g, 4.09 mmol) was added to a stirred solution of (N$^2$,N$^6$-dibenzyloxycarbonyl)-L-lysine (1.54 g, 3.72 mmol), the product of Example 21a (1.0 g, 3.72 mmol), 1-hydroxybenzotriazole (1.01 g, 7.44 mmol), and dry THF (70 ml) at 0° C. under nitrogen. The reaction mixture was stirred at 0° C. for 1 hr. and allowed to warm to room temperature slowly overnight. The reaction mixture was filtered, the solvent removed under vacuum and the residue dissolved in CHCl$_3$. The CHCl$_3$ solution was washed with 20% aqueous citric acid, the organic layer was dried over Na$_2$SO$_4$ and filtered. The solvent was removed under vacuum to give the crude product (3.14 g). The product was purified by flash chromatography on silica gel eluting with CHCl$_3$:MeOH, (97:3) to afford 1.50 g of the final product, $R_f$=0.33–0.45, CHCl$_3$:MeOH (95:5), silica gel.

c.

3(RS)-N$^2$,N$^6$-Di[(phenylmethoxy)carbonyl]-L-lysyl-N-[3-(4-methyl-1,1,1-trifluoro-2-oxopentyl)]-L-prolinamide A solution of DMSO (3.59 g, 46 mmol) and dry CH$_2$Cl$_2$ (30 ml) was added to a stirred solution of oxalyl chloride (3.04 g, 24 mmol) and dry CH$_2$Cl$_2$ (50 ml) at −60° C. under nitrogen. The reaction mixture was stirred at −60° C. for 5 min. and was allowed to warm to −30° C. A solution of the product of Example 21b (1.32 g, 2.0 mmol) and dry CH$_2$Cl$_2$ (30 ml) was added dropwise. The resultant reaction mixture was stirred at −25° C. for 1 hr. TEA (7.8 g, 77.4 mmol) was added and the reaction mixture was allowed to slowly warm to room temperature. The reaction mixture was washed with 1N aqueous HCl, and brine. The organic layer was dried over Na$_2$SO$_4$, filtered, and the solvent removed under vacuum to give the product (2.6 g). The product was purified by flash chromatography (silica gel, CHCl$_3$:MeOH, 97:3, to afford the product (0.99 g); TLC, $R_f$=0.4–0.52, CHCl$_3$:MeOH (95:5), silica gel.

EXAMPLE 22

3(RS)-[(Phenylmethoxy)carbonyl]-L-phenylalanyl-N-[3-(4-methyl-1,1,1-trifluoro-2-oxopentyl)]-L-prolinamide a.

2(RS),3(SR)-[(Phenylmethoxy)carbonyl]-L-phenylalanyl-N-[3-(4-methyl-1,1,1-trifluoro-2-hydroxypentyl)]-L-prolinamide DCC (1.01 g, 4.92 mmol) was added to a stirred solution of a portion of the product of Example 21a (1.41 g, 4.47 mmol), N-(benzyloxycarbonyl)-L-phenylalanine (1.20 g, 4.47 mmol), 1-hydroxybenzotriazole (1.21 g, 8.94 mmol) and dry THF (75 ml) at 0° C. under nitrogen. The reaction mixture was stirred at 0° C. for 1 hr. and allowed to warm to room temperature and was stirred overnight. The reaction mixture was filtered and the solvent removed under vacuum to give the crude residue which was dissolved in CHCl$_3$. The CHCl$_3$ solution was washed with 20% aqueous citric acid and brine, and dried over Na$_2$SO$_4$. The CHCl$_3$ solution was filtered and the solvent removed under vacuum to give the crude product (3.57 g). The product was purified by flash chromatography on silica gel, eluting with CHCl$_3$:MeOH (97:3) to give the product (1.45 g) as a white foam; TLC, $R_f$=0.39–0.60, CHCl$_3$:MeOH (95:5), silica gel, HPLC:Zorbax ® ODS analytical column, CH$_3$CN:H$_2$O (50:50), flow rate=2.5 ml/min., $t_R$=6.47 and 7.63.

b. 3(RS)-[(Phenylmethoxy)carbonyl]-L-phenylalanyl-N-[3-(4-methyl-1,1,1-trifluoro-2-oxopentyl)]-L-prolinamide A solution of DMSO (2.33 g, 29.9 mmol) and dry CH$_2$Cl$_2$ (40 ml) was added dropwise to a stirred solution of oxalyl chloride (1.89 g, 14.9 mmol) and dry CH$_2$Cl$_2$ (40 ml) at −60° C. under nitrogen. The reaction was stirred at −60° C. for 0.5 hr. A solution of the product of Example 22a (1.43 g, 2.49 mmol) and dry CH$_2$Cl$_2$ (40 ml) was added at −50° C. The resultant mixture was stirred at −60° C. for 1 hr. Diisopropylethylamine (7.70 g, 59.7 mmol) was added and the reaction mixture was allowed to warm to room temperature. The mixture was washed twice with 1N aqueous HCl, then brine. The organic layer was dried over Na$_2$SO$_4$, filtered and the solvent was removed under vacuum to give the crude product (1.87 g). The product was purified by flash chromatography on silica gel, CHCl$_3$:MeOH (98:2) to give the product (0.771 g) as a white foam; TLC, $R_f$=0.62–0.69, CHCl$_3$:MeOH (95:5), silica gel; HPLC:Zorbax ® ODS analytical column, CH$_3$CN:H$_2$O (50:50), flow rate=2.5 ml/min., $t_R$=6.11 and 6.21.

Analysis calculated for: C$_{28}$H$_{32}$F$_3$N$_3$O$_5$: C, 61.41; H, 5.84; N, 7.67. Found: C, 61.53; H, 5.82; N, 7.67.

EXAMPLE 23

3(RS)-[2-(Methoxycarbonyl)ethylcarbonyl]-L-norleucyl-L-valyl-N-[3-(4-methyl-1,1,1-trifluoro-2-oxopentyl)]-L-prolinamide a. N-[2-(Methoxycarbonyl)ethylcarbonyl]-L-norleucine A solution of 1N sodium hydroxide (100 ml, 100 mmol) was added dropwise to a vigorously stirred mixture of L-norleucine (6.55 g, 50 mmol) and methylene chloride (250 ml) at 0° C. under nitrogen. 3-Carbomethoxypropionyl chloride (7.52 g, 50 mmol) was added dropwise. The resultant reaction mixture was stirred at 0° C. for 15 min. The cooling bath was removed and water (100 ml) was added. The pH was adjusted to 1 with 3N aqueous HCl. Ethyl acetate (200 ml) was added and the organic layer was separated. The aqueous layer was extracted with ethyl acetate and the organic layers were combined, washed with brine and dried over Na$_2$SO$_4$. The solution was filtered. The solvent was removed under vacuum to give the crude product (10.73 g). A portion of the crude product (6.47 g, 6.4 mmol) was purified by flash chromatography on silica gel, CHCl$_3$:MeOH, (97:3) to give the product (5.31 g); TLC, $R_f$=0.45, silica gel, CHCl$_3$:MeOH:AcOH (95:4.75:0.25).

b. 2(RS),3(SR)-[2-(Methoxycarbonyl)ethylcarbonyl]-L-norleucyl-L-valyl-N-[3-(4-methyl-1,1,1-trifluoro-2-hydroxypentyl)]-L-prolinamide Dicyclohexylcarbodiimide (3.46 g, 16.8 mmol) was added to a pre-cooled (0° C.) solution of a product made using the procedure of Example 3d (5.60 g, 15.3 mmol), the product of Example 23a (3.75 g, 15.3 mmol) and 1-hydroxybenzotriazole (4.13 g, 30.6 mmol) in THF (70 ml). The resulting solution was allowed to warm slowly to room temperature and stirred overnight. The reaction was filtered and concentrated under vacuum. The residue was diluted with EtOAc and the resulting solution washed with saturated aqueous NaHCO$_3$ and brine, dried over Na$_2$SO$_4$, filtered and concentrated under vacuum to give the crude product. The product was purified by flash chromatography on a column of silica gel using as eluent a gradient of Et$_2$O (100%), Et$_2$O: EtOAc (90:10), Et$_2$O: EtOAc (75:25), Et$_2$O: EtOAc (50:50) to give the product (5.6 g); TLC, $R_f$=0.45, silica gel, MeOH:CHCl$_3$ (1:9).

c. 3(RS)-[2-(Methoxycarbonyl)ethylcarbonyl]-L-norleucyl-L-valyl-N-[3-(4-methyl-1,1,1-trifluoro-2-oxopentyl)]-L-prolinamide A solution of DMSO (27.0 ml, 0.378 mol) in CH$_2$Cl$_2$ (27 ml) was added slowly to a pre-cooled (−65° C.) solution of oxalyl chloride (16.5 ml, 0.189 mol) in CH$_2$Cl$_2$ (350 ml). The resulting solution was stirred for 15 min. and a solution of the product of Example 23b (5.60 g, 0.00943 mol) in CH$_2$Cl$_2$ (250 ml) was added. The reaction was stirred for 1 hr. at −65° C. and diisopropylethylamine (67.0 ml, 0.378 mol) was added dropwise. The reaction was allowed to warm to room temperature and was then washed with 1N aqueous HCl and brine, dried over Na$_2$SO$_4$, filtered and concentrated under vacuum to give the crude product. The crude product was purified by flash chromatography on a column of silica gel eluting with a stepwise gradient of Et$_2$O (100%), Et$_2$O: EtOAc (50:50), EtOAc (100%) to give a partially purified product which was further purified by flash chromatography on silica gel eluting with a stepwise gradient of CHCl$_3$ (100%), MeOH:CHCl$_3$ (2.5:97.5) and MeOH:CHCl$_3$ (5:95) to give the final product (3.24 g); HPLC, $t_R$=6.80 and 12.98, Zorbax ® ODS analytical column, H$_2$O:CH$_3$CN (65:35), flow rate=2 ml/min.

EXAMPLE 24

3(RS)-[(2-Carboxyethyl)carbonyl]-L-norleucyl-L-valyl-N-[3-(4-methyl-1,1,1-trifluoro-2-oxopentyl)]-L-prolinamide 1N aqueous NaOH (9.5 ml) was added to a solution of the product of Example 23c (2.60 g, 4.39 mmol) in MeOH (95 ml). The reaction was stirred overnight at room temperature and 1N aqueous HCl (10.5 ml) was added. The reaction was concentrated under vacuum and H$_2$O (35 ml) was added. The suspension was extracted with EtOAc and the organic layer was washed with brine, dried over Na$_2$SO$_4$, filtered and concentrated under vacuum to give the product (2.1 g). HPLC, $t_R$=12.63 and 19.05, Zorbax ® ODS analytical column, H$_2$O:CH$_3$CN (65:35), flow rate=0.5 ml/min.

EXAMPLE 25

3(RS)-[(Phenylmethoxy)carbonyl]-L-alpha-glutamyl-L-valyl-N-[3-(4-methyl-1,1,1-trifluoro-2-oxopentyl)]-L-prolinamide phenylmethyl ester a. 2(RS),3(SR)-[(Phenylmethoxy)carbonyl]-L-alpha-glutamyl-L-valyl-N-[3-(4-methyl-1,1,1-trifluoro-2-hydroxypentyl)]-L-prolinamide phenylmethyl ester Isobutylchloroformate (0.53 ml, 4.1 mmol) was added to a pre-cooled (−15° C.) solution of N-benzyloxycarbonyl-L-glutamic acid-α-benzyl ester (1.52 g, 4.1 mmol) and N-methylmorpholine (0.45 ml, 4.1 mmol) in THF (30 ml). The reaction mixture was stirred for 10 min. and then cooled to −40° C. A solution of the product of Example 3d (1.5 g, 4.1 mmol) in THF (30 ml) was added dropwise and the reaction was stirred overnight and allowed to warm slowly to room temperature. The reaction was filtered and concentrated under vacuum. The residue was taken up in EtOAc, washed with 1N aqueous HCl and brine, dried over $Na_2SO_4$, filtered and concentrated to give the crude product. The product was purified by flash chromatography on a column of silica gel using as eluant a gradient of $CHCl_3$ (100%), MeOH:$CHCl_3$ (2.5:97.5) and MeOH:$CHCl_3$ (5:95) to give the product (2.13 g); TLC, $R_f$=0.43, silica gel, MeOH:$CHCl_3$ (5:95).

b.
3(RS)-[(Phenylmethoxy)carbonyl]-L-alpha-glutamyl-L-valyl-N-[3-(4-methyl-1,1,1-trifluoro-2-oxopentyl)]-L-prolinamide phenylmethyl ester A solution of DMSO (8.40 ml, 0.118 mol) in $CH_2Cl_2$ (8 ml) was added carefully to a pre-cooled (−65° C.) solution of oxalyl chloride (5.2 ml, 0.059 mol) in $CH_2Cl_2$ (100 ml). The solution was stirred for 15 min. and a solution of the product of Example 25a (2.13 g, 2.96 mmol) in $CH_2Cl_2$ (100 ml) was added dropwise. The reaction was stirred for 1 hr at −60° C. and N,N-diisopropylethylamine (20.9 ml, 0.118 mol) was added dropwise. The reaction was allowed to warm to room temperature, washed with 1N aqueous HCl and brine, dried over $Na_2SO_4$, filtered and concentrated to give the crude product. The product was partially purified by flash chromatography on a column of silica gel using as eluant a stepwise gradient of $Et_2O$ (100%), $Et_2O$:EtOAc (50:50) and EtOAc (100%). The product was finally purified by flash chromatography on a column of silica gel using as eluant a stepwise gradient of $CHCl_3$ (100%), MeOH:$CHCl_3$ (1:99), MeOH:$CHCl_3$ (2:98), MeOH:$CHCl_3$ (3:97) and MeOH:$CHCl_3$ (5:95) to give the product (1.35 g); HPLC, $t_R$=7.2 and 11.5, Zorbax® ODS analytical column, $H_2O$:$CH_3CN$ (50:50), flow rate=2 ml/min.

EXAMPLE 26

3(RS)-$N^2$-[2-(Methoxycarbonyl)ethylcarbonyl]-$N^6$-[(phenylmethoxy)carbonyl]-L-lysyl-L-valyl-N-[3-(4-methyl-1,1,1-trifluoro-2-oxopentyl)]-L-prolinamide a.
$N^2$-[(2-Methoxycarbonyl)ethylcarbonyl]-$N_6$-phenylmethoxycarbonyl lysine 1N aqueous NaOH (43 ml) was added to a pre-cooled (0° C.) solution of N-benzyloxycarbonyl-L-lysine (6.06 g, 0.0216 mol) in $CH_2Cl_2$ (160 ml). The reaction was vigorously stirred and 3-carbomethoxypropionyl chloride (2.66 ml, 0.0216 mol) was added. The reaction was vigorously stirred for 15 min at 0° C. Water (100 ml), 1N aqueous HCl (25 ml) and EtOAc (500 ml) were added successively and the layers were separated. The organic layer was washed with brine, dried over $Na_2SO_4$, filtered and concentrated to give the product (6.78 g). The product was used without further purification.

b.
2(RS),3(SR)-$N^2$-[2-(Methoxycarbonyl)ethylcarbonyl]-$N^6$-phenylmethoxycarbonyl-L-lysyl-L-valyl-N-[3-(4-methyl-1,1,1-trifluoro-2-hydroxypentyl)]-L-prolinamide DCC (2.85 g, 13.9 mmol) was added to a mixture of a product made using the procedure of Example 3d (4.63 g, 12.6 mmol), the product of Example 26a (5.00 g, 12.6 mmol), and HOBT (3.76 g, 27.8 mmol) in THF (65 ml) pre-cooled to 0° C. The mixture was stirred at 0° C. for 1 hr., warmed to room temperature and stirred overnight. The solvent was removed under vacuum, the residue diluted with EtOAc and washed successively with saturated $NaHCO_3$ and brine. The organic phase was dried over solid $K_2CO_3$:$Na_2SO_4$ (10:90), filtered, and the solvent removed under vacuum to give the crude product. Purification by flash chromatography on silica gel with an eluent of MeOH:$CHCl_3$ (1:99) gave the product (6.22 g) as a white foam; TLC, $R_f$=0.40, silica gel, MeOH:$CHCl_3$ (5:95).

c.
3(RS)-$N^2$-[2-(Methoxycarbonyl)ethylcarbonyl]-$N^6$-[(phenylmethoxy)carbonyl]-L-lysyl-L-valyl-N-[3-(4-methyl-1,1,1-trifluoro-2-oxopentyl)]-L-prolinamide A solution of DMSO (15.9 g, 100 mmol) in dry $CH_2Cl_2$ (50 ml) was added dropwise to a stirred solution of oxalyl chloride (8.8 ml, 200 mmol) in dry $CH_2Cl_2$ (150 ml) cooled to −43° C. under nitrogen. A solution of the product of Example 26b (6.22 g, 8.37 mmol) in $CH_2Cl_2$ (60 ml) was added in the same manner. The reaction mixture was stirred at −20° C. for 1 hr and TEA (70 ml, 400 mmol) was added dropwise. The mixture was allowed to slowly warm to room temperature, stirred for an additional 1 hr and then diluted with $CH_2Cl_2$, washed with 5% aqueous NaOCl, dried over solid $K_2CO_3$:$Na_2SO_4$ (10:90) filtered and the solvent removed under vacuum to give the crude product. Purification by flash chromatography on silica gel with an eluent of MeOH:$CHCl_3$ (1:99) gave the product (4.5 g) as a light yellow foam; TLC, $R_f$=0.51, silica gel, MeOH: $CHCl_3$ (1:9); HPLC, $t_R$=6.99 and 12.01, flow rate=1 ml/min, Zorbax® ODS analytical column, $H_2O$: $CH_3CN$: TFA (50:50:0.1).

EXAMPLE 27

3(RS)-$N^2$-[(2-Carboxyethyl)carbonyl]-$N^6$-[(phenylmethoxy)carbonyl]-L-lysyl-L-valyl-N-[3-(4-methyl-1,1,1-trifluoro-2-oxopentyl)]-L-prolinamide A solution of the product of Example 26c (2.0 g, 2.7 mmol) in MeOH (60 ml) and 1N NaOH (5.4 ml, 5.4 mmol) was stirred at room temperature for 12 hr. and then taken to pH 7 with 1N aqueous HCl (6.0 ml, 6.0 mmol). The MeOH was removed under vacuum; the resulting residue was dissolved in EtOAc, washed with brine, dried over $MgSO_4$, filtered and the solvent removed under vacuum to give the crude product. Purification by flash chromatography on silica gel (pH 5.5, Baker®) with chloroform gave the product (1.7 g) as a white foam; HPLC, $t_R$=4.06 and 5.56, flow rate=1 ml/min, Zorbax® ODS analytical column, $H_2O$:$CH_3CN$:TFA (50:50:0.1).

Analysis calculated for: $C_{34}H_{48}N_5O_9F_3$·1.75 $H_2O$: C, 53.78; H, 6.83; N, 9.22. Found: C, 53.46; H, 6.39; N, 9.03.

EXAMPLE 28

3S(orR)-$N^2$,$N^6$-Di[(phenylmethoxy)carbonyl]-L-lysyl-L-valyl-N-[3-(4-methyl-1,1,1-trifluoro-2-oxopentyl)]-L-prolinamide a.
2(RS),3(SR)-$N^2$,$N^6$-Di[(phenylmethoxy)carbonyl]-L-lysyl-L-valyl-N-[3-(4-methyl-1,1,1-trifluoro-2-hydroxypentyl)]-L-prolinamide DCC (0.93 g, 4.49 mmol) was added to a stirred solution of $N^{2-}$,$N^6$-benzyloxycarbonyl-L-lysine (1.69 g, 4.08 mmol), a product made using the procedure of Example 3d (1.50 g, 4.08 mmol), 1-hydroxybenzotriazole (1.10 g, 8.16 mmol) and dry THF (75 ml) at 0° C. under nitrogen. The reaction mixture was stirred at 0° C. for 1 hr., then was allowed to warm to room temperature and was stirred overnight. The reaction mixture was filtered. The filtrate was evaporated under vacuum. The residue was dissolved in $CHCl_3$ and the solution was washed with 1N aqueous HCl and brine and was dried over $Na_2SO_4$. The $Na_2SO_4$ was filtered and the filtrate was concentrated under vacuum to give the crude product (3.94 g) which was purified by flash chromatography on silica gel, $CHCl_3$:MeOH (95:5), to give 2.48 g of product; TLC, $R_f$=0.36–0.56, $CHCl_3$:MeOH (95:5), silica gel; HPLC, Zorbax ® ODS analytical column, flow rate=1.5 ml/min, $CH_3CN$:$H_2O$ (50:50); $t_R$=18.33, 14.99.

Analysis calculated for: $C_{33}H_{41}F_3N_4O_7$: C, 59.01; H, 6.24; N, 8.45. Found: C, 58.89; H, 6.33; N, 7.89.

b.
3S(orR)-$N^2$,$N^6$-Di[(phenylmethoxy)carbonyl]-L-lysyl-L-valyl-N-[3-(4-methyl-1,1,1-trifluoro-2-oxopentyl)]-L-prolinamide A solution of DMSO (2.8 g, 36.13 mmol) and dry $CH_2Cl_2$ (40 ml) was added to a stirred solution of oxalyl chloride and dry $CH_2Cl_2$ (40 ml) at −60° C. under nitrogen. Then a solution o f the product of Example 28a, (2.30 g, 3.01 mmol) and dry $CH_2Cl_2$ (40 ml) was added to the reaction mixture at −50° C. The resultant reaction mixture was stirred at −60° C. for 1 hr. Triethylamine (7.290 g, 72.26 mmol) was added and the reaction was allowed to warm to room temperature. The mixture was washed twice with 1N aqueous HCl, then brine and was dried over $Na_2SO_4$. The $Na_2SO_4$ was filtered and the filtrate was concentrated under vacuum to give the crude product (2.67 g). The product was purified by flash chromatography on silica gel with an eluent of $CHCl_3$:MeOH (97:3) to afford 64 mg of product; TLC, $R_f$=0.6, $CHCl_3$:MeOH (95:5); HPLC, Zorbax ® ODS analytical column, $CH_3CN$:$H_2O$ (60:40), flow rate=1.5 ml/min, $t_R$=5.29.

Analysis calculated for: $C_{38}H_{50}F_3N_5O_8 \cdot H_2O$: C, 58.53; H, 6.72; N, 8.98. Found: C, 58.95; H, 6.59; N, 8.74.

EXAMPLE 29

3 (RS)-1-(12-Methoxy-12-oxododecyloxy)carbonyl-N-[3-(1,1,1-trifluoro-4-methyl-2-oxopentyl)]-L-prolinamide (Formula Ia, $R^1$=$CH(CH_3)CH_3$, $R^3$=$CH_3OCO(CH_2)_{11}$, A=OCO, n=1)

a. Methyl 12-hydroxydodecanoate

A mixture of 1-hydroxydodecanoic acid (4.0 g, 18.5 mmol), MeOH (450 ml), conc $H_2SO_4$ (2.5 ml), and 3A molecular sieves (3 ml) was stirred at reflux for 16 hr. The mixture was neutralized with satd aq $NaHCO_3$, concentrated under vacuum, and partitioned between $Et_2O$ and water. The ethereal solution was washed (water, sat'd aq $NaHCO_3$, brine), dried ($Na_2SO_4$), filtered, and concentrated under vacuum to give the product (3.94 g) as a white solid; NMR (DMSO-$d_6$) δ3.65 (3H,s); 1.7–1.0 (22H,m).

b. 11-Methoxycarbonylundecyl 4-nitrophenyl carbonate

Using the method of Example 7a, the product of Example 29a was converted into the title compound and purified by flash chromatography (EtOAc:hexane (1:9)) to obtain the title compound in 59% yield; TLC, $R_f$=0.20, EtOAc:hexane (1:9).

c.
2(RS),3(SR)-1-(12-Methoxy-12-oxododecyloxy)carbonyl-N-[3-(1,1,1-trifluoro-2-hydroxy-4-methylpentyl)]-L-prolinamide (Formula VIIa, $R^1$=$CH(CH_3)CH_3$, $R^3$=$CH_3OCO(CH_2)_{11}$, A=OCO, n=1)

Using the method of Example 7b, the product of Example 29b was allowed to react with material prepared using the method of Example 2b to provide, after purification by flash chromatography (acetone:hexane (3:7)), the title product (45%); HPLC, $t_R$=4.43, Col A, $CH_3CN$:$H_2O$ (35:65), FR=2.0.

d. 3 (RS)
-1-(12-Methoxy-12-oxododecyloxy)carbonyl-N-[3-(1,1,1-trifluoro-4-methyl-2-oxopentyl)]-L-prolinamide (Formula Ia, $R^1$=$CH(CH_3)CH_3$, $R^3$=$CH_3OCO(CH_2)_{11}$, A=OCO, n=1)

To the product of Example 29c (1.1 mmol) was added DMSO (65 ml) and $Ac_2O$ (50 mmol). The resulting solution was stirred 18 hr at room temperature and diluted with $Et_2O$. The organic solution was washed (satd aq $NaHCO_3$ (3×), water, and brine), dried ($Na_2SO_4$), filtered, concentrated under vacuum, and purified by flash chromatography ($Et_2O$: hexane (1:1)) to afford the title product (100%); HPLC, $t_R$=12.73, Col A, $CH_3CN$:$H_2O$ (60:40), FR=2.0.

Analysis calculated for: $C_{22}H_{28}F_3N_3O_5 \cdot 0.4H_2O$: C, 55.91; H, 8.00; N, 5.21. Found: C, 56.05; H, 8.00; N, 5.19.

EXAMPLE 30

3 (RS)-1-(12-Hydroxy-12-oxododecyloxy)carbonyl-N-[3-(1,1,1-trifluoro-4-methyl-2-oxopentyl)]-L-prolinamide (Formula Ia, $R^1$=$CH(CH_3)CH_3$, $R^3$=$HOCO(CH_2)_{11}$, A=OCO, n=1)

Using the method of Example 14 the product of Example 29d was converted into the title product, purified by flash chromotography (EtOAc:hexane (1:1)) and obtained in 10% yield; HPLC, $t_R$=4.55, Col A, $CH_3CN$:$H_2O$ (60:40), FR=2.0.

Analysis calculated for: $C_{24}H_{39}F_3N_2O_6 \cdot 0.1H_2O$: C, 56.48; H, 7.74; N, 5.49. Found: C, 56.48; H, 7.96; N, 5.23.

EXAMPLE 31

3(RS)-1-[1-Oxo-5-(phenylmethoxycarbonylamino)pentyl]-N-[3-(1,1,1-trifluoro-4-methyl-2-oxopentyl)]-L-prolinamide (Formula Ia, $R^1$=$CH(CH_3)CH_3$, $R^3$=$\phi CH_2OCONH(CH_2)_4$, A=CO, n=1)

a. 5-(Phenylmethoxycarbonylamino)valeric acid

To a stirred, cooled solution (0°) of 5-amino valeric acid (5.00 g, 42.68 mmol) and 2N NaOH (32.0 ml, 32.0 mmol) was added simultaneously benzyl chloroformate (7.65 g, 6.40 ml, 44.81 mmol) and 2N NaOH (32.0 ml, 32.0 mmol). After stirring at 0° for 0.5 hr, the solution was washed with Et$_2$O. The Et$_2$O layer was acidified to pH 2.0 with 6N HCl, resulting in the product's precipitating out of solution. The title compound was filtered, washed (H$_2$O) and dried (vacuum oven) to give the pure product as a white solid (8.55 g, 80.0%), mp 104°-105° ; TLC, R$_f$=0.48, MeOH:CHCl$_3$:AcOH (3:97:0.1).

b.
2(RS),3(SR)-1-[1-Oxo-5-(phenylmethoxycarbonylamino)pentyl]-N-[3-(1,1,1-trifluoro-2-hydroxy-4-methylpentyl)]-L-prolinamide (Formula VIIa, R$^1$=CH(CH$_3$)CH$_3$, R$^3$=φCH$_2$OCONH(CH$_2$)$_4$, A=CO, n=1).

To a stirred, cooled solution (0°) of the product of Example 31a (0.47 g, 1.86 mmol), HOBT (0.50 g, 3.72 mmol), and DCC (0.40 g, 1.95 mmol) in CHCl$_3$ (50 ml) was added product prepared using the method of Example 2b (0.50 g, 1.86 mmol). After the reaction mixture had stirred overnight at room temperature, it was filtered and concentrated to afford a syrup which was partially dissolved in EtOAc. The insoluble material was filtered from the EtOAc solution before it was washed (satd aq NaHCO$_3$, 5% aq citric acid, and brine), dried (Na$_2$SO$_4$), and concentrated to a mixture which was purified by flash chromatography (MeOH:CHCl$_3$ (4:96)) to give the title product as a white foam (0.78 g, 84%); TLC, R$_f$=0.4, MeOH:CHCl$_3$ (4:94).

c.
3(RS)-1-[1-Oxo-5-(phenylmethoxycarbonylamino)pentyl]-N-[3-(1,1,1-trifluoro-4-methyl-2-oxopentyl)]-L-prolinamide (Formula Ia, R$^1$=CH(CH$_3$)CH$_3$, R$^3$=φCH$_2$OCONH(CH$_2$)$_4$, A=CO, n=1)

To the product of Example 31b (1 mmol) was added DMSO (85 mmol) and Ac$_2$O (64 mmol). The resulting solution was stirred for 18 hr at room temperature, poured into ice water (50 ml) and stirred for 1 to 4 hr. The crude product was extracted into EtOAc; and the EtOAc solution was washed (satd aq NaHCO$_3$, brine), dried (Na$_2$SO$_4$), filtered, and concentrated under vacuum before the product was purified by flash chromatography (CHCl$_3$:MeOH (97:3)) to afford the product (58%); HPLC, t$_R$=6.56 & 7.79, Col A, H$_2$O:CH$_3$CN (60:40), FR=2.0.

Analysis calculated for: C$_{24}$H$_{32}$F$_3$N$_3$O$_5$. 1.5H$_2$O: C, 54.74; H, 6.69; N, 7.98. Found: C, 54.87; H, 6.20; N, 8.02.

EXAMPLE 32

3(RS)-1-(1-Oxo-4-phenoxybutyl)-N-[3-(1,1,1-trifluoro-4-methyl-2-oxopentyl)]-L-prolinamide (Formula Ia, R$^1$=CH(CH$_3$)CH$_3$, R$^3$=φO(CH$_2$)$_3$, A=CO, n=1)

a.
2(RS),3(SR)-1-(1-Oxo-4-phenoxybutyl)-N-[3-(1,1,1-trifluoro-2-hydroxy-4-methylpentyl)]-L-prolinamide (Formula VIIa, R$^1$=CH(CH$_3$)CH$_3$, R$^3$=φO(CH$_2$)$_3$, A=CO, n=1)

To a 0.25M solution of 4-phenoxybutanoic acid in THF was added a molar equivalent amount of CDI in one portion. After the reaction mixture was stirred for 1 hr at room temperature, an molar equivalent amount of product prepared using the method of Example 2b was added in one portion. After the reaction was stirred overnight, excess satd aq NaHCO$_3$ was added; and the mixture was extracted with EtOAc. The EtOAc extracts were washed (in HCl, brine), dried (MgSO$_4$), filtered, and concentrated under vacuum to afford the title product (88%); TLC, R$_f$=0.53 & 0.61, MeOH:CH$_2$Cl$_2$ (1:9).

b.
3(RS)-1-(1-Oxo-4-phenoxybutyl)-N-[3-(1,1,1-trifluoro-4-methyl-2-oxopentyl)]-L-prolinamide (Formula Ia, R$^1$=CH(CH$_3$)CH$_3$, R$^3$=φO(CH$_2$)$_3$, A=CO, n=1).

By the method of Example 31c, the product of Example 32 a was converted into the title compound in 39% yield after crystallization from water; TLC; R$_f$=0.68 & 0.6 4, CH$_2$Cl$_2$:MeOH (9:1).

Analysis calculated for: C$_{21}$H$_{27}$F$_3$N$_2$O$_4$.1.25 H$_2$O: C, 55.93; H, 6.59; N, 6.21. Found: C, 55.88; H, 6.67; N, 6.15.

EXAMPLE 33

3(RS)-1-[2-(4-Morpholinyl)ethoxycarbonyl]-N-[3-1,1,1-trifluoro-4-methyl-2-oxopentyl)]-L-prolinamide (Formula Ia, R$^1$=CH(CH$_3$)CH$_3$, R$^3$=4-morpholinyl-(CH$_2$)$_2$, A=OCO, n=1)

a. 2-(4-Morpholinyl)ethyl 4-nitrophenyl carbonate hydrochloride

Using the method of Example 7a but with the omission of the pyridine (and of the acid wash), 2-(4-morpholinyl)ethanol was treated with 4-nitrophenyl chloroformate. The crude product was filtered, washed with Et$_2$O, and dried under vacuum. The product obtained (91%) was used for the subsequent reaction without further characterization.

b.
2(RS),3(SR)-1-[2-(4-Morpholinyl)ethoxycarbonyl]-N-[3-(1,1,1-trifluoro-2-hydroxy-4-methylpenytyl)]-L-prolinamide (Formula VIIa, R$^1$=CH(CH$_3$)CH$_3$, R$^3$=4-morpholinyl-(CH$_2$)$_2$, A=OCO, n=1)

Using the method of Example 7b, the product of Example 33a was allowed to react with product prepared using the method of Example 2b to provide, after purification by flash chromatography (MeOH:CHCl$_3$ (1:99)), the title product (68%); TLC, R$_f$=0.34, MeOH:CHCl$_3$ (5:95), FR=2.0.

c.
3(RS)-1-[2-(4-Morpholinyl)ethoxycarbonyl]-N-[3-1,1,1-trifluoro-4-methyl-2-oxopentyl)]-L-prolinamide (Formula Ia, R$^1$=CH(CH$_3$)CH$_3$, R$^3$=4-morpholinyl-(CH$_2$)$_2$, A=OCO, n=1)

To the product (1.1 mmol) of Example 33b was added DMSO (65 mmol) and Ac$_2$O (50 mmol). The resulting solution may be stirred 18 hr at room temperature and diluted with CH$_2$Cl$_2$. The organic solution may be washed (satd aq NaHCO$_3$ (3×), water, and brine), dried (Na$_2$SO$_4$), filtered and concentrated under vacuum before purification by flash chromatography (MeOH:CHCl$_3$ (2:98)) to provide the title product; HPLC, t$_R$=8.44 & 9.88, Col A, CH$_3$CN:H$_2$O (60:40), FR=2.0.

Analysis calculated for: C$_{18}$H$_{28}$F$_3$N$_3$O$_5$.1.OH$_2$O: C, 48.97; H, 6.85; N, 9.51. Found: C, 48.97; H, 6.61; N, 9.73.

EXAMPLE 34

3(RS)-1-[1-Oxo-6-[2-(2-pyridyl)ethoxy]carbonylaminohexyl]-N-[3-(1,1,1-trifluoro-4-methyl-2-oxopentyl)]-L-prolinamide (Formula Ia, $R^1$=CH(CH$_3$)CH$_3$, $R^3$=(2-pyridyl)—(CH$_2$)$_2$OCONH—(CH$_2$)$_5$, A=CO, n=1)

a. 4-Nitrophenyl 2-(2-pyridyl)ethyl carbonate

A solution of 2-pyridinethanol (1.38 g, 11 mmol) in Et$_2$O (20 mol) was added over 1 hr to a stirred solution of p-nitrophenylchloroformate (2.26 g, 11 mmol) at 0° under nitrogen. The resulting mixture was stirred for 1 hr at 0° before the precipitate which had formed was collected under a blanket of nitrogen and recrystallized from absolute EtOH to give 1.53 g (58%) of the title compound as off-white crystals, mp 125°–127°.

b. 2(RS),3(SR)-1-[1-Oxo-6-[2-(2-pyridyl)ethoxy]carbonylaminohexyl]-N-[3-(1,1,1-trifluoro-2-hydroxy-4-methylpentyl)]-L-prolinamide (Formula VIIa, $R^1$=CH(CH$_3$)CH$_3$, $R^3$=(2-pyridyl)(CH$_2$)$_2$OCONH(CH$_2$)$_5$, A=CO, n=1)

A solution of the amine product of Example 50b (0.75 g, 1.8 mmol), the product of Example 34a (0.675 g, 1.8 mmol), TEA (0.52 ml, 3.6 mmol), CH$_3$CN (25 ml) and water (25 ml) was stirred at room temperature for 2 days before the solvent was removed under vacuum to afford the crude product which was purified by flash chromatography (CH$_3$OH:CHCl$_3$ (2.5:97.5) to provide the product (1.13 mmol, 60%) as a pale yellow solid; TLC, R$_f$=0.5, CH$_3$OH:CHCl$_3$ (5:95).

c. 3(RS)-1-[1-Oxo-6-[2-(2-pyridyl)ethoxy]carbonylaminohexyl]-N-[3-(1,1,1-trifluoro-4-methyl-2-oxopentyl)]-L-prolinamide (Formula Ia, $R^1$=CH(CH$_3$)CH$_3$, $R^3$=(2-pyridyl)—(CH$_2$)$_2$OCONH(CH$_2$)$_5$, A=CO, n=1).

Using the method of Example 31c, the product of Example 34c was converted into the title product to afford, after purification by flash chromatography (MeOH:CH$_2$Cl$_2$ (3:97)) the title product in 10% yield; HPLC, t$_R$=1.84, Col A, H$_2$O:CH$_3$CN (60:40), FR=2.0.

Analysis calculated for: C$_{25}$H$_{35}$F$_3$N$_4$O$_5$·0.5H$_2$O: C, 55.85; H, 6.75; N, 10.40. Found: C, 56.08; H, 6.82; N, 10.43.

EXAMPLE 35

3(RS)-1-[2-Phenylmethoxy-1-(phenylmethoxymethyl)ethoxycarbonyl]-N-[3-(1,1,1-trifluoro-4-methyl-2-oxopentyl)]-L-prolinamide (Formula Ia, $R^1$=CH(CH$_3$)CH$_3$, $R^3$=($\phi$CH$_2$OCH$_2$)$_2$CH, A=OCO, n=1)

a. 4-Nitrophenyl 2-phenylmethoxy-1-(phenylmethoxymethyl)ethyl carbonate

TEA (0.74 g, 7.34 mmol) was added dropwise to a stirred solution of p-nitrophenylchloroformate (1.48 g, 7.34 mmol) and Et$_2$O (30 ml) between 0° and 5°. To the above reaction mixture a solution of 1,3-dibenzylglycerol (2.0 g, 7.34 mmol) and Et$_2$O (20 ml) was added between 0° and 5°, and the resulting mixture was stirred for 2 hr between 0° and 5° before it was allowed to warm to room temperature and stirred overnight. The reaction mixture was filtered and concentrated under vacuum to leave 3.6 g of yellow oil which was purified by flash chromatography (hexane:Et$_2$O (8:2)) to give 2.19 g (68%) of the title compound as a clear oil; TLC, R$_f$=0.33, hexane:ether (7:3).

b. 2(RS),3(SR)-1-[2-Phenylmethoxy-1-(phenylmethoxymethyl)ethoxycarbonyl]-N-[3-(1,1,1-trifluoro-2-hydroxy-4-methylpentyl)]-L-prolinamide (Formula VIIa, $R^1$=CH(CH$_3$)CH$_3$, $R^3$=($\phi$CH$_2$OCH$_2$)CH, A=OCO, n=1).

Using the method of Example 7b, product of Example 35a was allowed to react with the product prepared using the method of Example 2b to provide, after purification by flash chromatography (CHCl$_3$:EtOAc (95:5)), the title product (62%); HPLC, t$_R$=5.81 & 6.29, Col A, H$_2$O:CH$_3$CN (40:60), FR=2.0.

c. 3(RS)-1-[2-Phenylmethoxy-1-(phenylmethoxymethyl)ethoxycarbonyl]-N-[3-(1,1,1-trifluoro-4-methyl-2-oxopentyl)]-L-prolinamide (Formula Ia, $R^1$=CH(CH$_3$)CH$_3$, $R^3$=($\phi$CH$_2$OCH$_2$)$_2$CH, A=OCO, n=1)

Using the method of Example 31c, the product of Example 35b was oxidized to afford, after purification by flash chromatography (CHCl$_3$:EtOAc (98:2)), the title product (13%); HPLC, t$_R$=5.62, Col A, H$_2$O:CH$_3$CN (40:60), FR=2.0.

Analysis calculated for: C$_{29}$H$_{35}$F$_3$N$_2$O$_6$·0.25H$_2$O: C, 61.20; H, 6.28; N, 4.92. Found: C, 61.28; H, 6.34; N, 5.15.

EXAMPLE 36

3(RS)-1-[1-Oxo-4-(1-oxo-2-phenoxyethylamino)butyl]-N-3-(1,1,1-trifluoro-4-methyl-2-oxopentyl)]-L-prolinamide (Formula Ia, $R^1$=CH(CH$_3$)CH$_3$, $R^3$=$\phi$OCH$_2$CONH(CH$_2$)$_3$, A=CO, n=1)

a. Ethyl 4-(1-oxo-2-phenoxyethylamino)butanoate

To a stirred mixture of ethyl 4-aminobutanoate hydrochloride (3.4 g) and phenoxyacetyl chloride (2.76 ml) in 50 ml of Et$_2$O and 50 ml of water was added one portion of NaHCO$_3$ (4.2 g). After 2 hr the layers were separated and the organic phase was washed (1N HCl, brine), dried (MgSO$_4$), and filtered. Evaporation of the solvent under vacuum gave 3.1 g (53%) of the title compound as an oil.

b. 4-(1-Oxo-2-phenoxyethylamino)butanoic acid

A mixture of the product of Example 36a (3.1 g) in 1N NaOH (15 ml) was stirred for 6 hr at room temperature. The resulting solution was made acidic with 2N HCl. The solid which precipitated was collected, washed with water and dried under high vacuum. There was obtained 2.5 g (95%) of the title compound as a white solid, mp. 91°–94°.

c. 2(RS),3(SR)-1-[1-Oxo-4-(1-oxo-2-phenoxyethylamino)butyl]-N-[3-(1,1,1-trifluoro-2-hydroxy-4-methylpentyl)]-L-prolinamide (Formula VIIa, $R^1$=CH(CH$_3$)CH$_3$, $R^3$=$\phi$OCH$_2$CONH(CH$_2$)$_3$, A=CO, n=1)

Using the method of Example 32a, the product of Example 36b was allowed to react with product prepared using the method of Example 2b to provide, after purification by an acid and base wash workup, the title product (92%); TLC, $R_f$=0.43 & 0.48, MeOH:CH$_2$Cl$_2$ (1:9).

d.

3(RS)-1-[1-Oxo-4-(1-oxo-2-phenoxyethylamino)butyl]-N-[3-(1,1,1-trifluoro-4-methyl-2-oxopentyl)]-L-prolinamide (Formula Ia, R$^1$=CH(CH$_3$)CH$_3$, R$^3$=ϕOCH CONH(CH$_2$) A=CO n=1)

Using the method of Example 61c, the product of Example 36d was oxidized to afford, after purification by flash chromatography (MeOH: CH$_2$Cl$_2$ (3:97)), the title product (75%); HPLC, $t_R$=4.62 & 6.02, Col A, CH$_3$CN :H$_2$O (65: 35), FR=2.0.

Analysis calculated for: C$_{23}$H$_{30}$F$_3$N$_3$O$_5$: C, 56.26; H, 6.28; N, 8.56. Found: C, 56.28; H, 6.40; N, 8.30.

EXAMPLE 37

3(RS)-1-(4-Methoxy-1,4-dioxobutyl)-N-[3-(1,1,1-trifluoro-4-methyl-2-oxopentyl)]-L-prolinamide (Formula Ia, R$^1$=CH(CH$_3$)CH$_3$, R$^3$=CH$_3$OCO(CH$_2$)$_2$, A=CO, n=1)

a.

2(RS),3(SR)-1-(4-Methoxy-1,4-dioxobutyl)-N-[3-(1,1,1-trifluoro-2-hydroxy-4-methylpentyl)]-L-prolinamide (Formula VIIa, R$^1$=CH(CH$_3$)CH$_3$, R$^3$=CH$_3$OCO(CH$_2$)$_2$, A=CO ,n=1).

To a stirred mixture of product prepared using the method of Example 2b (1.34 g) in CH$_2$Cl$_2$ (50 ml) and 1N NaOH (6 ml) cooled in an ice-water bath was added dropwise 3-carbomethoxypropionyl chloride (0.75 g). After 1 hr the layers were separated and the organic phase was dried (Na$_2$SO$_4$), filtered and evaporated to provide 1.1 g (58%) of the title compound as a white powder; TLC, $R_f$=0.57, MeOH:CH$_2$Cl$_2$ (1:9).

b.

3(RS)-1-(4-Methoxy-1,4-dioxobutyl)-N-[3-(1,1,1-trifluoro-4-methyl-2-oxopentyl)]-L-prolinamide (Formula Ia, R$^1$=CH(CH$_3$)CH$_3$, R$^3$=CH$_3$OCO(CH$_2$)$_2$, A=CO, n=1)

Using the method of Example 61c, the product of Example 37a was oxidized to afford, after purification by flash chromatography (MeOH:CH$_2$Cl$_2$ (2:98)), the title product (71%); TLC, $R_f$=0.58, MeOH: CH$_2$Cl$_2$ (1:9).

Analysis calculated for: C$_{16}$H$_{23}$F$_3$N$_2$O$_5$.0.75H$_2$O: C, 48.79; H, 6.27; N, 7.11. Found: C, 49.04; H, 6.12; N, 6.83.

EXAMPLE 38

3(RS)-1-[3-(1,1-Dimethylethoxycarbonyl)amino-1-oxopropyl]-N-[3-(1,1,1-trifluoro-4-methyl-2-oxopentyl)]-L-prolinamide (Formula Ia, R$^1$=CH(CH$_3$)CH$_3$, R$^3$=(CH$_3$)$_3$COCONH(CH$_2$)$_2$, A=CO, n=1)

a. 2(RS),3(SR)-1-[3-(1,1-Dimethylethoxycarbonyl)amino-1-oxopropyl]-N-[3-(1,1,1-trifluoro-2-hydroxy-4-methylpentyl)]-L-prolinamide (Formula VIIa, R$^1$=CH(CH$_3$)CH$_3$, R$^3$=(CH$_3$)$_3$COCONH(CH$_2$)$_2$, A=CO, n=1).

Using the method of Example 32a, 3-(BOC-amino)-propanoic acid was allowed to react with product prepared using the method of Example 2b to provide the title product (80%); TLC, $R_f$=0.35, MeOH:CH$_2$Cl$_2$ (1:9).

b.

3(RS)-1-[3-(1,1-Dimethylethoxycarbonyl)amino-1-oxopropyl]-N-[3-(1,1,1-trifluoro-4-methyl-2-oxopentyl)]-L-prolinamide (Formula Ia, R$^1$=CH(CH$_3$)CH$_3$, R$^3$=(CH$_3$)$_3$COCONH(CH$_2$)$_2$, A=CO, n=1)

Using the method of Example 61c, the product of Example 38a was oxidized to afford, after purification by flash chromatography (MeOH:CH$_2$Cl$_2$ (2:98)), the named product (61%); TLC, $R_f$=0.46, MeOH: CH$_2$Cl$_2$ (1:9).

Analysis calculated for: C$_{19}$H$_{30}$F$_3$N$_3$O$_5$. 0.75H$_2$O: C, 50.83; H, 6.62; N, 9.39. Found: C, 51.18; H, 7.00; N, 9.28.

EXAMPLE 39

3(RS)-1-(3-Benzoylamino-1-oxopropyl)-N-[3-(1,1,1-trifluoro-4-methyl-2-oxopentyl)]-L-prolinamide (Formula Ia, R$^1$=CH(CH$_3$)CH$_3$, R$^3$=ϕCONH(CH$_2$)$_2$, A=CO, n=1)

a.

2(RS),3(SR)-1-(3-Benzoylamino-1-oxopropyl)-N-[3-(1,1,1-trifluoro-2-hydroxy-4-methylpentyl)]-L-prolinamide (Formula VIIa, R$^1$=CH(CH$_3$)CH$_3$, R$^3$=ϕCONH(CH$_2$)$_2$, A=CO, n=1)

Using the method of Example 32a, 3-(benzoylamino)-propanoic acid was allowed to react with product prepared using the method of Example 2b to provide the title product (83%); TLC, $R_f$=0.39 & 0.42, MeOH:CH$_2$Cl$_2$ (1:9).

b.

3(RS)-1-(3-Benzoylamino-1-oxopropyl)-N-[3-(1,1,1-trifluoro-4-methyl-2-oxopentyl)]-L-prolinamide (Formula Ia, R$^1$=CH(CH$_3$)CH$_3$, R$^3$=ϕCONH(CH$_2$)$_2$, A=CO, n=1)

Using the method of Example 61c, the product of Example 39a was oxidized to afford, after purification by flash chromatography (MeOH:CH$_2$Cl$_2$ (2:98)), the title product (48%); TLC, $R_f$=0.54, MeOH:CH$_2$Cl$_2$ (1:9).

Analysis calculated for: C$_{21}$H$_{26}$F$_3$N$_3$O$_4$: C, 57.14; H, 5.94; N, 9.52. Found: C, 57.12; H, 6.59; N, 9.45.

EXAMPLE 40

3(RS)-1-[3-(1-Oxo-2,2-diphenylethyl)amino]-1-oxobutyl-N-[3-(1,1,1-trifluoro-4-methyl-2-oxopentyl)]-L-prolinamide (Formula Ia, R$^1$=CH(CH$_3$)CH$_3$, R$^3$=ϕ$_2$CHCONH(CH$_2$)$_3$, A=CO, n=1)

a. Ethyl 3-(1-oxo-2,2-diphenylethyl)aminobutanoate

To a stirred solution of ethyl 4-aminobutyrate hydrochloride (2.51 g) and diphenylacetyl chloride (3.46 g) in 50 ml of CH$_2$Cl$_2$ was added 50 ml of water followed by the addition of one portion of NaHCO$_3$ (3.4 g). After 2 hr the layers were separated and the organic phase dried (Na$_2$SO$_4$), filtered and evaporated. There was obtained 3.5 g (72%) of the title compound as a white solid; TLC, $R_f$=0.71, MeOH: CH$_2$Cl$_2$ (5:95).

b. 3-(1-Oxo-2,2-diphenylethyl)aminobutanoic acid

A mixture of the product of Example 40a (3.5 g) in 1N NaOH (30 ml) and EtOH (10 ml) was stirred for 10 hr. The solution was then extracted with Et$_2$O. The aqueous phase was made acidic with 2N HCl; and the precipitated solid was collected, washed with water and dried under high vacuum. There was obtained 2.9 g (93%) of the title compound as a white powder.

c.
2(RS),3(SR)-1-[3-(1-Oxo-2,2-diphenyethyl)amino-1-oxobutyl-N-[3-(1,1,1-trifluoro-2-hydroxy-4-methylpentyl)]-L-prolinamide (Formula VIIa, $R^1$=CH(CH$_3$)CH$_3$, $R^3$=$\phi_2$CHCONH(CH$_2$)$_3$, A=CO, n=1).

Using the method of Example 32a, the product of Example 40b was allowed to react with product prepared using the method of Example 2b to provide the title product (81%); TLC, $R_f$=0.13, MeOH:CH$_2$Cl$_2$ (5:95).

d.
3(RS)-1-[3-(1-Oxo-2,2-diphenylethyl)amino-1-oxobutyl-N-[3-(1,1,1-trifluoro-4-methyl-2-oxopentyl)]-L-prolinamide (Formula Ia, $R^1$=CH(CH$_3$)CH$_3$, $R^3$=$\phi_2$CHCONH(CH$_2$)$_3$, A=CO, n=1)

Using the method of Example 61c, the product of Example 40c was oxidized to afford, after purification by flash chromatography (MeOH:CH$_2$Cl$_2$ (2:98)), the title product (27%); TLC, $R_f$=0.24, MeOH: CH$_2$Cl$_2$ (5:95).

Analysis calculated for: C$_{29}$H$_{34}$F$_3$N$_3$O$_4$.1.0H$_2$O: C, 61.31; H, 6.48; N, 7.39. Found: C, 61.58; H, 6.77; N, 7.43.

EXAMPLE 41

3(RS)-1-[2-(2-Methoxyethoxy)ethoxycarbonyl]-N-[3-(1,1,1-trifluoro-4-methyl-2-oxopentyl)]-L-prolinamide (Formula Ia, $R^1$=CH(CH$_3$)CH$_3$, $R^3$=CH$_3$O(CH$_2$)$_2$O(CH$_2$)$_2$, A=OCO, n=1)

a.
2(RS),3(SR)-1-[2-(2-Methoxyethoxy)ethoxycarbonyl]-N-[3-(1,1,1-trifluoro-2-hydroxy-4-methylpentyl)]-L-prolinamide (Formula VIIa, $R^1$=CH(CH$_3$)CH$_3$, $R^3$=CH$_3$O(CH$_2$)$_2$O(CH$_2$)$_2$, A=OCO, n=1)

Using the method of Example 7b, the product of Example 19a was allowed to react with product prepared using the method of Example 2b to provide, after purification by dry column flash chromatography over silica gel using gradient elution with acetone: hexane from (10:90) to (50:50), the title product (75%); TLC, $R_f$=0.30 & 0.35, acetone:hexane (40:60).

b.
3(RS)-1-[2-(2-Methoxyethoxy)ethoxycarbonyl]-N-[3-(1,1,1-trifluoro-4-methyl-2-oxopentyl)]-L-prolinamide (Formula Ia, $R^1$=CH(CH$_3$)CH$_3$, $R^3$=CH$_3$O(CH$_2$)$_2$OCH$_2$)$_2$, A=OCO, n=1)

Using the method of Example 61c, the product of Example 41a was oxidized to afford, after purification by flash chromatography (acetone:CHCl$_3$ (1:3)), the title product (42%); HPLC, $t_R$=5.69, Col A, H$_2$O:CH$_3$CN (75:25), FR=2.0.

Analysis calculated for: C$_{17}$H$_{27}$F$_3$N$_2$O$_6$: C, 49.39; H, 6.83; N, 6.78. Found: C, 49.27; H, 6.80; N, 6.48.

EXAMPLE 42

3(RS)-1-[1,4-Dioxo-4-(phenylmethylamino)butyl]-N-[3-(1,1,1-trifluoro-4-methyl-2-oxopentyl)]-L-prolinamide (Formula Ia, $R^1$=CH(CH$_3$)CH$_3$, $R^3$=$\phi$CH NHCO(CH$_2$) A=CO n=1)

a. 4-Oxo-4-(phenylmethylamino)butanoic acid

A mixture of benzyl amine (10.7 g) and succinic anhydride (10 g) was stirred in THF (1 liter) for 2 days. The solid was filtered and dissolved in 1N NaOH (110 ml). The aqueous phase was washed with Et$_2$O and then made acidic with conc HCl while cooling in an ice-water bath. The solid was collected, washed with water and dried under high vacuum. There was obtained 10.9 g (53%) of the title compound as a white powder m. p. 137.5°–138°.

b.
2(RS),3(SR)-1-[1,4-Dioxo-4-(phenylmethylamino)-butyl]-N-[3-(1,1,1-trifluoro-2-hydroxy-4-methylpentyl)]-L-prolinamide (Formula VIIa, $R^1$=CH(CH$_3$)CH$_3$, $R^3$=$\phi$CH$_2$NHCO(CH$_2$)$_2$, A=CO, n=1)

Using the method of Example 32a, the product of Example 42a was allowed to react with product prepared using the method of Example 2b to provide the title compound (74%); TLC, $R_f$=0.48, MeOH:CH$_2$Cl$_2$ (1:9).

c.
3(RS)-1-[1,4-Dioxo-4-(phenylmethylamino)butyl]-N-[3-(1,1,1-trifluoro-4-methyl-2-oxopentyl)]-L-prolinamide (Formula Ia, $R^1$=CH(CH$_3$)CH$_3$, $R^3$=$\phi$CH$_2$NHCO(CH$_2$)$_2$, A=CO, n=1)

Using the method of Example 61c, the product of Example 42b was oxidized to afford, after purification by flash chromatography (MeOH:CH$_2$Cl$_2$ (2:98)), the title product (40%); TLC, $R_f$=0.56, MeOH: CH$_2$Cl$_2$ (1:9).

Analysis calculated for: C$_{22}$H$_{28}$F$_3$N$_3$O$_4$: C, 58.10; H, 6.20; N, 9.23. Found: C, 57.90; H, 6.36; N, 9.27.

EXAMPLE 43

3(RS)-1-[1-Oxo-3-(phenylmethoxycarbonylamino)-propyl]-N-[3-(1,1,1-trifluoro-4-methyl-2-oxopentyl)]-L-prolinamide (Formula Ia $R^1$=CH(CH$_3$)CH$_3$, $R^3$=$\phi$CH OCONH(CH$_2$)$_2$, A=CO, n=1)

a.
2(RS),3(SR)-1-[1-Oxo-3-(phenylmethoxycarbonylamino)propyl]-N-[3-(1,1,1-trifluoro-2-hydroxy-4-methylpentyl)]-L-prolinamide (Formula VIIa, $R^1$=CH(CH$_3$)CH$_3$, $R^3$=$\phi$CH OCONH(CH$_2$) A=CO n=1)

Using the method of Example 32a, CBZ-$\beta$-alanine was allowed to react with product prepared using the method of Example 2b to provide the title product (82%); TLC, $R_f$=0.59, MeOH:CH$_2$Cl$_2$ (1:9).

b.
3(RS)-1-[1-Oxo-3-(phenylmethoxycarbonylamino)-propyl]-N-[3-(1,1,1-trifluoro-4-methyl-2-oxopentyl)]-L-prolinamide (Formula Ia, $R^1$=CH(CH$_3$)CH$_3$, $R^3$=$\phi$CH$_2$OCONH(CH$_2$)$_2$, A=CO, n=1)

Using the method of Example 61c, the product of Example 43a was oxidized to afford, after purification by flash chromatography (MeOH:CH$_2$Cl$_2$ (2:98)), the title product (35%); TLC, $R_f$=0.23, MeOH: CH$_2$Cl$_2$ (5:95).

Analysis calculated for: C$_{22}$H$_{28}$F$_3$N$_3$O$_5$.0.4H$_2$O: C, 55.20; H, 6.06; N, 8.77. Found: C, 55.28; H, 6.25; N, 8.55.

EXAMPLE 44

3(RS)-1-[1-Oxo-4-(phenylmethoxycarbonylamino)-butyl]-N-[3-(1,1,1-trifluoro-4-methyl-2-oxopentyl)]-L-prolinamide (Formula Ia R¹=CH(CH₃)CH₃, R³=φCH₂OCONH(CH₂)₃, A=CO, n=1)

a.
2(RS),3(SR)-1-[1-Oxo-4-(phenylmethoxycarbonylamino)butyl]-N-[3-(1,1,1-trifluoro-2-hydroxy-4-methylpentyl)]-L-prolinamide (Formula VIIa, R¹=CH(CH₃)CH₃, R³=φCH OCONH(CH₂)₃, A=CO, n=1)

Using the method of Example 32a, CBZ-4-aminobutanoic acid was allowed to react with product prepared using the method of Example 2b to provide the title product (7290); TLC, R_f=0.47, Et₂O:EtOAc (1:1).

b.
3(RS)-1-[1-Oxo-4-(phenylmethoxycarbonylamino)-butyl]-N-[3-(1,1,1-trifluoro-4-methyl-2-oxopentyl)]-L-prolinamide (Formula Ia, R¹=CH(CH₃)CH₃, R³=φCH₂OCONH(CH₂)₃, A=CO, n=1)

Using the method of Example 61c, the product of Example 44a was oxidized to afford, after purification by preparative TLC (MeOH:CHCl₃ (2.5:97.5)), the title product (329°); TLC, R_f=0.65 & 0.68, MeOH:CHCl₃ (1:9)

EXAMPLE 45

3R(orS)-1-[1-Oxo-4-phenoxy-2-(2-phenoxyethyl)butyl]-N-[3-(1,1,1-trifluoro-4-methyl-2-oxopentyl)]-L-prolinamide (Formula Ia, R¹=CH(CH₃)CH₃, R³=[φO(CH₂)₂]₂CH A=CO, n=1)

a. Diethyl 2,2-di(2-phenoxyethyl)malonate

To a stirred solution of sodium (2.3 g) in absolute EtOH (50 ml) was added diethyl malonate (15.2 ml) followed by 2-phenoxyethyl chloride (15.7 g). The reaction mixture was then refluxed for 12 hr. The EtOH was evaporated under vacuum and the mixture diluted with water (40 ml). The aqueous phase was extracted with Et₂O. The combined Et₂O extracts were washed (brine), dried (MgSO₄) filtered and evaporated. Bulb to bulb distillation afforded 12.2 g (27%) of the title diester as a clear liquid, bp 155°-175° (106 Pascals, 0.8 Torr); TLC, R_f=0.34, CH₂Cl₂.

b. 4-Phenoxy-2-(2-phenoxyethyl)butanoic acid

A mixture of the product of Example 45a (10.0 g) and potassium hydroxide (17.7 g) in water (22 ml) was refluxed for 4 hr. The reaction mixture was cooled and acidified with conc HCl. The precipitated solid was collected, washed with water and air dried. The solid obtained (8.44 g) was heated at 170° for 2 hr and then cooled. Recrystallization of the solid from cyclohexane gave 4.1 g (93%) of the title compound as fine white needles; mp 85°-86°.

Analysis calculated for: C₁₈H₂₀O₄: C, 71.98; H, 6.71. Found: C, 71.92; H, 6.71.

c. 4-Phenoxy-2-(2-phenoxyethyl)butanoyl chloride

A mixture of the product of Example 45b (1.5 g) and thionyl chloride (0.73 ml) was heated on a steam bath for 1 hr. The reaction mixture was then stripped. The acid chloride title product was obtained as a clear oil in quantitative yield and was used directly.

d.
2(RS),3(SR)-1-[1-Oxo-4-phenoxy-2-(2-phenoxyethyl)-butyl]-N-[3-(1,1,1-trifluoro-2-hydroxy-4-methylpentyl)]-L-prolinamide (Formula VIIa, R¹=CH(CH₃)CH₃, R³=[φO(CH₂)₂]₂CH, A=CO, n=1)

Using the method of Example 37a, the product of Example 45c was allowed to react with product prepared using the method of Example 2b to provide the title product (95%); TLC, R_f=0.47 & 0.54, Et₂O.

e. 3R(or S)-[1-Oxo-4-phenoxy-2-(2-phenoxyethyl)butyl]-N-[3-(1,1,1-trifluoro-4-methyl-2-oxopentyl)]-L-prolinamide (Formula Ia R¹=CH(CH₃)CH₃, R³=[φO(CH₂)₂]₂CH, A=CO, n=1)

Using the method of Example 61c, the product of Example 45d was oxidized to afford the crude product as a mixture of diastereomers which was separated by flash chromatography (Et₂O:hexane (gradient elution, 60:40 to 75:25)). The faster eluting diastereomer was the title compound, obtained in 27.7% yield; HPLC, t_R=6.94, Col A, CH₃CN:H₂O (65:35), FR=2.0.

Analysis calculated for: C₂₉H₃₅F₃N₂O₅: C, 63.49; H, 6.43; N, 5.11. Found: C, 63.39; H, 6.47; N, 5.07.

EXAMPLE 46

3S(or R)-[1-Oxo-4-phenoxy-2-(2-phenoxyethyl)butyl]-N-[3-(1,1,1-trifluoro-4-methyl-2-oxopentyl)]-L-prolinamide (Formula Ia, R¹=CH(CH₃)CH₃, R³=[φO(CH₂)₂]₂CH, A=CO, n=1)

From the separation of the diastereomers of the crude product described in Example 45e, the slower eluting diastereomer was the title compound here, obtained in 28.3% yield; HPLC, t_R=5.04, Col A, CH₃CH: H₂O (65:35), FR=2.0.

Analysis calculated for: C₂₉H₃₅F₃N₂O₅: C, 63.49; H, 6.43; N, 5.11. Found: C, 63.50; H, 6.45; N, 5.26.

EXAMPLE 47

3(RS)-1-[6-[(4-Ethoxycarbonylphenyl)aminocarbonylamino]-1-oxo]hexyl-N-[3-(1,1,1-trifluoro-4-methyl-2 -oxopentyl)]-L-prolinamide (Formula Ia, R¹=CH(CH₃)CH₃, R³=4-(CH₃CH₂OCO)φNHCONH(CH₂)₅, A=CO, n=1)

a.
2(RS),3(SR)-1-[6-[(4-Ethoxycarbonylphenyl)aminocarbonylamino]-1-oxo]hexyl-N-[3-(1,1,1-trifluoro-2-hydroxy-4-methylpentyl)]-L-prolinamide (Formula VIIa, R¹=CH(CH₃)CH₃, R³=4-(CH₃CH₂OCO)ONHCONH(CH₂)₅, A=CO, n=1)

Ethyl p-isocyanatobenzoate (0.288 g, 1.5 mmol) was added to a stirred solution of the product of Example 50b (0.6 g, 1.5 mmol), TEA (0.15 g, 1.5 mmol), and DMF (20 ml) under nitrogen at room temperature. The resulting mixture was stirred at room temperature overnight before it was concentrated under vacuum to leave an amber residue which was dissolved in EtOAc. The EtOAc solution was washed (1N HCl), dried (MgSO₄), filtered, and concentrated under vacuum to leave 1.15 g of oily residue. This residue was purified by flash chromatography (CHCl₃:CH₃OH (97:3)) to give 0.62 g (70%) of the title compound as a white solid; TLC, $R_f$=0.28 & 0.35, $CHCl_3:CH_3OH$ (95:5).

b.

3(RS)-1-[6-[(4-Ethoxycarbonylphenyl)aminocarbonylamino]-1-oxo]hexyl-N-[3-(1,1,1-trifluoro-4-methyl-2-oxopentyl)]-L-prolinamide (Formula Ia, $R^1$=$CH(CH_3)CH_3$, $R^3$=4, $(CH_3CH_2OCO)ONHCONH(CH_2)_5$, A=CO, n=1)

Using the method of Example 61c the product of Example 47a was oxidized to afford, after purification by flash chromatography ($CHCl_3:MeOH$ (97:3)), the title product (43%); HPLC, $t_R$=12.39 & 15.79, Col. A, $H_2O:CH_3CN$ (65:35), FR=2.0.

Analysis calculated for: $C_{27}H_{37}F_3N_4O_6 \cdot 1.0H_2O$: C, 55.09; H, 6.68; N, 9.51. Found: C, 54.75; H, 6.63; N, 9.29.

EXAMPLE 48

3(RS)-1-[6-(Phenylmethoxycarbonylamino)-1-oxohexyl]-N-[3-(1,1,1-trifluoro-4-methyl-2-oxopentyl)]-L-prolinamide (Formula Ia $R^1$=$CH(CH_3)CH_3$, $R^3$=$\phi CH_2OCONH(CH_2)_5$, A=CO, n=1)

Using the method of Example 31c, the product of Example 50a was oxidized to afford, after purification by flash chromatography ($CHCl_3:MeOH$ (97:3)), the title product (31%); HPLC, $t_R$=4.06, Col. A, $CH_3CN:H_2O$ (1:1), FR=2.0.

Analysis calculated for: $C_{25}H_{34}F_3N_3O_5 \cdot 0.5H_2O$: C, 57.46; H, 6.75; N, 8.04. Found: C, 57.87; H, 6.24; N, 7.86.

EXAMPLE 49

3(RS)-1-[6-[(4-Hydroxycarbonylphenyl)aminocarbonylamino]-1-oxohexyl-N-[3-(1,1,1-trifluoro-4-methyl-2oxopentyl) ]-L-prolinamide (Formula Ia, $R^1$=$CH(CH_3)CH_3$, $R^3$=4-(HOCO)$\phi$NHCONH(CH_2)_5$, A=CO, n=1)

Using the method of Example 14, the product of Example 47b was converted into the title product in 38% yield; HPLC, $t_R$=6.24 & 8.0, Col. A, $H_2O:CH_3CN$ (75:25), FR=2.0.

Analysis calculated for: $C_{25}H_{33}F_3N_4O_6 \cdot 2.5H_2O$: C, 51.1; H, 6.50; N, 9.50. Found: C, 51.34; H, 5.93; N, 8.95.

EXAMPLE 50

3(RS)-1-(6-Phenylsulfonylamino-1-oxohexyl)-N-[3-(1,1,1-trifluoro-4-methyl-2-oxopentyl)]-L-prolinamide (Formula Ia, $R^1$=$CH(CH_3)CH_3$, $R^3$=$\phi S(O_2)NH(CH_2)_5$, A=CO, n=1)

a.

2(RS),3(SR)-1-[6-(Phenylmethoxycarbonylamino)-1-oxohexyl ]-N-[3-(1,1,1-trifluoro-2-hydroxy-4-methylpentyl)]-L-prolinamide (Formula VIIa, $R^1$=$CH(CH_3)CH_3$, $R^3$=$\phi CH_2OCONH(CH_2)_5$, A=CO, n=1)

DCC (6.35 g, 30.8 mmol) was added to a stirred solution of N-CBZ-aminocaproic acid (6.84 g, 25.7 mmol), material prepared by the method of Example 2b (6.89 g, 25.7 mmol), HOBT (6.94 g, 51.4 mmol) and dry THF (250 ml) at 0° C. under nitrogen. The resulting reaction mixture was stirred at 0° C. for 1 hr, was allowed to warm to room temperature, and was stirred overnight before it was filtered. The filtrate was concentrated under vacuum to a brown residue which was dissolved in $CHCl_3$, and the $CHCl_3$ solution was washed (20% citric acid solution), dried ($Na_2SO_4$), filtered, and concentrated under vacuum. The residue was purified by flash chromatography ($CHCl_3:MeOH$ (97:3)) to give 8.0 g (61%) of the title compound as a waxy solid; TLC, $R_f$=0.35, $CHCl_3:MeOH$ (95:5).

b.

2(RS),3(SR)-1-(6-Amino-1-oxohexyl)-N-[3-(1,1,1-trifluoro-2-hydroxy-4-methylpentyl)]-L-prolinamide (Formula VIIa, $R^1$=$CH(CH_3)CH_3$, $R^3$=$H_2N(CH_2)_5$, A=CO, n=1).

A mixture of the product of Example 50a (2.06 g, 3.99 mmol), EtOH (100 ml), and 10% Pd/C (0.3 g) was placed on a Parr® shaker under 310,344.8 Pascals (45 psi) of $H_2$ for 3 hr. The mixture was filtered through Celite® and the Celite® cake was washed with EtOH. The EtOH washes and the above filtrate were combined and concentrated under vacuum to give 1.36 g (86%) of the title compound as a pale green waxy oil; TLC, $R_f$=0.2, $CHCl_3:MeOH$ (85:15).

c.

2(RS),3(SR)-1-(6-Phenylsulfonylamino-1-oxohexyl)-N-[3-(1,1,1-trifluoro-2-hydroxy-4-methylpentyl)]-L-prolinamide (Formula VIIa $R^1$=$CH(CH_3)CH_3$, $R^3$=$\phi S(O_2)NH(CH_2)_5$, A=CO, n=1)

Benzenesulfonyl chloride (0.6 g, 1.5 mmol) was added to a stirred solution of the product of Example 50b (0.26 g, 1.5 mmol), TEA (0.3 g, 3.0 mmol), and dry DMF (20 ml) under nitrogen at room temperature and the resulting mixture was stirred at room temperature overnight. The DMF was removed under vacuum to leave a brownish residue which was dissolved in EtOAc. The EtOAc solution was washed (1N HCl), dried ($MgSO_4$), and filtered. The filtrate was concentrated under vacuum to a residue which was purified by flash chromatography ($CHCl_3:MeOH$ (97:3)) to give 0.48 g (60%) of the title compound as a white powder; TLC, $R_f$=0.30 & 0.40, $CHCl_3:MeOH$ (95:5).

d.

3(RS)-1-(6-Phenylsulfonylamino-1-oxohexyl)-N-[3-(1,1,1-trifluoro-4-methyl-2-oxopentyl)]-L-prolinamide (Formula Ia, $R^1$=$CH(CH_3)CH_3$, $R^3$=$\phi S(O_2)NH(CH_2)_5$, A=CO, n=1)

Using the method of Example 8b, the product of Example 50c was oxidized to afford, after purification by flash chromatography ($Et_2O:hexane$ (3:1) followed by a second column using $CHCl_3:MeOH$ (97:3)), the title product (36%); HPLC, $t_R$=8.48 & 10.33, $CH_3CN:H_2O$ (35:65), FR=2.0.

EXAMPLE 51

3(RS)-(1-Naphthylcarbonyl)-L-valyl-N-[3-(1,1,1-trifluoro-4-methyl-2-oxopentyl)]-L-prolinamide (Formula Ib, $R^1$=$CH(CH_3)CH_3$, $R^2$=$CH(CH_3)_2$, $R^3$=1-naphthyl, $R^4$=H, A=CO, n=1)

a.

2(RS),3(SR)-(1-Naphthylcarbonyl)-L-valyl-N-[3-(1,1,1-trifluoro-2-hydroxy-4-methylpentyl)]-L-prolinamide (Formula VIIb, $R^1$=$CH(CH_3)CH_3$, $R^2$=$CH(CH_3)_2$, $R^3$=1-naphthyl, $R^4$=H, A=CO, n=1)

According to the method of Example 20a, material prepared by the procedure of Example 3d was allowed to react with 1-naphthalenecarbonylchloride to provide the title compound, isolated in 38% yield after purification by preparative TLC (hexane:$Et_2O$ (4:6)); TLC, $R_f$=0.46 & 0.41, MeOH:$CHCl_3$ (5:95).

Analysis calculated for: $C_{27}H_{32}F_3N_3O_4$: C, 60.32; H, 6.37; N, 7.82. Found: C, 60.89; H, 6.21; N, 7.68.

b.

3(RS)-(1-Naphthylcarbonyl)-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)$_2$, $R^3$=1-naphthyl, $R^4$=H, A=CO, n=1)

A solution of DMSO (29.7 g, 380 mmol) in CH$_2$Cl$_2$ (81 ml) was added slowly to a precooled solution (−43°) of oxalyl chloride (24.0 g, 190 mmol) in CH$_2$Cl$_2$ (350 ml), and the resulting solution was stirred for 15 min before a solution of the product of Example 51b (9.4 mmol) in CH$_2$Cl$_2$ (83 ml) was added. After the reaction had been stirred 1 hr at −30°, diisopropylethylamine (48.9 g, 380 mmol) was added dropwise; and the reaction mixture was allowed to warm to room temperature before it was washed (1N HCl, 5% aq NaOCl, brine), dried (Na$_2$SO$_4$), filtered, and concentrated under vacuum. The residue was purified by preparative TLC (hexane:Et$_2$O (40:60)) to afford the title product (38%); HPLC, $t_R$=5.21 & 7.31, Col. A, CH$_3$CN:H$_2$O:TFA (50:50:0.1), FR=1.5.

Analysis calculated for: $C_{27}H_{32}F_3N_3O_4 \cdot 0.75H_2O$: C, 60.32; H, 6.37; N, 7.82. Found: C, 60.69; H, 6.21; N, 7.68.

EXAMPLE 52

3(RS)-[4-(Methylsulfonylaminocarbonyl)-phenylaminocarbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)$_2$, $R^3$=4-[CH$_3$S(O$_2$)NHCO]$\phi$, $R^4$=H, A=NHCO, n=1)

Using the method of Example 89, material prepared according to the procedure of Example 16 was allowed to react with methane sulfonamide to provide, after purification by flash chromatography over Baker pH 5.0 silica gel (gradient, CHCl$_3$:MeOH (97:3) to (90:10)), the title product (59%), HPLC, $t_R$=2.60 & 3.33, Col C, H$_2$O:CH$_3$CN (60:40), FR=6.0.

Analysis calculated for: $C_{25}H_{34}F_3N_5O_7S \cdot 0.5H_2O$: C, 48.85; H, 5.74; N, 11.39. Found: C, 49.03; H, 5.74; N, 10.86.

EXAMPLE 53

3(RS)-[2-(4-Morpholinyl)ethoxycarbonyl]-L-valyl-N-[3-(1,1,1-trifluoro-4-methyl-2-oxopentyl)]-L-prolinamide (Formula 1b, $R^1$=CH(CH$_3$)CH$_3$, $R^2$=CH(CH$_3$)$_2$, $R^3$=4-morpholinyl-CH$_2$CH$_2$, $R^4$=H, A=OCO, n=1)

a.

2(RS),3(SR)-[2-(4-Morpholinyl)ethoxycarbonyl]-L-valyl-N-[3-(1,1,1,-trifluoro-2-hydroxy-4-methylpentyl)]-L-prolinamide (Formula VIIb, $R^1$=CH(CH$_3$)CH$_3$, $R^2$=CH(CH$_3$)$_2$, $R^3$=4-morpholinyl—CH$_2$CH$_2$, $R^4$=H, A=OCO, n=1)

Using the method of Example 7b, material prepared by the procedure of Example 3d was allowed to react with material prepared by the procedure of Example 33a to provide the named compound, isolated in 55% yield after purification by flash chromatography (MeOH:CHCl$_3$ (2.5:97.5)); HPLC, $t_R$=4.62 & 5.85, Col. A, CH$_3$CN:H$_2$O (1:1), FR=2.0.

Analysis calculated for: $C_{23}H_{39}F_3N_4O_6 \cdot H_2O$: C, 50.91; H, 7.61; N, 10.32. Found: C, 50.95; H, 7.20; N, 10.02.

b.

3(RS)-[2-(4-Morpholinyl)ethoxycarbonyl]-L-valyl-N-[3-(1,1,1-trifluoro-4-methyl-2-oxopentyl)]-L-prolinamide (Formula Ib, $R^1$=CH(CH)CH$_3$, $R^2$=CH(CH$_3$)$_2$, $R^3$=4-Morpholinyl—CH$_2$CH$_2$, $R^4$=H, A=OCO, n=1)

A solution of DMSO (29.7 g, 380 mmol) in CH$_2$Cl$_2$ (135 ml) was added to a precooled (−43°) solution of oxalyl chloride (24.0 g, 190 mmol) in CH$_2$Cl$_2$ (350 ml) and the resulting solution was stirred for 15 min. before a solution of the product of Example 53a (9.4 mmol) in CH$_2$Cl$_2$ (125 ml) was added. The reaction mixture was allowed to warm from −43° to −20° as it was stirred for one hour; then diisopropylethylamine (48.9 g, 380 mmol) was added dropwise and the reaction mixture was allowed to warm to room temperature before it was further diluted with CH$_2$Cl$_2$, washed (aq NaOH of pH=10), dried (K$_2$CO$_3$/Na$_2$SO$_4$) and concentrated under vacuum. The residue was purified by flash chromatography (MeOH:CHCl$_3$ (2:98)) to afford the title product (18%); HPLC, $t_R$=2.00 & 2.60, Col. A, H$_2$O:CH$_3$CN (1:1), FR=2.0.

Analysis calculated for: $C_{23}H_{37}F_3N_4O_6 \cdot 1.5H_2O$: C, 50.26; H, 7.34; N, 10.19. Found: C, 50.49; H, 6.96; N, 9.96.

EXAMPLE 54

3(RS)-[(2,4-Dichlorophenyl)carbonyl]-L-valyl-N-[3-(1,1,1-trifluoro-4-methyl-2-oxopentyl)]-L-prolinamide (Formula Ib $R^1$=CH(CH$_3$)CH$_3$, $R^2$=CH(CH$_3$)$_2$, $R^3$=2,4-dichloro$\phi$, $R^4$=H A=CO, n=1)

a.

2(RS),3(SR)-[(2,4-Dichlorophenyl)carbonyl]-L-valyl-N-[3-(1,1,1-trifluoro-2-hydroxy-4-methylpentyl)]-L-prolinamide (Formula VIIb, $R^1$=CH(CH$_3$) CH$_3$, $R^2$=CH(CH$_3$)$_2$, $R^3$=2,4-dichloro$\phi$, $R^4$=H, A=CO, n=1)

Using the method of Example 20a, material prepared by the procedure of Example 3d was allowed to react with 2,4-dichlorobenzoyl chloride to provide the title compound, isolated in 98% yield; TLC, $R_f$=0.54, MeOH:CHCl$_3$ (5:95).

b.

3(RS)-[(2,4-Dichlorophenyl)carbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)$_2$, $R^3$=2,4-dichloro$\phi$, $R^4$=H, A=CO, n=1)

A solution of DMSO (29.7 g, 380 mmol) in CH$_2$Cl$_2$ (27 ml) was added slowly to a precooled (−65°) solution of oxalyl chloride (24.0 g, 190 mmol) in CH$_2$Cl$_2$ (350 ml), and the resulting solution was stirred for 15 min before a solution of the product prepared by the method of Example 54a (9.4 mmol) in CH$_2$Cl$_2$ (250 ml) was added. After the reaction had been stirred for 1 hr at −65°, diisopropylethylamine (48.9 g, 380 mmol) was added dropwise; and the reaction mixture was allowed to warm to room temperature before it was washed (1N HCl, brine), dried (Na$_2$SO$_4$), filtered and concentrated under vacuum. The residue was purified by flash chromatography (MeOH:CHCl$_3$ (3:97)) to afford the title product (15%); HPLC, $t_R$=17.93 & 18.55, Col. A, H$_2$O:CH$_3$CN (55:45), FR=2.0.

Analysis calculated for: $C_{23}H_{28}Cl_2F_3N_3O_4 \cdot H_2O$: C, 49.65; H, 5.43; N, 7.55. Found: C, 49.95; H, 5.31; N, 7.35.

EXAMPLE 55

3(RS)-Phenoxycarbonyl-L-valyl-N-[3-(1,1,1-trifluoro-4-methyl-2-oxopentyl)]-L-prolinamide (Formula Ib, $R^1=CH(CH_3)CH_3$, $R^2=CH(CH_3)_2$, $R^3=\phi$, $R^4=H$, A=OCO, n=1)

a.

2(RS),3(SR)-Phenoxycarbonyl-L-valyl-N-[3-(1,1,1-trifluoro-2-hydroxy-4-methylpentyl)]-L-prolinamide (Formula VIIb, $R^1=CH(CH_3)CH_3$, $R^2=CH(CH_3)_2$, $R^3=\phi$, $R^4=H$, A=OCO, n=1)

Using the method of Example 20a, material prepared by the procedure of Example 3d was allowed to react with phenyl chloroformate to provide the title compound, isolated in 61% yield after purification by flash chromatography (MeOH:CHCl$_3$ (5:95)); TLC, $R_f=0.31$ & 0.36, MeOH:CHCl$_3$ (3:97).

b.

3(RS)-Phenoxycarbonyl-L-valyl-N-[3-(1,1,1-trifluoro-4-methyl-2-oxopentyl)]-L-prolinamide (Formula Ib, $R^1=CH(CH_3)CH_3$, $R^2=CH(CH_3)_2$, $R^3=\phi$, $R^4=H$, A=OCO, n=1)

Using the method of Example 54b, the product of Example 55a was oxidized to afford, after purification by flash chromatography (hexane:Et$_2$O (15:85)), the title product (37%); HPLC, $t_R=2.72$ & 3.55, Col A, H$_2$O:CH$_3$CN (1:1), FR=2.0.

Analysis calculated for: $C_{23}H_{30}F_3N_3O_5 \cdot 0.5H_2O$: C, 55.86; H, 6.32; N, 8.50. Found: C, 56.07; H, 6.30; N, 8.48.

EXAMPLE 56

3(RS)-[2-(2-Pyridyl)ethoxycarbonyl]-L-valyl-N-[3-(1,1,1-trifluoro-4-methyl-2-oxopentyl)]-L-prolinamide (Formula Ib, $R^1=CH(CH_3)CH_3$, $R^2=CH(CH_3)_2$, $R^3$=2-pyridyl-CH$_2$CH$_2$, $R^4=H$, A=OCO, n=1)

a.

2(RS),3(SR)-[2-(2-Pyridyl)ethoxycarbonyl]-L-valyl-N-[3-(1,1,1-trifluoro-2-hydroxy-4-methylpentyl)]-L-prolinamide (Formula VIIb, $R^1=CH(CH_3)CH_3$, $R^2=CH(CH_3)_2$, $R^3$=2-pyridyl—CH$_2$CH$_2$, $R^4=H$, A=O, n=1)

Using the method of Example 34b, material prepared by the procedure of Example 3d was allowed to react with material prepared by the procedure of Example 34a to provide the named compound, isolated in 50% yield after purification by flash chromatography (MeOH:CHCl$_3$ (4:96)); TLC, $R_f=0.30$ & 0.34, CHCl$_3$:MeOH (95:5)

b.

3(RS)-[2-(2-Pyridyl)ethoxycarbonyl]-L-valyl-N-[3-(1,1,1-trifluoro-4-methyl-2-oxopentyl)]-L-prolinamide (Formula Ib, $R^1=CH(CH_3)CH_3$, $R^2=CH(CH_3)_2$, $R^3$=2-pyridyl—CH$_2$CH$_2$, $R^4=H$, A=OCO, n=1)

Using the method of Example 54b, with omission of the acid wash, the product of Example 56a was oxidized to afford, after purification by flash chromatography twice (hexane:Et$_2$O (1:1), then MeOH: CHCl$_3$ (5:95)), the title product (19%); HPLC, $t_R=9.52$ & 14.58, Col.A, H$_2$O:CH$_3$CN (60:40), FR=1.0.

Analysis calculated for: $C_{24}H_{33}F_3N_4O_5 \cdot 0.75H_2O$: C, 54.59; H, 6.58; N, 10.61. Found: C, 54.63; H, 6.47; N, 10.55.

EXAMPLE 57

3(RS)-[(4-Fluorophenyl)aminocarbonyl]-L-valyl-N-[3-(1,1,1-trifluoro-4-methyl-2-oxopentyl)]-L-prolinamide (Formula Ib, $R^1=CH(CH_3)CH_3$, $R^2=CH(CH_3)_2$, $R^3$=4-F$\phi$ $R^4=H$, A=NHCO, n=1)

a.

2(RS),3(SR)-[(4-Fluorophenyl)aminocarbonyl]-L-valyl-N-[3-(1,1,1-trifluoro-2-hydroxy-4-methylpentyl)]-L-prolinamide (Formula VIIb, $R^1=CH(CH_3)CH_3$, $R^2=CH(CH_3)_2$, $R^3$=4-F$\phi$, $R^4=H$ A=NHCO n=1)

Using the method of Example 15a, material prepared by the procedure of Example 3d was allowed to react with 4-fluorophenylisocyanate to provide the title compound, isolated in 84% yield after purification by flash chromatography (gradient, MeOH:CHCl$_3$ (2.5:97.5) to (5:95)); TLC, $R_f=0.37$, MeOH:CHCl$_3$ (5:95)

b.

3(RS)-[(4-Fluorophenyl)aminocarbonyl]-L-valyl-N-[3-(1,1,1-trifluoro-4-methyl-2-oxopentyl)]-L-prolinamide (Formula Ib, $R^1=CH(CH_3)CH_3$, $R^2=CH(CH_3)_2$, $R^3$=4-F$\phi$, $R^4=H$, A=NHCO, n=1)

Using the method of Example 54b, the product of Example 57a was oxidized to afford, after purification by flash chromatography (MeOH:CHCl$_3$ (3:97)) the title product (42%); HPLC, $t_R=8.87$ & 12.10, Col A, H$_2$O:CH$_3$CN (60:40), FR=1.0.

Analysis calculated for: $C_{23}H_{30}F_4N_4O_4$: C, 54.97; H, 6.02; N, 11.15. Found: C, 55.18; H, 6.15; N, 11.08.

EXAMPLE 58

3(RS)-[4-(Phenylsulfonylaminocarbonyl)-phenylaminocarbonyl]-L-valyl-N-[3-(1,1,1-trifluoro-4-methyl-2-oxopentyl)]-L-prolinamide (Formula Ib, $R^1=CH(CH_3)CH_3$, $R^2=CH(CH_3)_2$ $R^3$=4-[$\phi$S(O$_2$)NHCO]$\phi$, $R^4=H$, A=NHCO, n=1)

Using the method of Example 89, material prepared according to the procedure of Example 16 was allowed to react with benzene sulfonamide to provide, after purification by flash chromatography on Baker pH 5.0 silica gel (CHCl$_3$:MeOH (97:3)), the title product (42%); HPLC, $t_R=4.05$ & 5.93, Col C, H$_2$O:CH$_3$CN (60:40), FR=6.0.

Analysis calculated for: $C_{30}H_{36}F_3N_5O_7 \cdot 0.5H_2O$: C, 53.25; H, 5.51; N, 10.34. Found: C, 53.38; H, 5.61; N, 10.02.

EXAMPLE 59

3(RS)-[2-(3-Thiophenyl)ethoxycarbonyl]-L-valyl-N-[3-(1,1,1-trifluoro-4-methyl-2-oxopentyl)]-L-prolinamide (Formula Ib $R^1=CH(CH_3)CH_3$, $R^2=CH(CH_3)_2 R^3$=3-thiophenyl-CH$_2$CH$_2$, $R^4=H$, A=OCO, n=1)

a. 4-Nitrophenyl 2-(3-thiophenyl)ethyl carbonate

Using the method of Example 7a, 3-thiopheneethanol was treated with 4-nitrophenyl chloroformate to afford, after purification by flash chromatography (EtOAc:hexane (1:9)), the title product (56%); TLC, $R_f=0.25$, EtOAc:hexane (1:9).

b.
2(RS),3(SR)-[2-(3-Thiophenyl)ethoxycarbonyl]-L-valyl-N-[3-(1,1,1-trifluoro-2-hydroxy-4-methylpentyl)]-L-prolinamide (Formula VIIb, $R^1$=CH(CH$_3$)CH$_3$, $R^2$=CH(CH$_3$)$_2$, $R^3$=3-thiophenyl—CH$_2$CH$_2$, $R^4$=H, A=O, n=1)

Using the method of Example 7b, material prepared by the procedure of Example 3d was allowed to react with the product of Example 59a to provide the title compound, isolated in 58% yield after purfication by flash chromatography (acetone: hexane (3:7)); TLC, $R_f$=0.23 & 0.27, MeOH:CHCl$_3$ (5:95).

Analysis calculated for: C$_{24}$H$_{34}$F$_3$N$_3$O$_5$S: C, 52.96; H, 6.57; N, 8.06. Found: C, 53.28; H, 6.46; N, 7.77.

c.
3(RS)-[2-(3-Thiophenyl)ethoxycarbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)$_2$, $R^3$=3-thiophenyl—CH$_2$CH$_2$, $R^4$=H, A=OCO, n=1)

A solution of DMSO (29.7 g, 380 mmol) in CH$_2$Cl$_2$ (135 ml) was added slowly to a precooled (−43°) solution of oxalyl chloride (24.0 g, 190 mmol) in CH$_2$Cl$_2$ (350 ml). The resulting solution was stirred 15 min before a solution of material prepared by the method of Example 59b (9.4 mmol) in CH$_2$Cl$_2$ (125 ml) was added and the reaction was stirred at −43° for an additional hour. Diisopropylethylamine (48.9 g, 380 mmol) was added dropwise, and the reaction mixture was allowed to warm to room temperature before it was washed (1N aq HCl, 5% aq NaOCl, brine), dried (Na$_2$SO$_4$), filtered, and concentrated under vacuum. Purification of the residue by flash chromatography (acetone:hexane (1:4)) afforded the title product (23%); HPLC, $t_R$=5.09 & 7.61, Col A, H$_2$O:CH$_3$CN (1:1), FR=2.0.

Analysis calculated for: C$_{24}$H$_{32}$F$_3$N$_3$O$_5$S: C, 53.17; H, 6.21; N, 8.09. Found: C, 52.92; H, 6.26; N, 8.09.

EXAMPLE 60

3(RS)-(1,1-Dimethylethoxycarbonyl)-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_2$CH$_3$, $R^3$=CH$_3$C(CH$_9$)$_9$, $R^4$=H, A=OCO, n=1)

a.
2(RS),3(SR)-(1,1-Dimethylethoxycarbonyl)-L-α-aminobutyryl-N-[3-(1,1,1-trifluoro-2-hydroxy-4-methylpentyl)]-L-prolinamide (Formula VIIb, $R^1$=CH(CH$_3$)CH$_3$, $R^2$=CH$_2$CH$_3$, $R^3$=CH$_3$C(CH$_3$)$_2$, $R^4$=H, A=OCO, n=1)

DCC (5.90 g, 28.7 mmol) was added to a stirred solution of HOBT (7.76 g, 57.4 mmol), BOC-α-aminobutanoic acid (5.60 g, 27.4 mmol), and material prepared by the procedure of Example 2b (7.00 g, 26.1 mmol) in dry THF (130 ml) at 0° under nitrogen. After the resulting reaction mixture had been stirred at 0° for 1 hr, it was allowed to warm to room temperature and was stirred overnight. The reaction mixture was filtered; and the filtrate was concentrated under vacuum to a residue which was redissolved in EtOAc. The resulting solution was washed satd NaHCO$_3$ brine), dried (Na$_2$SO$_4$), filtered, and concentrated under vacuum to a residue which was purified by flash chromatography (EtOAc:CH$_2$Cl$_2$ (1:3)) to give the title compound (95%); TLC, $R_f$=0.29, EtOAc:CH$_2$Cl$_2$ (3:7).

b.
3(RS)-(1,1-Dimethylethoxycarbonyl)-L-e-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_2$CH$_3$, $R^3$=CH$_3$C(CH$_3$)$_2$, $R^4$=H, A=OCO, n=1)

Using the method of Example 61c the product of Example 60a was oxidized to afford, after purification by flash chromatography (MeOH:CHCl$_3$ (1.5:98.5), the title product (47%); HPLC, $t_R$=10.21 & 14.54, Col A, H$_2$O:CH$_3$CN (65:35), FR=2.0.

Analysis calculated for: C$_{20}$H$_{32}$F$_3$N$_3$O$_5$: C, 53.21; H, 7.14; N, 9.31. Found: C, 53.65; H, 7.21; N, 9.51.

EXAMPLE 61

3(RS)-[1-Oxo-2-(2-thiophenyl)ethyl]-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_2$CH$_3$, $R^3$=(2-thiophenyl)CH$_2$, $R^4$=H, A=CO, n=1)

a.
2(RS),3(SR)-L-α-aminobutyryl-N-[3-(1,1,1-trifluoro-2-hydroxy-4-methylpentyl)]-L-prolinamide trifluoroacetic acid salt (Formula IVb, $R^1$=CH(CH$_3$)CH$_3$, $R^2$=CH$_2$CH$_3$, $R^4$=H, n=1)

A solution of material prepared by the procedure of Example 60a (4.0 g, 8.84 mmol) and TFA (32 ml, 415 mmol) in CH$_2$Cl$_2$ (32 ml) was stirred at room temperature for 22 hr before the solvents were removed under reduced pressure to afford the crude product (5 g, >100%) as a colorless glass which was used without further purification or characterization.

b.
2(RS),3(SR)-N-[3-(1,1,1-trifluoro-2-hydroxy-4-methylpentyl)]-L-prolinamide (Formula VIIb, $R^1$=CH(CH$_3$)CH$_3$, $R^2$=CH$_2$CH$_3$, $R^3$=(2-thiophenyl)CH$_2$, $R^4$=H, A=CO, n=1)

DCC (0.315 g, 1.53 mmol) was added to a stirred solution of HOBT (0.413 g, 3.06 mmol) 2-thiopheneacetic acid (0.222 g, 1.53 mmol), NMM (0.154 g, 1.53 mmol), and material prepared according to Example 61a (0.650 g, 1.39 mmol) in dry THF (20 ml) at 0° under nitrogen. After the resulting reaction mixture had been stirred at 0° for 1 hr, it was allowed to warm to room temperature and was stirred overnight. The reaction mixture was filtered; and the filtrate was concentrated under vacuum to a residue which was dissolved in EtOAc. The resulting solution was washed (brine), dried (Na$_2$SO$_4$), filtered, and concentrated under vacuum to a residue which was purified by flash chromatography (acetone:hexane (1:1)) to give of the title compound (33%); TLC, $R_f$=0.40 & 0.44, MeOH:CHCl$_3$ (1:9).

Analysis calculated for: C$_{21}$H$_{30}$F$_3$N$_3$O$_4$S: C, 52.82; H, 6.33; N, 8.80. Found: C, 52.43; H, 6.53; N, 8.08.

c.
3(RS)-N-[3-(1,1,1-trifluoro-4-methyl-2-oxopentyl)]-L-prolinamide (Formula Ib, $R^1$=CH(CH$_3$)CH$_3$, $R^2$=CH$_2$CH$_3$, $R^3$=(2-thiophenyl)CH$_2$, $R^4$=H, A=C$_0$, n=1)

To a suspension of CRO$_3$(0.84 g, 8.4 mmol) in dry CH$_2$Cl$_2$ (50 ml) was added dry pyridine (1.36 ml, 17 mmol), and the mixture stirred at room temperature for 30 min. To the resulting burgundy colored suspension was added 1 g of Celite ® followed by the product from Example 61b (0.20 g, 0.42 mmol) in $CH_2Cl_2$ (5 ml). The mixture was stirred until TLC indicated all the alcohol was consumed. The mixture was then filtered through a pad of silica gel with methanol:chloroform (1:9) and the solvents removed from the filtrate under vacuum. The crude product was purified by preparative TLC (MeOH:$CHCl_3$ (5:95)) to afford the product (150 mg) as a white solid; HPLC, $t_R$=4.18 & 5.65, Col A, $H_2O$: $CH_3CN$ (60:40), FR=2.0.

Analysis calculated for: $C_{21}H_{28}F_3N_3O_4S.0.5H_2O$: C, 52.06; H, 6.03; N, 8.67. Found: C, 52.03; H, 6.19; N, 8.38.

EXAMPLE 62

3(RS)-(Phenylmethoxycarbonyl)-L-α-aminobutyryl-N-[3-(1,1,1-trifluoro-4-methyl-2-oxopentyl)]-L-prolinamide (Formula Ib, $R^1$=CH($CH_3$)$CH_3$, $R^2$=$CH_2CH_3$, $R^3$=φ$CH_2$, $R^4$=H, A=OCO, n=1)

a.

2(RS),3(SR)-(Phenylmethoxycarbonyl)-L-α-aminobutyryl-N-[3-(1,1,1-trifluoro-2-hydroxy-4-methylpentyl)]-L-prolinamide (Formula VIIb, $R^1$=CH($CH_3$)$CH_3$, $R^2$=$CH_2CH_3$, $R^3$=φ$CH_2$, $R^4$=H, A=OCO, n=1)

Using the method of Example 20a, material prepared according to the procedure of Example 61a was allowed to react with 1.5 equivalents of benzyl chloroformate in one-fourth the amount of $CHCl_3$ used in the method of Example 20a to produce the title compound, isolated in 51% yield after purification by flash chromatography (acetone:hexane (1:4)); TLC, $R_f$=0.38 & 0.43, acetone:hexane (40:60).

b.

3(RS)-(Phenylmethoxycarbonyl)-L-α-aminobutyryl-N-[3-(1,1,1-trifluoro-4-methyl-2-oxopentyl)]-L-prolinamide (Formula Ib, $R^1$=CH($CH_3$)$CH_3$, $R^2$=$CH_2CH_3$, $R^3$=φ$CH_2$, $R^4$=H, A=OCO, n=1)

Using the method of Example 61c the product of Example 62a was oxidized to afford, after purification by flash chromatography (acetone: hexane (30:70)), the title product (64%); HPLC, $t_R$=5.69 & 7.75, Col A, $H_2O$:$CH_3CN$ (55:45), FR=2.0.

Analysis calculated for: $C_{23}H_{30}F_3N_3O_5.0.80H_2O$: C, 55.26; H, 6.37; N, 8.40. Found: C, 55.10; H, 6.19; N, 8.77.

EXAMPLE 63

3(RS)-(Phenoxy carbonyl)-L-α-aminobutyryl-N-[3-(1,1,1-trifluoro-4-methyl-2-oxopentyl)]-L-prolinamide (Formula Ib, $R^1$=CH($CH_3$)$CH_3$, $R^2$=$CH_2CH_3$, $R^3$=φ, $R^4$=H, A=OCO, n=1)

a.

2(RS),3(SR)-(Phenoxycarbonyl)-L-α-aminobutyryl-N-[3-(1,1,1-trifluoro-2-hydroxy-4-methylpentyl)]-L-prolinamide (Formula VIIb, $R^1$=CH($CH_3$)$CH_3$, $R^2$=$CH_2CH_3$, $R^3$=φ, $R^4$=H, A=OCO, n=1)

Using the method of Example 20a, but using NMM instead of TEA, material prepared according to the procedure of Example 61a was allowed to react with 1.5 equivalents of phenyl chloroformate to produce the title compound, isolated in 18% yield after purification by preparative TLC (acetone:hexane (3:7)); TLC, $R_f$=0.32 & 0.37, acetone:hexane (3:7).

b.

3(RS)-(Phenoxycarbonyl)-L-α-aminobutyryl-N-[3-(1,1,1-trifluoro-4-methyl-2-oxopentyl)]-L-prolinamide (Formula Ib, $R^1$=CH($CH_3$)$CH_3$, $R^2$=$CH_2CH_3$, $R^3$=φ, $R^4$=H, A=OCO, n=1)

Using the method of Example 61c, the product of Example 63a was oxidized to afford, after purification by flash chromatography (EtOAc: hexane (1:9)), the title product (60%); HPLC, $t_R$=4.57 & 6.51, Col A, $H_2O$:$CH_3CN$ (55:45).

Analysis calculated for: $C_{22}H_{28}F_3N_3O_5$: C, 56.04; H, 5.98; N, 8.90. Found: C, 56.04; H, 6.18; N, 8.85.

EXAMPLE 64

3(RS)-[4-(1-Oxoethylamino)phenylsulfonyl]-L-valyl-N-[3-(1,1,1-trifluoro-4-methyl-2-oxopentyl)]-L-prolinamide (Formula Ib, $R^1$=CH($CH_3$)$CH_3$, $R^2$=CH($CH_3$)$CH_3$, $R^3$=4—($CH_3$CONH)φ, $R^4$=H, A=S($O_2$), n=1)

a.

2(RS),3(SR)-[4-(1-Oxoethylamino)phenylsufonyl]-L-valyl-N-[3-(1,1,1-trifluoro-2-hydroxy-4-methylpentyl)]-L-prolinamide (Formula VIIb, $R^1$=CH($CH_3$)$CH_3$, $R^2$=CH($CH_3$)$CH_3$, $R^3$=4-($CH_3$CONH)φ, $R^4$=H, A=S($O_2$), n=1)

To a stirred solution of material prepared according to Example 3d (1.00 g, 2.72 mmol) and NMM (0.28 g, 0.30 ml, 2.80 mmol) in $CH_2Cl_2$ (50 ml) under $N_2$ was added 4-acetamidobenzenesulfonyl chloride (0.64 g, 2.72 mmol). After stirring the reaction mixture overnight at room temperature, the solution was washed (5% aq citric acid, brine), dried ($Na_2SO_4$), filtered, and concentrated to leave an orange syrup which was flash chromatagraphed over silica gel (350 g) (MeOH: $CHCl_3$ (7:93)) to give the title product (810 mg, 52.60%); TLC, $R_f$=0.34 & 0.45, MeOH:$CHCl_3$ (7:93).

b.

3(RS)-[4-(1-Oxoethylamino)phenylsufonyl]-L-valyl-N-[3-(1,1,1-trifluoro-4-methyl-2-oxopentyl)]-L-prolinamide (Formula Ib, $R^1$=CH($CH_3$)$CH_3$, $R_2$=CH($CH_3$)$CH_3$, $R^3$=4-($CH_3$CONH)φ, $R^4$=H, A=S($O_2$), n=1)

Using the method of Example 31c, the product of Example 64a was oxidized to afford, after purification by flash chromatography (MeOH:$CHCl_3$ (5:95)), the title product (84%); HPLC, $t_R$=3.22 & 4.58, Col A, $CH_3CN$:$H_2O$ (40:60), FR=2.0.

Analysis calculated for: $C_{24}H_{33}F_3N_4O_6S.H_2O$: C, 49.65; H, 6.08; N, 9.65. Found: C, 49.73; H, 5.86; N, 9.53.

EXAMPLE 65

3(RS)-$N^2$-(1,1-Dimethylethoxycarbonyl)-$N^6$-phenylmethoxycarbonyl-L-lysyl-N-[3-(1,1,1-trifluoro-4-methyl-2-oxopentyl)]-L-prolinamide (Formula Ib, $R^1$=CH(CH$_3$)CH$_3$, $R^2$=$\phi$CH$_2$OCONH(CH$_2$)$_4$, $R^3$=(CH$_3$)$_3$C, $R^4$=H, A=OCO, n=1)

a.

2(RS),3(SR)-$N^2$-(1,1-Dimethylethoxycarbonyl)-$N^6$-phenylmethoxycarbonyl-L-lysyl-N-[3-(1,1,1-trifluoro-2-hydroxy-4-methylpentyl)]-L-prolinamide (Formula VIIb, $R^1$=CH(CH$_3$)CH$_3$, $R^2$=$\phi$CH$_2$OCONH(CH$_2$)$_4$, $R^3$=(CH$_3$)$_3$C, $R^4$=H, A=OCO, n=1)

Using the method of Example 84b, $N^2$-BOC-$N^6$-CBZ-L-lysine was allowed to react with material prepared by the method of Example 2b to provide, after purification by flash chromatography (gradient elution, MeOH:CHCl$_3$ (2.5:97.5) to (5:95)), the title product (73%); TLC, $R_f$=0.57, MeOH:CHCl$_3$ (5:95).

b.

3(RS)-$N^2$-(1,1-Dimethylethoxycarbonyl)-$N^6$-phenylmethoxycarbonyl-L-lysyl-N-[3-(1,1,1-trifluoro-4-methyl-2-oxopentyl)]-L-prolinamide (Formula Ib, $R^1$=CH(CH$_3$)CH$_3$, $R^2$=$\phi$CH$_2$OCONH(CH$_2$)$_4$, $R^3$=(CH$_3$)$_3$C, $R^4$=H, A=OCO, n=1)

Using the method of Example 31c, the product of Example 65a was oxidized to afford, after purification by flash chromatography (gradient elution, MeOH: CHCl$_3$ (2.5:97.5) to (5:95)), the title product (65%); HPLC, $t_R$=4.15 & 5.14, Col A, H$_2$O:CH$_3$CN (45:55), FR=2.0.

Analysis calculated for: C$_{30}$H$_{43}$F$_3$N$_4$O$_7$.0.5H$_2$O: C, 56.51; H, 6.95; N, 8.79. Found: C, 56.45; H, 6.58; N, 8.42.

EXAMPLE 66

3(RS)-[(2-Amino-5-chlorophenyl)carbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)$_2$—, $R^3$=2-NH$_2$-5-Cl-$\phi$, $R^4$=H, A=CO, n=1)

a.

2(RS),3(SR)-[(2-Amino-5-chlorophenyl)carbonyl]-L-valyl-N-[3-(1,1,1-trifluoro-2-hydroxy-4-methylpentyl)]-L-prolinamide (Formula VIIb, $R^1$=CH(CH$_3$)CH$_3$, $R^2$=CH(CH$_3$)$_2$, $R^3$=2—NH$_2$-5-Cl-$\phi$, $R^4$=H, A=CO, n=1)

A solution of material prepared according to Example 3d (1 g, 2.7 mmol) in CH$_2$Cl$_2$ (50 ml) was treated with 5-chloroisotoic anhydride (0.54 g, 2.7 mmol) at room temperature and the mixture was stirred overnight before it was washed (5% aqueous NaHCO$_3$, brine), dried (Na$_2$SO$_4$), concentrated under vacuum, and purified by flash chromatography (MeOH:CHCl$_3$ (3:97)) to give the title product (1.4 g, 78%) as a white foam; TLC, $R_f$=0.30 & 0.25, MeOH:CHCl$_3$ (5:95).

b.

3(RS)-[(2-Amino-5-chlorophenyl)carbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)$_2$, $R^3$=2-NH$_2$-5-Cl-$\phi$, $R^4$=H, A=CO, n=1)

Using the method of Example 31c, the product of Example 66a was oxidized to afford, after purification by flash chromatography (MeOH:CHCl$_3$ (3:97)), the title product (76%); HPLC, $t_R$=3.41 & 4.62, Col A, H$_2$O:CH$_3$CN (50:50), FR=2.0.

Analysis calculated for: C$_{23}$H$_{30}$F$_3$N$_4$O$_4$.H$_2$O: C, 51.45; H, 6.01; N, 10.43. Found: C, 51.65; H, 5.74; N, 9.68.

EXAMPLE 67

3(RS)-(4-Methoxyphenylcarbonyl)-L-$\alpha$-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_2$CH$_3$, $R^3$=4-(CH$_3$O)—$\phi$, $R^4$=H, A=CO, n=1)

a.

2(RS),3(SR)-(4-Methoxyphenylcarbonyl)-L-$\alpha$-aminobutyryl-N-[3-(1,1,1-trifluoro-2-hydroxy-4-methylpentyl)]-L-prolinamide (Formula VIIb, $R^1$=CH(CH$_3$)CH$_3$, $R^2$=CH$_3$CH$_2$, $R^3$=4-(CH$_3$O)—$\phi$, $R^4$=H, A=CO, n=1)

Using the method of Example 20a, material prepared according to the procedure of Example 61a was allowed to react with 4-methoxybenzoylchloride to provide the title compound, isolated in 34% yield after purification by flash chromatography (EtOAc:hexane (60:40)), TLC, $R_f$=0.71 & 0.73, MeOH:CHCl$_3$ (1:9).

Analysis calculated for: C$_{23}$H$_{32}$F$_3$N$_3$O$_5$.0.3H$_2$O: C, 56.04; H, 6.67; N, 8.52. Found: C, 56.06; H, 6.60; N, 8.14.

b.

3(RS)-(4-Methoxyphenylcarbonyl)-L-$\alpha$-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$, $R^3$=4-(CH$_3$O)—$\phi$, $R^4$=H, A=CO, n=1).

Using the method of Example 61c, except the alcohol was dissolved in five times the solvent, the product of Example 67a was oxidized to afford, after purification by preparative TLC (MeOH: CHCl$_3$ (1:9)), the title product (40%); HPLC, $t_R$=8.89 & 11.75, Col A, H$_2$O:CH$_3$CN (70:30), FR=2.0.

Analysis calculated for: C$_{23}$H$_{30}$F$_3$N$_3$O$_5$.H$_2$O: C, 54.86; H, 6.41; N, 8.35. Found: C, 54.89; H, 6.38; N, 7.48.

EXAMPLE 68

3(RS)-[2-(Tricylo[3.3.1.1$^{3,7}$]-dec-1-yl)ethoxycarbonyl]-L-$\alpha$-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$—, $R^3$=(1-adamantyl)-CH$_2$CH$_2$, $R^4$=H, A=OCO, n=1)

a.

2(RS),3(SR)-[2-(Tricylco[3.3.1.1$^{3,7}$]-dec-1-yl)ethoxycarbonyl]-L-$\alpha$-aminobutyryl-N-[3-(1,1,1-trifluoro-2-hydroxy-4-methylpentyl)]-L-prolinamide (Formula VIIb, $R^1$=CH(CH$_3$)CH$_3$, $R^2$=CH$_3$CH$_2$, $R^3$=(1-adamantyl)-CH$_2$CH$_2$, $R^4$=H, A=OCO, n=1)

Using the method of Example 34b, material prepared according to the procedure of Example 61a was allowed to react with material prepared according to Example 7a to provide the title compound, isolated in 42% yield after purification by flash chromatography (EtOAc:hexane (20:80), then (50:50)); TLC, $R_f$=0.33 & 0.44, MeOH:CHCl$_3$ (5.95).

b.
3(RS)-[2-(Tricyclo[3.3.1.1$^{3,7}$]-dec-1-yl)ethoxycarbonyl]-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$, $R^3$=(1-adamantyl)-CH$_2$CH$_2$, $R^4$=H, A=OCO, n=1)

Using the method of Example 61c, the product of Example 68a was oxidized to afford, after purification by flash chromatography (Et$_2$O:hexane (50:50), then (90:10)), the title product (66%); HPLC, $t_R$=4.64 & 5.63, Col A, H$_2$O:CH$_3$CN (25:75), FR=2.0.

Analysis calculated for: C$_{28}$H$_{42}$F$_3$N$_3$O$_5$.0.15H$_2$O: C, 60.01; H, 7.60. Found: C, 59.76; H, 7.65.

EXAMPLE 69

3(RS)-N$^2$-(1,1-Dimethylethoxycarbonyl)-N$^6$-phenylsulfonyl-L-lysyl-N-[3-(1,1,1-trifluoro-4-methyl-2-oxopentyl)]-L-prolinamide (Formula Ib, $R^1$=CH(CH$_3$)CH$_3$, $R^2$=φS(O$_2$)NH(CH$_2$)$_4$, $R^3$=(CH$_3$)$_3$C, $R^4$=H, A=OCO, n=1)

a.
2(RS),3(SR)-N$^2$-(1,1-Dimethylethoxycarbonyl)-L-lysyl-N-[3-(1,1,1-trifluoro-2-hydroxy-4-methylpentyl)]-L-prolinamide (Formula VIIb, $R^1$=CH(CH$_3$)CH$_3$, $R^2$=H$_2$N(CH$_2$)$_4$ $R^3$=(CH$_3$)$_3$C, $R^4$=H, A=OCO, n=1)

To a solution of material prepared according to Example 65a (3.0 g, 4.8 mmol) in absolute EtOH (60 ml) was added 10% Pd on carbon (0.6 g). The resulting suspension was stirred overnight under an atmosphere (102,325 Pascals) of H$_2$. Additional 10% Pd on carbon (0.3 g) was added, and stirring was continued for several hours. The reaction was filtered through Celite ® and concentrated under vacuum to give the product (2.48 g), which was used directly.

b.
2(RS),3(SR)-N$^2$-(1,1-Dimethylethoxycarbonyl)-N$^6$-phenylsulfonyl-L-lysyl-N-[3-(1,1,1-trifluoro-2-hydroxy-4-methylpentyl)]-L-prolinamide (Formula VIIb, $R^1$=CH(CH$_3$)CH$_3$, $R^2$=φS(O$_2$)NH(CH$_2$)$_4$, $R^3$=(CH$_3$)$_3$C, $R^4$=H, A=OCO, n=1)

Using the method of Example 72b, except NMM was used instead of TEA, the product of Example 69a was treated with benzene sulfonyl chloride to produce the title product, purified by flash chromatography (CHCl$_3$:MeOH (95:5)), in 69% yield; TLC, $R_f$=0.29, MeOH:CHCl$_3$ (95:5).

c.
3(RS)-N$^2$-(1,1-Dimethylethoxycarbonyl)-N$^6$-phenylsulfonyl-L-lysyl-N-[3-(1,1,1-trifluoro-4-methyl-2oxopentyl)]-L-prolinamide (Formula Ib, $R^1$=CH(CH$_3$)CH$_3$, $R^2$=φS(O$_2$)NH(CH$_2$)$_4$, $R^3$=(CH$_3$)$_3$C, $R^4$=H, A=OCO, n=1)

Using the method of Example 31c, the product of Example 69b was oxidized to afford, after purification by flash chromatography (gradient elution, MeOH:CHCl$_3$ (0:100) to (2.5:97.5)), the title product (57%); HPLC, $t_R$=7.48 & 9.11, Col A, CH$_3$CN:H$_2$O (1:1), FR=1.0.

Analysis calculated for: C$_{28}$H$_{16}$F$_3$N$_4$O$_7$S.H$_2$O: C, 51.52; H, 6.64; N, 8.58. Found: C, 51.47; H, 6.46; N, 7.80.

EXAMPLE 70

3(RS)-(4-Ethoxycarbonylphenyl)aminocarbonyl-L-α-aminobutanoyl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$, $R^3$=4-[CH$_3$CH$_2$OC(O)]φ, $R^4$=H, A=NHCO, n=1)

a.
2(RS),3(SR)-(4-Ethoxycarbonylphenyl)aminocarbonyl-L-α-aminobutyroyl-N-[3-(1,1,1-trifluoro-2-hydroxy-4-methylpentyl)]-L-prolinamide (Formula VIIb, $R^1$=CH(CH$_3$)CH$_3$, $R^2$=CH$_3$CH$_2$, $R^3$=4-[CH$_3$CH$_2$OC(O)]φ, $R^4$=H, A=NHCO, n=1)

Using the method of Example 15a, material prepared according to the procedure of Example 61a was allowed to react with ethyl 4-iso-cyanatobenzoate to provide the title compound, isolated in 46% yield; TLC, $R_f$=0.53, MeOH:CHCl$_3$ (5:95).

b.
3(RS)-(4-Ethoxycarbonylphenyl)aminocarbonyl-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$, $R^3$=4-[CH$_3$CH$_2$OC(O)]φ, $R^4$=H, A=NHCO, n=1)

Using the method of Example 61c, the product of Example 70a was oxidized to afford, after purification by flash chromatography (CHCl$_3$: MeOH (97:3)), the title product (68%); HPLC, $t_R$=6.35 & 8.70, Col A, H$_2$O: CH$_3$CN (60:40), FR=2.0.

Analysis calculated for: C$_{25}$H$_{33}$F$_3$N$_4$O$_6$.0.5H$_2$O: C, 54.44; H, 6.21; N, 10.15. Found: C, 54.76; H, 6.13; N, 10.27.

EXAMPLE 71

3(RS)-(4-Hydroxycarbonylphenyl)aminocarbonyl-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$, $R^3$=4[HOC(O)]φ, $R^4$=H, A=NHCO, n=1)

Using the method of Example 14, material prepared according to the procedure of Example 70b was converted into the title product and isolated by flash chromatography on Baker pH 5.0 silica gel (CHCl$_3$:MeOH (97:3)) in 61% yield; HPLC, $t_R$=3.68 & 4.69, Col A, H$_2$O:CH$_3$CN (3:1), FR=2.0.

Analysis calculated for: C$_{23}$H$_{29}$F$_3$N$_4$O$_6$.H$_2$O: C, 51.88; H, 5.86; N, 10.52. Found: C, 51.98; H, 5.69; N, 10.19.

EXAMPLE 72

3(RS)-N$^6$-Phenylmethoxycarbonyl-N$^2$-phenylsulfonyl-L-lysyl-N-[3-(1,1,1-trifluoro-4-methyl-2-oxopentyl)]-L-prolinamide (Formula Ib, $R^1$=CH(CH$_3$)CH$_3$, $R^2$=(CH$_2$)$_4$NHCOOCH$_2$φ, $R^3$=φ, $R^4$=H, A=S(O$_2$), n=1)

a. 2(RS),3(SR)-N-Phenylmethoxycarbonyl-L-lysyl-N-[3-(1,1,1-trifluoro-4-methyl-2-oxopentyl)]-L-prolinamide trifluoroacetic acid salt (Formula IVb, $R^1$=CH(CH$_3$)CH$_3$, $R^2$=φCH$_2$OCONH(CH$_2$)$_4$—, $R^4$=H, n=1)

To a solution of product prepared according to the procedure of Example 65a (2.75 g, 4.4 mmol) in CH$_2$Cl$_2$ (7 ml) was added TFA (10.4 g, 90 mmol), and the solution was stirred at room temperature for 1 hr. Toluene (10 ml) was added, and the reaction mixture was concentrated under vacuum to afford the title product (3.4 g) which was used without further purification.

b. 2(RS),3(SR)-$N^6$-Phenylmethoxycarbonyl-$N^2$-phenyl-sulfonyl-L-lysyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_2$)$_4$NHC(O)OCH$_2\phi$, $R^3$=$\phi$, $R^4$=H, A=S(O$_2$), n=1)

To a solution of the product of Example 72a (0.83 g, 1.3 mmol) in CH$_2$Cl$_2$ (6.5 ml) were added TEA (0.39 g, 3.9 mmol) and benzenesulfonyl chloride (0.25 g, 1.4 mmol), and the reaction mixture was stirred overnight at room temperature. After the reaction mixture was concentrated under vacuum, the residue was dissolved in EtOAc. The EtOAc solution was filtered and concentrated under vacuum to a residue which was purified by flash chromatography (gradient elution, MeOH:CHCl$_3$ (2.5:97.5) to (5:95)) to give the title product (81%); TLC, R$_f$=0.52, MeOH:CHCl$_3$ (5:95).

c. 3(RS)-$N^6$-Phenylmethoxycarbonyl-$N^2$-phenylsulfonyl-L-lysyl-N-[3-(1,1,1,-trifluoro-4-methyl-2-oxopentyl)]-L-prolinamide (Formula Ib, $R^1$=CH(CH$_3$)CH$_3$, $R^2$=(CH$_2$)$_4$NHC(O)OCH$_2\phi$, $R^3$=$\phi$, $R^4$=H, A=S(O$_2$), n=1)

Using the method of Example 31c, the product of Example 72b was oxidized to afford, after purification by flash chromatography (gradient elution, CHCl$_3$ to CHCl$_3$:MeOH (97.5:2.5)), the title product (63%); HPLC, t$_R$=5.0 & 6.3, Col A, CH$_3$CN:H$_2$O (3:2), FR=1.0.

Analysis calculated for: C$_{31}$H$_{39}$F$_3$N$_4$O$_7$S. H$_2$O: C, 54.22; H, 6.02; N, 8.16. Found: C, 54.17; H, 5.80; N, 7.86.

EXAMPLE 73

3(RS)-[2-(2-Methoxyethoxy)ethoxycarbonyl]-L-$\alpha$-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$—, $R^3$=CH$_3$O(CH$_2$)$_2$O(CH$_2$)$_2$, $R^4$=H, A=OCO n=1)

a. 2(RS),3(SR)-[2-(2-Methoxyethoxy)ethoxycarbonyl]-L-$\alpha$-aminobutyryl-N-[3-(1,1,1-trifluoro-2-hydroxy-4-methylpentyl)]-L-prolinamide (Formula VIIb, $R^1$=CH(CH$_3$)CH$_3$, $R^2$=CH$_3$CH$_2$—, $R^3$=CH$_3$O(CH$_2$)$_2$O(CH$_2$)$_2$, $R^4$=H, A=OCO, n=1)

Using the method of Example 34b, material prepared according to the procedure of Example 61a was allowed to react with material prepared according to the procedure of Example 19a to provide the title compound, isolated in 75% yield after purification by flash chromatography (gradient, acetone:hexane (1:9) to (7:3)), TLC, R$_f$=0.30 & 0.35, acetone:hexane (40:60).

Analysis calculated for: C$_{17}$H$_{29}$F$_3$N$_2$O$_6$.0.5H$_2$O: C, 48.22; H, 7.14; N, 6.61. Found: C, 48.13; H, 6.90; N, 6.07.

b. 3(RS)-[2-(2-Methoxyethoxy)ethoxycarbonyl]-L-$\alpha$-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$, $R^3$=CH$_3$O(CH$_2$)$_2$)$_2$, $R^4$=H, A=OCO, n=1)

Using the method of Example 61c the product of Example 73a was oxidized to afford, after purification by flash chromatography (gradient elution, EtOAc:hexane (1:1) to EtOAc to acetone:EtOAc (1:9)), the title product (40%); HPLC, t$_R$=5.70 & 8.95, Col A, H$_2$O:CH$_3$CN (75:25), FR=2.0.

Analysis calculated for: C$_{21}$H$_{34}$F$_3$N$_3$O$_7$: C, 48.77; H, 7.14; N, 6.61. Found: C, 48.13; H, 6.90; N, 6.09.

EXAMPLE 74

3(RS)-[Z-(4-Aminocarbonylamino-1,4-dioxo-2-butenyl)]-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$Z—H$_2$NC(O)NHC(O)CH=CH—, $R^4$=H, A=CO, n=1)

a. 2(RS),3(SR)-[Z-(4-Aminocarbonylamino-1,4-dioxo-2-butenyl)]-L-valyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_3$)$_2$CH—, $R^3$=Z—H$_2$NC(O)NHC(O)CH=CH—, $R^4$=H, A=CO, n=1)

Using the method of Example 21b, material prepared by the procedure of Example 3d was allowed to react with Z-4-aminocarbonylamino-4-oxo-2-butenoic acid to provide the title compound, isolated in 26% yield after purification by flash chromatography (MeOH:CHCl$_3$ (5:95)); TLC, R$_f$=0.17 & 0.25, MeOH:CHCl$_3$ (5:95).

b. 3(RS)-[Z-(4-Aminocarbonylamino-1,4-dioxo-2-butenyl)]-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=Z—H$_2$NC(O)NHC(O)CH=CH—, $R^4$=H, A=CO, n=1)

Using the method of Example 31c, the product of Example 74a was oxidized to afford, after purification by flash chromatography (MeOH:CHCl$_3$ (4:96)), the title product (29%); HPLC, t$_R$=1.78 & 2.45, Col A, H$_2$O:CH$_3$CN (65:35), FR=2.0.

Analysis calculated for: C$_{21}$H$_{30}$F$_3$N$_5$O$_6$.1.5H$_2$O: C, 47.37; H, 6.25; N, 13.15. Found: C, 47.29; H, 5.77; N, 13.02.

EXAMPLE 75

3(RS)-Phenylaminocarbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=$\phi$, $R^4$=H, A=NHCO, n=1)

a. 2(RS),3(SR)-Phenylaminocarbonyl-L-valyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_3$)$_2$CH—, $R^3$=$\phi$, $R^4$=H, A=NHCO, n=1)

Using the method of Example 15a, material prepared by the procedure of Example 3d was allowed to react with phenylisocyanate to provide the title compound, isolated in 62% yield after purification by flash chromatography (MeOH:CHCl$_3$ (2:98)); TLC, R$_f$=0.24 & 0.32, MeOH:CHCl$_3$ (2:98).

b.

3(RS)-Phenylaminocarbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=φ, $R^4$=H, A=NHCO, n=1)

Using the method of Example 31c, the product of Example 75a was oxidized to afford, after purification by flash chromatography (MeOH:CHCl$_3$ (2:98)), the title product (75%); HPLC, $t_R$=5.70 & 8.77, Col A, H$_2$O:CH$_3$CN (60:40), FR=2.0.

Analysis calculated for: C$_{23}$H$_{31}$F$_3$N$_4$O$_4$·0.75H$_2$O: C, 55.47; H, 6.58; N, 11.25. Found: C, 55.46; H, 6.50; N, 10.72.

EXAMPLE 76

3(RS)-(4-Ethoxycarbonylphenyl)aminocarbonyl-L-phenylalanyl-N-[3-(1,1,1-trifluoro-4-methyl-2-oxopentyl)]-L-prolinamide (Formula Ib, $R^1$=CH(CH$_3$)CH$_3$, $R^2$=φCH$_2$—, $R^3$=4-[CH$_3$CH$_2$OC(O)]φ, $R^4$=H, A=NHCO, n=1)

a.

2(RS),3(SR)-1-Phenylmethoxycarbonyl-N-[3-(1,1,1-trifluoro-2-hydroxy-4-methylpentyl)]-L-prolinamide (Formula VIIa, $R^1$=CH(CH$_3$)CH$_3$, $R^3$=φCH$_2$—, A=OCO, n=1)

Using the method of Example 2a, material prepared according to the method of Example 4 was allowed to react with CBZ-L-proline to provide the title compound (100%); TLC, $R_f$=0.37 & 0.45, MeOH: CH$_2$Cl$_2$ (5:95).

b.

2(RS),3(SR)-N-[3-(1,1,1-trifluoro-2-hydroxy-4-methylpentyl)]-L-prolinamide (Formula IVa, $R^1$=CH(CH$_3$)CH$_3$, n=1)

Using the method of Example 2b, the product of Example 76a was converted into the title product (100%); TLC, $R_f$=0.73 & 0.81, MeOH:CH$_2$Cl$_2$ satd with NH$_4$OH (15:85).

c.

2(RS),3(SR)-Phenylmethoxycarbonyl-L-phenylalanyl-N-[3-(1,1,1-trifluoro-2-hydroxy-4-methylpentyl)]-L-prolinamide (Formula VIIb, $R^1$=CH(CH$_3$)CH$_3$, $R^2$=CH$_2$φ, $R^3$=φCH$_2$—, $R^4$=H, A=OCO, n=1)

After DCC (2.27 g, 11.0 mmol) was added to a stirred solution of CBZ-L-phenylalanine (2.29 g, 10.0 mmol), HOBT (2.70 g, 17.6 mmol) and material prepared according to Example 76b (2.68 g, 10.0 mmol) in dry THF (45 ml) chilled to −17° C., the mixture was left at room temperature overnight, filtered, and concentrated to remove the THF before it was taken up in Et$_2$O and EtOAc. The resulting solution was washed (satd NaHCO$_3$ (2×), 1N HCl, brine), dried (MgSO$_4$), filtered, concentrated, and taken up in minimal CH$_2$Cl$_2$. After N,N'-dicyclohexylurea was filtered, the solution was concentrated under vacuum, and dried under vacuum to provide the title compound in quantitative yield as a white foam; TLC, $R_f$=0.37 & 0.45, MeOH:CH$_2$Cl$_2$ (5:95).

d.

2(RS),3(SR)-L-Phenylalanyl-N-[3-(1,1,1-trifluoro-2-hydroxy-4-methylpentyl)]-L-prolinamide (Formula IVb, $R^1$=CH(CH$_3$)CH$_3$, $R^2$=CH$_2$φ, $R^4$=H, n=1)

A mixture of the product of Example 76c (501.3 mg, 0.898 mmol) and 50%-water wet 10% Pd/C (50 mg) in absolute EtOH (17 ml) was stirred under hydrogen (1 atmosphere, 101,325 Pascals) overnight, filtered, concentrated and dried under vacuum to provide the title compound in quantitative yield; TLC, $R_f$=0.14, MeOH: CH$_2$Cl$_2$ (5:95); $R_f$=0.43 & 0.48 MeOH: NH$_4$OH satd CH$_2$Cl$_2$ (5:95).

e.

2(RS),3(SR)-(4-Ethoxycarbonylphenyl)aminocarbonyl-L-phenylalanyl-N-[3-(1,1,1-trifluoro-2-hydroxy-4-methylpentyl)]-L-prolinamide (Formula VIIb, $R^1$=CH(CH$_3$)CH$_3$, $R^2$=φCH$_2$—, $R^3$=4-[CH$_3$CH$_2$OC(O)]φ—, $R^4$=H, A=NHCO, n=1)

Using the method of Example 15a material prepared by the procedure of Example 76d was allowed to react with ethyl 4-isocyanatobenzoate to provide the title compound, isolated in 95% yield; TLC; $R_f$=0.21 & 0.26, MeOH:CH$_2$Cl$_2$ (5:95).

f.

3(RS)-(4-Ethoxycarbonylphenyl)aminocarbonyl-L-phenylalanyl-N-[3-(1,1,1-trifluoro-4-methyl-2-oxopentyl)]-L-prolinamide (Formula Ib, $R^1$=CH(CH$_3$)CH$_3$, $R^2$=(CH$_2$—, $R^3$=4-[CH$_3$CH$_2$OC(O)]φ—, $R^4$=H, A=NHCO, n=1)

Using the method of Example 61c, the product of Example 76e was oxidized to afford, after purification by flash chromatography (gradient elution, Et$_2$O: pentane (11:1) to Et$_2$O), the title product (94%); HPLC, $t_R$=10.26 & 13.52, Col A, CH$_3$CN:H$_2$O (45:55), FR=2.0.

Analysis calculated for: C$_{30}$H$_{35}$F$_3$N$_4$O$_6$·1.24H$_2$O: C, 57.47; H, 6.03; N, 8.94. Found: C, 57.43; H, 6.02; N, 8.97.

EXAMPLE 77

3(RS)-[[4-[(1-Naphthylsulfonyl)aminocarbonyl]phenyl]aminocarbonyl]-L-valyl-N-[3-(1,1,1-trifluoro-4-methyl-2-oxopentyl)]-L-prolinamide (Formula Ib, $R^1$=CH(CH$_3$) CH$_3$, $R^2$=(CH$_3$)$_2$CH—, $R^3$=4-[1-naphthyl-S(O$_2$)NHC(O)]φ, $R^4$=H, A=NHCO, n=1)

a. 1-Naphthalene sulfonamide

Ammonia was passed (for 5 min) into a stirred solution of 1-naphthalenesulfonyl chloride (5.0 g, 22 mmol) and anhydrous Et$_2$O (400 ml) at −78°. The resulting mixture was stirred at −78° for 1 hr, allowed to warm to room temperature, and stirred overnight. The Et$_2$O was removed under vacuum to leave a white powder which was washed with water and dried under vacuum to give 3.2 g (70%) of the title compound as a white powder, m.p. 152°–153° C.

b.

3(RS)-[[4-[(1-Naphthylsulfonyl)aminocarbonyl]phenyl]aminocarbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[1-naphthyl-S(O$_2$)NHC(O)]φ, $R^4$=H, A=NHCO, n=1)

1-Naphthalene sulfonamide, prepared according to Example 77a (0.64 g, 3.09 mmol), was added to a stirred solution of material prepared according to Example 16 (1.5 g, 2.84 mmol), DMAP (0.38 g, 3.1 mmol), WSCDI (0.59 g, 3.08 mmol) and dry CH$_2$Cl$_2$ (40 ml) under nitrogen at room temperature. The resulting reaction mixture was stirred at room temperature overnight before it was washed (1N HCl), dried (MgSO$_4$), and filtered. The filtrate was concentrated under vacuum to a gummy residue which was purified by flash chromatography, (CH$_2$Cl$_2$ then CH$_2$Cl$_2$:MeOH:AcOH (98:1.9: 0.1) to give 0.76 g (36%) of the title compound as a white powder; HPLC, t$_R$=10.08 & 16.38, Col A, CH$_3$CN:H$_2$O (30:70), FR=2.5.

Analysis calculated for: C$_{34}$H$_{38}$F$_3$N$_5$O$_7$S.0H$_2$O: C, 54.25; H, 5.49; N, 9.30. Found: C, 54.56; H, 5.68; N, 8.85.

EXAMPLE 78

3(RS)-N$^2$-(4-Hydroxycarbonylphenyl)aminocarbonyl-N$^6$-phenylmethoxycarbonyl-L-lysyl-N-[3-(1,1,1-trifluoro-4-methyl-2-oxopentyl)]-L-prolinamide (Formula Ib, R$^1$=CH(CH$_3$)CH$_3$, R$^2$=(CH$_2$)$_4$NHC(O)OCH$_2\phi$, R$^3$=4-[HOC(O)]$\phi$, R$^4$=H, A=NHCO, n=1)

a.

2(RS),3(SR)-N$^2$-(4-Ethoxycarbonylphenyl)aminocarbonyl-N$^6$-phenylmethoxycarbonyl-L-lysyl-N-[3-(1,1,1-trifluoro-2-hydroxy-4-methylpentyl)]-L-prolinamide (Formula VIIb, R$^1$=CH(CH$_3$)CH$_3$, R$^2$=(CH$_2$)$_4$NHC(O)OCH$_2$O, R$^3$=4-[EtOC(O)]$\phi$, R$^4$=H, A=NHCO, n=1)

Using the method of Example 15a, material prepared by the procedure of Example 72a was allowed to react with ethyl 4-isocyanatobenzoate to provide the title compound, isolated in 95% yield after purification by flash chromatography (gradient elution, CHCl$_3$ to MeOH:CHCl$_3$ (2:98), then (5:95)); TLC, R$_f$=0.41, MeOH:CHCl$_3$ (2.5:97.5).

b.

3(RS)-N$^2$-(4-Ethoxycarbonylphenyl)aminocarbonyl-N$^6$-phenylmethoxycarbonyl-L-lysyl-N-[3-(1,1,1-trifluoro-4-methyl-2-oxopentyl)]-L-prolinamide (Formula Ib, R$^1$=CH(CH$_3$)CH$_3$, R$^2$=(CH$_2$)$_4$NHC(O)OCH$_2\phi$, R$^3$=4-[EtOC(O)]$\phi$, R$^4$=H, A=NHCO, n=1)

Using the method of Example 31c, the product of Example 78a was oxidized to afford, after purification by flash chromatography (gradient elution, CHCl$_3$ to MeOH:CHCl$_3$ (2.5:97.5) to (5:95)), the title product (77%); TLC, R$_f$=0.48, MeOH:CHCl$_3$ (2.5:97.5).

c.

3(RS)-N$^2$-(4-Hydroxycarbonylphenyl)aminocarbonyl-N$^6$-phenylmethoxycarbonyl-L-lysyl-N-[3-(1,1,1-trifluoro-4-methyl-2-oxopentyl)]-L-prolinamide (Formula Ib, R$^1$=CH(CH$_3$)CH$_3$, R$^2$=(CH$_2$)$_4$NHC(O)OCH$_2\phi$, R$^3$=4-[HOC(O)]$\phi$, R$^4$=H, A=NHCO, n=1)

Using the method of Example 14, material prepared according to the procedure of Example 78b was converted into the title product and isolated in 85% yield; HPLC, t$_R$=4.71 & 6.76, Col A, CH$_3$CN:H$_2$O (40:60), FR=2.5.

Analysis calculated for: C$_{33}$H$_{40}$F$_3$N$_5$O$_8$.1.5H$_2$O: C, 55.15; H, 6.03; N, 9.74. Found: C, 54.90; H, 5.92; N, 9.29.

EXAMPLE 79

3(RS)-(4-Hydroxycarbonylphenyl)carbonyl-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[HOC(O)]$\phi$, R$^4$=H, A=CO n=1)

Using the method of Example 14, material prepared according to the procedure of Example 84c was converted into the title product and isolated in 72% yield; HPLC, t$_R$=3.48 & 5.31, Col A, H$_2$O:CH$_3$CN (3:1), FR=2.0.

Analysis calculated for: C$_{24}$H$_{30}$F$_3$N$_3$O$_6$.1.0H$_2$O: C, 54.23; H, 6.07; N, 7.91. Found: C, 54.46; H, 6.05; N, 7.69.

EXAMPLE 80

3(RS)-Phenylsulphonyl-L-$\alpha$-aminobutyryl-N-[3-(1,1,1-trifluoro-4-methyl-2-oxopentyl)]-L-prolinamide (Formula Ib, R$^1$=CH(CH$_3$)CH$_3$, R$^2$=CH$_3$CH$_2$—, R$^3$=$\phi$, R$^4$=H, A=S(O$_2$), n=1)

a.

2(RS),3(SR)-Phenylsulfonyl-L-$\alpha$-aminobutyryl-N-[3-(1,1,1-trifluoro-2-hydroxy-4-methylpentyl)]-L-prolinamide (Formula VIIb, R$^1$=CH(CH$_3$)CH$_3$, R$^2$=CH$_3$CH$_2$—, R$^3$=$\phi$, R$^4$=H, A=S(O$_2$), n=1)

NMM (0.24 g, 2.4 mmol) and benzenesulfonyl chloride (0.21 g, 1.2 mmol) were added to a solution of material prepared according to Example 61a (0.5 g, 1.1 mmol) in CH$_2$Cl$_2$ (5 ml), and the reaction was stirred overnight at room temperature. The reaction was concentrated under vacuum; the residue was taken up in EtOAc and filtered; and the filtrate concentrated under vacuum to give the crude product. The product was partially purified by flash chromatography (gradient, MeOH:CHCl$_3$ (2.5:97.5) to (5:95)) and finally purified by flash chromatography (gradient, Et$_2$O:hexane (80:20) to Et$_2$O:hexane (90:10) to Et$_2$O) to give the title product (0.118 g); TLC, R$_f$=0.33, Et$_2$O.

b.

3(RS)-Phenylsulfonyl-L-$\alpha$-aminobutyryl-N-[3-(1,1,1-trifluoro-4-methyl-2-oxopentyl)]-L-prolinamide (Formula Ib, R$^1$=CH(CH$_3$)CH$_3$, R$^2$=CH$_3$CH$_2$—, R$^3$=$\phi$, R$^4$=H, A=S(O$_2$), n=1)

Using the method of Example 31c, the product of Example 80a was oxidized to afford, after purification by flash chromatography (gradient, MeOH:CHCl$_3$ (0:100) to (2:98) to (5:95)), the title product (42%); HPLC, t$_R$=4.97 & 6.17, Col A, H$_2$O:CH$_3$CN (1:1), FR=1.0.

Analysis calculated for: C$_{21}$H$_{28}$F$_3$N$_3$O$_5$S.H$_2$O: C, 49.50; H, 5.93; N, 8.25. Found: C, 49.70; H, 6.24; N, 7.67.

EXAMPLE 81

3(RS)-[1-(Ethoxycarbonyl)cyclopent-1-yl]carbonyl-L-$\alpha$-aminobutyryl-N-[3-(1,1,1-trifluoro-4-methyl-2-oxopentyl)]-L-prolinamide (Formula Ib, R$^1$=CH(CH$_3$)CH$_3$, R$^2$=CH$_3$CH$_2$—, R$^3$=1-[CH$_3$CH$_2$OC(O)]cyclopent-1-yl-, R$^4$=H, A=CO, n=1)

a. 1-(Ethoxycarbonyl)cyclopentanecarboxylic acid

To a solution of diethyl 1,1-cyclopentane dicarboxylate (2.5 g, 11.68 mol) in EtOH (10 ml) was added dropwise a solution of KOH (654 mg, 11.68 mmol) in EtOH (10 ml) over ½ hour. The resulting mixture was stirred at room temperature for 96 hr, concentrated under vacuum, and partitioned between H$_2$O and EtOAc. The aqueous layer was acidified with concentrated HCl and extracted with EtOAc. The EtOAc extracts were washed (brine), dried (Na$_2$SO$_4$), filtered, and concentrated under vacuum to give the product (1.73 g) as a clear oil.

b.
2(RS),3(SR)-[1-Ethoxycarbonyl)cyclopent-1-yl)]carbonyl-L-α-aminobutyryl-N-[3-(1,1,1-trifluoro-2-hydroxy-4-methylpentyl)]-L-prolinamide (Formula VIIb, $R^1$=CH(CH$_3$)CH$_3$, $R^2$=CH$_3$CH$_2$—, $R^3$=1-[CH$_3$CH$_2$OC(O)]cyclopent-1-yl, $R^4$=H, A=CO, n=1)

Using the method of Example 50a with the following ratios of reagents to one equivalent of the product prepared according to Example 81a: HOBT (3.3 equivalents), DCC (1.65 equivalents), TEA (1.5 equivalents) and material prepared according to the procedure of Example 61a (1.0 equivalent), and omitting the citric acid wash, the title product was prepared, isolated by suction chromatography (gradient elution, Et$_2$O:hexane (1:1) to Et$_2$O) in 46% yield; TLC, $R_f$=0.47, MeOH:CHCl$_3$ (5:95).

Analysis calculated for: $C_{24}H_{38}F_3N_3O_6$: C, 55.27; H, 7.34; N, 8.06. Found: C, 54.74; H, 5.93; N, 7.88.

c.
3(RS)-[1-(Ethoxycarbonyl)cyclopent-1-yl)]carbonyl-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$, $R^3$=1-[CH$_3$CH$_2$OC(O)]-cyclopent-1-yl, $R^4$=H, A=CO, n=1)

Using the method of Example 33c, the product of Example 81b was oxidized to afford, after purification by flash chromatography (acetone:hexane (1:4)), the title product (37%); HPLC, $t_R$=6.68 & 8.31, Col A, H$_2$O:CH$_3$CN (70:30), FR=2.0.

Analysis calculated for: $C_{24}H_{36}F_3N_3O_6 \cdot 1.1H_2O$: C, 53.44; H, 7.13; N, 7.80. Found: C, 53.48; H, 6.97; N, 7.60.

EXAMPLE 82

3(RS)-(Tricyclo[3.3.1.1$^{3,7}$]dec-1-yl)sulfonyl-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$—, $R^3$=1-adamantyl, $R^4$=H, A=S(O$_2$), n=1)

a. 1-Adamantane sulfinyl chloride

Aluminum trichloride (40 g, 3 mol) was added slowly to thionyl chloride (200 ml, 2.7 mol), and the mixture was cooled to −20°. Adamantane was added in portions over 2½ hrs, and the resulting mixture was stirred 1 hr and allowed to warm to room temperature. After the thionyl chloride was removed under vacuum, the residue was diluted with CCl$_4$; and the aluminum trichloride was decomposed with ice and water. The layers were separated; and the organic layer was washed (brine), dried (Na$_2$SO$_4$), filtered, and concentrated under vacuum. The residue was distilled under vacuum (1 torr, 133.3 Pascals) with a vigreaux column to give the product (28.8 g; bp 118°–128°) as a waxy solid; TLC, $R_f$=0.6–0.4, EtOAc:hexanes (15:85).

b.
2(RS),3(SR)-(Tricyclo[3.3.1.1$^{3,7}$]dec-1-yl)sulfonyl-L-α-aminobutyryl-N-[3-(1,1,1-trifluoro-2-hydroxy-4-methylpentyl)]-L-prolinamide (Formula VIIb, $R^1$=CH(CH$_3$)CH$_3$, $R^2$=CH$_3$CH$_2$—, $R^3$=1-adamantyl, $R^4$=H, A=S(O), n=1

Using the method of Example 20a, material prepared according to the procedure of Example 61a was allowed to react with material prepared according to Example 82a to provide the title compound, isolated in 61% yield after purification by suction flash chromatography (gradient, Et$_2$O:EtOAc (1:1) to EtOAc); TLC, $R_f$=0.53, MeOH:CHCl$_3$ (5:95).

Analysis calculated for: $C_{25}H_{40}F_3N_3O_4S \cdot 0.45H_2O$: C, 55.22; H, 7.58. Found: C, 55.05; H, 7.57.

c.
2(RS),3(SR)-(Tricyclo[3.3.1.1$^{3,7}$]dec-1-yl)sulfonyl-L-α-aminobutyryl-N-[3-(1,1,1-trifluoro-2-hydroxy-4-methylpentyl)]-L-prolinamide (Formula VIIb $R^1$=CH(CH$_3$)CH$_3$, $R^2$=CH$_3$CH$_2$—, $R^3$=1-adamantyl, $R^4$=H, A=S(O$_2$), n=1)

To a solution of the product of Example 82b (277 mg, 0.515 mmol) in acetone (25 ml) at reflux was added a satd acetone solution of KMnO$_4$ (60 ml) dropwise over 1 hr. This was stirred 15 min at reflux, cooled, filtered through Celite®, and concentrated under vacuum. The crude product was purified by flash chromatography (EtOAc:Et$_2$O (4:6)) to give the title product (180 mg) as a solid; TLC, $R_f$=0.67 & 0.70, MeOH:CHCl$_3$ (1:9).

Analysis calculated for: $C_{25}H_{40}F_3N_3O_5S$: C, 54.43; N, 7.31; N, 7.62. Found: C, 54.49; N, 7.33; N, 7.39.

d.
3(RS)-(Tricyclo[3.3.1.1$^{3,7}$]dec-1-yl)sulfonyl-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$—, $R^3$=1-adamantyl, $R^4$=H, A=S(P$_2$), n=1)

Using the method of Example 33c, the product of Example 82c was oxidized to afford, after purification by flash chromatography (acetone:hexanes (15: 85)), the title product (40%); HPLC, $t_R$=6.27 & 8.29, Col A, H$_2$O:CH$_3$CN (1:1), FR=2.0.

Analysis calculated for: $C_{25}H_{38}F_3N_3O_5S \cdot 0.5H_2O$: C, 53.75; H, 7.04; N, 7.32. Found: C, 53.91; H, 7.11; N, 6.97.

EXAMPLE 83

3(RS)-[1-(Hydroxycarbonyl)cyclopent-1-yl]carbonyl-L-α-aminobutyryl-N-[3-(1,1,1-trifluoro-4-methyl-2-oxopentyl)]-L-prolinamide (Formula Ib, $R^1$=CH(CH$_3$)CH$_3$, $R^2$=CH$_3$CH$_2$—, $R^3$=1-[HOC(O)]cyclopent-1-yl, $R^4$=H, A=CO, n=1)

Using the method of Example 14, material prepared according to the procedure of Example 81c was converted into the title product and isolated in 79% yield; HPLC, $t_R$=3.74 & 4.92, Col A, H$_2$O:CH$_3$CN (3:1), FR=2.0.

Analysis calculated for: $C_{22}H_{32}F_3N_3O_6 \cdot 0.35H_2O$: C, 53.08; H, 6.62; N, 8.44. Found: C, 53.04; H, 6.58; N, 8.16.

EXAMPLE 84

3(RS)-(4-Methoxycarbonylphenyl)carbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[CH$_3$OC(O)]φ $R^4$=H, A=CO, n=1)

a. 4-Methoxycarbonylbenzenecarboxylic acid

Concentrated sulfuric acid (277.5 ml, 5.2 mol) was added dropwise over ½ hr to a stirred solution of chromium (VI) oxide (299.25 g, 2.99 mol) and water (925 ml) at 0°. The resulting solution was added dropwise over 1 hr to a stirred solution of methyl-4-(hydroxymethyl)-benzoate (92.5 g, 0.564 mol) and acetone (4.6 l) at 0°. The reaction mixture was allowed to warm to room temperature and stirred overnight. The supernatant was decanted before the black tar-like residue was extracted with acetone. The decanted supernatant and acetone extracts were combined and concentrated under vacuum to leave a dark brown residue which was triturated with cold water (4 liter). The precipitate which formed was collected, washed three times with water (1 liter), and dried to give 94.6 g (94%) of the title compound as white crystals, m.p. 218°–221° C.

b.
2(RS),3(SR)-(4-Methoxycarbonylphenyl)carbonyl-L-valyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_3$)$_2$CH—, $R^3$=4-[CH$_3$OC(O)]$\phi$, $R^4$=H A=CO, n=1)

WSCDI (10.27 g, 53.6 mmol) was added to a stirred solution of a compound prepared according to Example 3d (17.54 g, 47.8 mmol), the product of Example 84a (8.6 g, 47.8 mmol), HOBT (12.86 g, 95.3 mmol) and dry THF (400 ml) at 0° under nitrogen. The resulting reaction mixture was stirred at 0° for 1 hr; then it was allowed to come to room temperature and to stir overnight. The THF was removed under vacuum to leave an oily residue which was dissolved in EtOAc. The EtOAc solution was washed (1N HCl, satd aq, NaHCO$_3$, and brine), dried (MgSO$_4$), filtered, and concentrated under vacuum to give 24.45 g of the crude product as a dry white foam. Purification by flash chromatography (CHCl$_3$:MeOH (97:3)) produced the title compound (79%); HPLC, $t_R$=4.62 & 5.80, Col A, H$_2$O:CH$_3$CN (55:45); FR=3.0.

c.
3(RS)-(4-Methoxycarbonylphenyl)carbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[CH$_3$OC(O)]$\phi$, $R^4$=H, A=CO, n=1)

Using the method of Example 31c, the product of Example 84b was oxidized to afford, after purification by flash chromatography (CHCl$_3$:MeOH (98:2)), the title product (69%); HPLC, $t_R$=4.51 & 6.82, Col A, H$_2$O: CH$_3$CN (55:45), FR=2.0.

Analysis calculated for: C$_{25}$H$_{32}$F$_3$N$_3$O$_6$.0.5H$_2$O: C, 55.96; H, 6.19; N, 7.83. Found: C, 55.90; H, 6.30; N, 7.93.

d.
3(RS)-(4-Methoxycarbonylphenyl)carbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)CH$_3$, $R^3$=4-(CH$_3$OCO)$\phi$, $R^4$=H, A=CO, n=1)

A preferred method employing the oxidation described in D. B. Dess and J. C. Martin, *J. Org. Chem.*, 48, 4155–4156(1983) for the preparation of the title compound is as follows: To a stirred solution of Dess-Martin periodinane (6.76 g, 15.96 mmol) and a product prepared using the method of Example 84b (6.49 g, 12.25 mmol) in dry CH$_2$Cl$_2$ (80 ml) under nitrogen was added TFA (1.82 g, 1.23 ml, 15.96 mmol). After the reaction mixture had been stirred overnight at room temperature, Et$_2$O (about 3 to 5 times the volume of CH$_2$Cl$_2$) was added, and the mixture was poured into an aq solution of satd NaHCO$_3$ and Na$_2$S$_2$O$_3$ (17.63 g, 111.51 mmol). After 15 min of stirring, the organic layer was separated, washed (satd NaHCO$_3$, brine), dried (Na$_2$SO$_4$), filtered, and concentrated to give the title product as a white foam (6.42 g, 99.4%); TLC, $R_f$=0.67 & 0.76; MeOH: CHCl$_3$ (3:97); HPLC, $t_R$=4.64 & 6.84, Col A, H$_2$O:CH$_3$CN (60:40), FR=2.0.

EXAMPLE 85

3(RS)-(4-Hydroxycarbonylphenyl)aminocarbonyl-L-phenylalanyl-N-[3-(1,1,1-trifluoro-4-methyl-2-oxopentyl)]-L-prolinamide (Formula Ib, $R^1$=CH(CH$_3$)CH$_3$, $R^2$=$\phi$CH$_2$, $R^3$=4-[HOC(O)]$\phi$, $R^4$=H, A=NHCO, n=1)

Using the method of Example 14, material prepared according to the procedure of Example 76f was converted into the title product and isolated by flash chromatography (gradient, MeOH:CH$_2$Cl$_2$ (4:96) to (10:90)) in 48% yield; HPLC, $t_R$=5.52 & 8.12, Col A, CH$_3$CN:H$_2$O (35:65), FR=2.0.

Analysis calculated for: C$_{28}$H$_{31}$F$_3$N$_4$O$_6$.H$_2$O: C, 56.56; H, 5.59; N, 9.42. Found: C, 56.58; H, 5.59; N, 9.22.

EXAMPLE 86

3(RS)-(4-Methoxycarbonylphenyl)methoxycarbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[CH$_3$OC(O)]$\phi$CH$_2$—, $R^4$=H, A=OCO, n=1)

a. (4-Methoxycarbonylphenyl)methyl 4-nitrophenyl carbonate

Using the method of Example 7a, but omitting the pH 7.0 wash, methyl 4-hydroxymethylbenzoate was converted into the title compound which was isolated by trituration with hexanes, washed with hexanes:EtOAc (1:1), and dried under vacuum to provide a 50% yield; TLC, $R_f$=0.75, EtOAc:hexane (1:1).

b.
2(RS),3(SR)-(4-Methoxycarbonylphenyl)methoxycarbonyl-L-valyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_3$)$_2$CH, $R^3$=4-[CH$_3$OC(O)]$\phi$CH$_2$, $R^4$=H, A=OCO, n=1)

Using the method of Example 7b, material prepared by the procedure of Example 3d was allowed to react with the product of Example 86a to provide the title compound, which was isolated in 48% yield after purification by flash chromatography (acetone: hexanes (2:3)), TLC, $R_f$=0.63 & 0.68, MeOH:CHCl$_3$ (1:9).

Analysis calculated for: C$_{26}$H$_{36}$F$_3$N$_3$O$_7$: C, 55.81; H, 6.48; N, 7.51. Found: C, 55.54; H, 6.39; N, 7.29.

c.
3(RS)-(4-Methoxycarbonylphenyl)methoxycarbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[CH$_3$OC(O)]$\phi$CH$_2$, $R^4$=H, A=OCO, n=1)

Using the method of Example 33c, the product of Example 86b was oxidized to afford, after purification by preparative TLC (EtOAc:Et$_2$O (3:2)), the title product (10%); HPLC, $t_R$=4.32 & 6.44, H$_2$O:CH$_3$CH (1:1), FR=2.0.

Analysis calculated for: C$_{26}$H$_{34}$F$_3$N$_3$O$_7$.0.65H$_2$O: C, 54.86; H, 6.25; N, 7.38. Found: C, 54.87; H, 6.25; N, 7.05.

EXAMPLE 87

3(RS)-[E-3-(4-Ethoxy
carbonylphenyl)-1-oxoprop-2-enyl]-L-valyl-N-[3-
(1,1,1-trifluoro-4-methyl-2-oxopentyl)]-L-prolinamide
(Formula Ib, $R^1$=CH($CH_3$)$CH_3$, $R^2$=($CH_3$)$_2$CH—,
$R^3$=E-4-[$CH_3CH_2$O—C(O)]$\phi$CH=CH, $R^4$=H,
A=CO, n=1)

a. Ethyl 4-formylbenzoate

A mixture of 4-formylbenzoic acid (25 g) conc sulfuric acid (2 ml) and EtOH (19.5 ml) was refluxed gently for 5 days in 100 ml of 1,2-dichloroethane. The solvent was then stripped, and $Et_2O$ was added to the residue. The $Et_2O$ solution was washed (satd aq $NaHCO_3$) dried ($Na_2SO_4$), filtered, and evaporated. Bulb to bulb distillation afforded 20.1 g (68%) of the title ester as a clear liquid, bp 145°–150° (2,900 Pascals, 22 torr).

b. E-(4-Ethoxycarbonyl)benzenepropenoic acid

A mixture of the product of Example 87a (8.9 g), malonic acid (10.4 g), and piperidine (1 ml) in 25 ml of pyridine was heated on a steam bath for 3 hr. After the solvent was evaporated and the residue slurried in 200 ml of water, the pH was adjusted to 6 with acetic acid. The precipitate was collected and air dried. Crystallization of the material from EtOH gave 10.1 g (92%) of the title acid as sparkling white crystals, mp 220.5°–221°.

c.

2(RS),3(SR)-[E-3-(4-Ethoxycarbonylphenyl)-1-oxo-
prop-2-enyl]-L-valyl-N-[3-(1,1,1-trifluoro-2-hydroxy-4-
methylpentyl)]-L-prolinamide (Formula VIIb,
$R^1$=CH($CH_3$)$CH_3$, $R^2$=($CH_3$)$_2$CH—,
$R^3$=E-[4-$CH_3CH_2$O—C(O)]$\phi$CH=CH, $R^4$=H,
A=CO, n=1)

Using the method of Example 32a, material prepared by the procedure of Example 3d was allowed to react with the product of Example 87b to provide the title compound, isolated in 88% yield; TLC, $R_f$=0.14 & 0.18, MeOH:$CH_2Cl_2$ (5:95).

d.

3(RS)-[E-3-(4-Ethoxycarbonylphenyl)-1-oxoprop-2-
enyl]-L-valyl-N-[3-(1,1,1-trifluoro-4-methyl-2-oxopen-
tyl)]-L-prolinamide (Formula Ib, $R^1$=CH($CH_3$)$CH_3$,
$R^2$=($CH_3$)$_2$CH—,
$R^3$=E-[4-$CH_3CH_2$OC(O)]$\phi$—HC=CH, $R^4$=H,
A=CO, n=1)

Using the method of Example 61c, the product of Example 87c was oxidized to afford, after purification by flash chromatography (MeOH: $CH_2Cl_2$ (2:98)), the title product (65%); TLC, $R_f$=0.23, MeOH:$CH_2Cl_2$ (5:95).

Analysis calculated for: $C_{28}H_{36}F_3N_3O_6$: C, 59.25; H, 6.39; N, 7.40. Found: C, 59.14; H, 6.75; N, 7.21.

EXAMPLE 88

3(RS)-(2-Ethoxycarbonylphenyl)aminocarbonyl-L-
valyl-N-[3-(1,1,1-trifluoro-4-methyl-2-oxopentyl)]-L-
prolinamide (Formula Ib, $R^1$=CH($CH_3$)$CH_3$,
$R^2$=($CH_3$)$_2$CH—, $R^3$=2-[CHBCH$_2$OC(O)]$\phi$, $R^4$=H,
A=NHCO, n=1)

a.

2(RS),3(SR)-(2-Ethoxycarbonylphenyl)aminocarbonyl-
L-valyl-N-[3-(1,1,1-trifluoro-2-hydroxy-4-methylpen-
tyl)]-L-prolinamide (Formula VIIb,
$R^1$=CH($CH_3$)$CH_3$, $R^2$=($CH_3$)$_2$CH—,
$R^3$=2-[$CH_3CH_2$OC(O)]$\phi$, $R^4$=H, A=NHCO, n=1)

Using the method of Example 15a, material prepared by the procedure of Example 3d was allowed to react with ethyl 2-isocyanatobenzoate to provide the title compound, which was isolated in 66% yield after purification by flash chromatography (EtOAc: hexane (60:40)); TLC, $R_f$=0.48 & 0.57, MeOH:CHCl$_3$ (5:95).

b.

3(RS)-(2-Ethoxycarbonylphenyl)aminocarbonyl-L-
valyl-N-[3-(1,1,1-trifluoro-4-methyl-2-oxo-pentyl)]-L-
prolinamide (Formula Ib, $R^1$=CH($CH_3$)$CH_3$,
$R^2$=CH($CH_3$)$CH_3$, $R^3$=2-($CH_3CH_2$OCO)$\phi$, $R^4$=H,
A=NHCO, n=1)

A modification of the procedure of Example 54b was done using the indicated ratios of the product of Example 88a (1 equivalent), oxalyl chloride (2 equivalents), DMSO (4 equivalents) with the reaction mixture cooled to $-45°$ for these above-listed additions and warmed to $-20°$ for addition of the TEA (instead of diisopropylethylamine). The work up included washing (1N HCl, satd aq $NaHCO_3$, 10% aq NaOCl, brine). The title product was obtained after purification by flash chromatography ($Et_2O$:hexane (4:1)) in 74% yield; HPLC, $t_R$=6.95 & 10.46, Col A, $CH_3CN$ :$H_2O$ (35:65), FR=2.0.

Analysis calculated for: $C_{26}H_{35}F_3N_4O_6 \cdot 0.75$ $H_2O$: C, 54.78; H, 6.45; N, 9.83. Found: C, 54.73; H, 6.34; N, 9.51.

EXAMPLE 89

3(RS)-4-[(4-Nitrophenyl)sulfonylaminocarbonyl]-
phenylcarbonyl-L-valyl-N-[3-(1,1,1-trifluoro-4-methyl-
2-oxopentyl)]-L-prolinamide (Formula Ib,
$R^1$=CH($CH_3$)$CH_3$, $R^2$=($CH_3$)$_2$CH—,
$R^3$=4-[(4-NO$_2\phi$)S(O$_2$)NHCO]$\phi$, $R^4$=H, A=CO,
n=1)

4-Nitrobenzene sulfonamide (0.196 g, 0.97 mmol) was added to a stirred solution of the product of Example 79 (0.5 g, 0.97 mmol), DMAP (0.12 g, 0.97 mmol), DCC (0.22 g, 0.97 mmol), and dry $CH_2Cl_2$ (30 ml) under nitrogen at room temperature. The resulting mixture was stirred overnight at room temperature and filtered. The filtrate was washed (1N HCl), dried (MgSO$_4$), filtered, and concentrated under vacuum to a yellow residue which was purified by flash chromatography, (CHCl$_3$ :MeOH:AcOH (90:9.8:0.2)) to give 0.29 g (43%) of the title compound as a white powder; HPLC, $t_R$=4.26 & 8.42, Col A, $H_2O$:$CH_3CN$ (4:1), FR=2.0.

Analysis calculated for: $C_{30}H_{34}F_3N_5O_9 \cdot H_2O$: C, 50.34; H, 5.06; N, 9.78. Found: C, 50.03; H, 4.92; N, 9.43.

EXAMPLE 90

3(RS)-Phenylmethoxycarbonyl-L-glutamyl-N-[3-(1,1,1-trifluoro-4-methyl-2-oxopentyl)]-L-prolinamide phenylmethyl ester (Formula Ib, $R^1$=CH(CH$_3$)CH$_3$, $R^2$=—(CH$_2$)$_2$C(O)OCH$_2\phi$, $R^3$=$\phi$CH$_2$—, $R^4$=H, A=OCO, n=1)

a.

2(RS),3(SR)-Phenylmethoxycarbonyl-L-glutamyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_2$)$_2$C(O)OCH$_2\phi$, $R^3$=$\phi$CH$_2$—, $R^4$=H, A=OCO, n=1).

Using the method of Example 84b, CBZ-glutamic acid gamma-benzylester was allowed to react with material prepared according to the method of Example b to provide the title compound, isolated in 64% yield after purification by flash chromatography (gradient elution, hexane:Et$_2$O (1:3) to Et$_2$O); TLC, $R_f$=0.61, Et$_2$O.

b.

3(RS)-Phenylmethoxycarbonyl-L-glutamyl-N-[3-(1,1,1-trifluoro-4-methyl-2-oxopentyl)]-L-prolinamide phenylmethyl ester (Formula Ib, $R^1$=CH(CH$_3$)CH$_3$, $R^2$=(CH$_2$)$_2$C(O)OCH$_2\phi$, $R^3$=$\phi$CH$_2$—, $R^4$=H, A=OCO, n=1)

Using the method of Example 54b, the product of Example 90a was oxidized to afford, after purification by flash chromatography (gradient, hexane:Et$_2$O (2:8) to (1:9)), the title product (30%); HPLC, $t_R$=6.12 & 8.48, Col A, CH$_3$CN:H$_2$O (1:1), FR=3.0.

Analysis calculated for: C$_{31}$H$_{36}$F$_3$N$_3$O$_7$.2H$_2$O: C, 56.78; H, 6.15; N, 6.41. Found: C, 56.98; H, 5.74; N, 6.12.

EXAMPLE 91

3S(or R)-(Tricyclo[3.3.1.1$^{3,7}$]dec-1-yl)sulfonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=1-adamantyl, $R^4$=H, A=S(O$_2$), n=1)

a. 2(RS),3(SR)-(Tricyclo[3.3.1.1$^{3,7}$]dec-1-yl)=sulfinyl-L-valyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_3$)$_2$CH, $R^3$=1-adamantyl, $R^4$=H, A=S(O), n=1)

Using the method of Example 20a, material prepared by the procedure of Example 3d was allowed to react with product from Example 82a to provide the title compound which was isolated by flash chromatography (EtOAc:Et$_2$O (2:3)); TLC, $R_f$=0.75, MeOH:CHCl$_3$ (1:9).

b.

2(RS),3(SR)-(Tricyclo[3.3.1.1$^{3,7}$]dec-1-yl)sulfonyl-L-valyl-N-[3-(1,1,1-trifluoro-2-hydroxy-4-methylpentyl)]-L-prolinamide (Formula VIIb, $R^1$=CH(CH$_3$) CH$_3$, $R^2$=(CH$_3$)$_2$CH—, $R^3$=1-adamantyl, $R^4$=H, A=S(O$_2$), n=1)

Using the method of Example 82c, the product of Example 91a was converted into the title product, isolated in 60% yield after purification by flash chromatography (EtOAc:hexane (2:3)); TLC, $R_f$=0.29 & 0.35, EtOAc:hexane (1:1).

Analysis calculated for: C$_{26}$H$_{42}$F$_3$N$_3$O$_5$S.2.5H$_2$O: C, 51.13; H, 7.75; N, 6.88. Found: C, 51.12; H, 7.03; N, 6.40.

c. 3S(or R)-Tricyclo[3,3.1$^{3,7}$]dec-1-yl)sulfonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=1-adamantyl, $R^4$=H, A=S(O$_2$), n=1).

Using the method of Example 33c, the product of Example 91b was oxidized to afford, after purification by flash chromatography (EtOAc:hexane (1:1)), the title product (57%) as one substantially pure isomer; HPLC, $t_R$=3.01, Col A, H$_2$O:CH$_3$CN (45:55), FR=2.0.

Analysis calculated for: C$_{26}$H$_{40}$F$_3$N$_3$O$_5$S.O.4H$_2$O: C, 54.70; H, 7.20. Found: C, 54.89; H, 7.17.

EXAMPLE 92

3(RS)-(4-Ethoxycarbonylphenyl)aminocarbonyl-L-phenylglycyl-N-[3-(1,1,1-trifluoro-4-methyl-2-oxopentyl)]-L-prolinamide (Formula Ib, $R^1$=CH(CH$_3$)CH$_3$, $R^2$=$\phi$, $R^3$=4-[CH$_3$CH$_2$O—C(O)]$\phi$, $R^4$=H, A=NHCO, n=1)

a.

2(RS),3(SR)-Phenylmethoxycarbonyl-L-phenylglycyl-N-[3-(1,1,1-trifluoro-2-hydroxy-4-methylpentyl)]-L-prolinamide (Formula VIIb, $R^1$=CH(CH$_3$)CH$_3$, $R^2$=$\phi$, $R^3$=OCH$_2$—, $R^4$=H, A=OCO, n=1)

Using the method of Example 50a, material prepared according to the procedure of Example 76b was allowed to react with CBZ-L-phenyl-glycine to provide, after purification by flash chromatography (MeOH:CH$_2$Cl$_2$ (5:95)), the title product (95%); TLC, $R_f$=0.13 & 0.19, MeOH:CH$_2$Cl$_2$ (5:95).

b.

2(RS),3(SR)-L-Phenylglycyl-N-[3-(1,1,1-trifluoro-2-hydroxy-4-methylpentyl)]-L-prolinamide (Formula IVb, $R^1$=CH(CH$_3$)CH$_3$, $R^2$=$\phi$, $R^4$=H, n=1).

Using the method of Example 2b, material prepared according to the procedure of Example 92a was converted into the title product in 100% yield.

c.

2(RS),3(SR)-(4-Ethoxycarbonylphenyl)aminocarbonyl-L-phenylglycyl-N-[3-(1,1,1-trifluoro-2-hydroxy-4-methylpentyl)]-L-prolinamide (Formula VIIb, $R^1$=CH(CH$_3$)CH$_3$, $R^2$=$\phi$, $R^3$=4-[CH$_3$CH$_2$OC(O)]$\phi$, $R^4$=H, A=NHCO, n=1)

Using the method of Example 15a, material prepared according to the procedure of Example 92b was allowed to react with ethyl 4-isocyanatobenzoate to provide the title product (869°); TLC, $R_f$=0.24 & 0.27, MeOH:Et$_2$O (1:99).

d.

3(RS)-(4-Ethoxycarbonylphenyl)aminocarbonyl-L-phenylglycyl-N-[3-(1,1,1-trifluoro-4-methyl-2-oxopentyl)]-L-prolinamide (Formula Ib, $R^1$=CH(CH$_3$)—CH$_3$, $R^2$=$\phi$, $R^3$=4-[CH$_3$CH$_2$OC(O)]$\phi$, $R^4$=H, A=NHCO, n=1)

Using the method of Example 31c, the product of Example 92c was oxidized to afford, after purification by flash chromatography (gradient, Et$_2$O to CH$_3$CN:Et$_2$O (1:99)), the title product (82%); HPLC, $t_R$=8.88 & 10.82, Col A, CH$_3$CN:H$_2$O (45:55); FR=2.0.

Analysis calculated for: C$_{29}$H$_{33}$F$_3$N$_4$O$_6$.0.64H$_2$O: C, 56.77; H, 5.80; N, 8.75. Found: C, 56.62; H, 5.78; N, 8.78.

EXAMPLE 93

3(RS)-Phenylmethoxy
carbonyl-L-[5-(phenylsulfonylamino)glutamyl]-N-[3-
(1,1,1-trifluoro-4-methyl-2-oxopentyl)]-L-prolinamide
(Formula Ib, $R^1$=CH(CH$_3$)CH$_3$,
$R^2$=$\phi$S(O$_2$)NHC(O)(CH$_2$)$_2$, $R^3$=$\phi$CH$_2$, $R^4$=H,
A=OCO, n=1)

a.

3(RS)-Phenylmethoxycarbonyl-L-glutamyl-N-[3-
(1,1,1-trifluoro-4-methyl-2-oxopentyl)]-L-prolinamide
(Formula Ib, $R^1$=CH(CH$_3$)CH$_3$, $R^2$=HOCO(CH$_2$)$_2$,
$R^3$=$\phi$CH$_2$, $R^4$=H, A=OCO, n=1)

Using the method of Example 14, material prepared according to the procedure of Example 90b was converted into the title product; TLC, $R_f$=0.27, MeOH: CHCl$_3$:AcOH (2.5:95:0.1).

b.

3(RS)-Phenylmethoxycarbonyl-L-[5-(phenylsulfonylamino)glutamyl]-N-[3-(1,1,1-trifluoro-4-methyl-2-oxopentyl)]-L-prolinamide (Formula Ib,
$R^1$=CH(CH$_3$)—CH$_3$, $R^2$=$\phi$S(O$_2$)NHC(O)(CH$_2$)$_2$,
$R^3$=$\phi$CH$_2$—, $R^4$=H, A=OCO, n=1)

Using the method of Example 77b, material prepared according to the procedure of Example 93a was allowed to react with benzenesulfonamide to provide, after purification by flash chromatography (gradient, MeOH:Et$_2$O (2.5:97.5) to (5:95)), the title product (40%); HPLC, $t_R$=7.38 & 10.35, Col A, H$_2$O:CH$_3$CN (65:35), FR=2.5.

Analysis calculated for: C$_{30}$H$_{35}$F$_3$N$_4$O$_8$S.1.5H$_2$O: C, 51.79; H, 5.51; N, 8.19. Found: C, 51.70; H, 5.24; N, 7.89.

EXAMPLE 94

3(RS)-[4-(Phenylsulfonylaminocarbonyl)phenylcarbonyl]-L-valyl-N-[3-(1,1,1-trifluoro-4-methyl-2-oxopentyl)]-L-prolinamide (Formula Ib
$R^1$=CH(CH)CH $R^2$=(CH$_3$)$_2$CH—,
$R^3$=4-[$\phi$S(O$_2$)NH—C(O)]$\phi$, $R^4$=H, A=CO, n=1)

Using the method of Example 89, material prepared according to the procedure of Example 79 was allowed to react with benzenesulfonamide to provide, after purification by flash chromatography (EtOAc: Et$_2$O:AcOH (25:74.9:0.1)), the title product (33%); HPLC, $t_R$=3.71 & 5.65, Col A, H$_2$O: CH$_3$CN (3: 1); FR=2.0.

Analysis calculated for: C$_{30}$H$_{35}$F$_3$N$_4$O$_7$S.1.25H$_2$O: C, 53.36; H, 5.59; N, 8.29. Found: C, 53.75; H, 5.64; N, 7.72.

EXAMPLE 95

3(RS)-[4-[(4-Bromophenyl)sulfonylaminocarbonyl]-
phenylcarbonyl]-L-valyl-N-[3-(1,1,1-trifluoro-4-methyl-2oxopentyl)]-L-prolinamide (Formula Ib,
$R^1$=CH(CH$_3$)CH$_3$, $R^2$=(CH$_3$)$_2$CH—,
$R^3$=4-[(4-Br$\phi$)S(O$_2$)NHC(O)]$\phi$, $R^4$=H, A=CO,
n=1)

a. 4-Bromobenzenesulfonamide

Using the procedure of Example 77a, 4-bromobenzenesulfonyl chloride (10.0 g, 39.6 mmol) was converted into the title product, obtained as white crystals (8.45 g, 92%); m.p. 163°-165°.

b.

3(RS)-[4-[(4-Bromophenyl)sulfonylaminocarbonyl]-
phenylcarbonyl]-L-valyl-N-[3-(1,1,1-trifluoro-4-methyl-2-oxopentyl)]-L-prolinamide (Formula Ib,
$R^1$=CH(CH$_3$)CH$_3$, $R^2$=(CH$_3$)$_2$CH—,
$R^3$=4-[(4-Br-$\phi$)S(O$_2$) NHC(O)]$\phi$, $R^4$=H, A=CO,
n=1)

Using the method of Example 89, material prepared according to the procedure of Example 79 was allowed to react with the product of 95a to provide, after purification by recrystallization from hexane/Et$_2$O, the title product (509°); HPLC, $t_R$=5.25 & 7.84, Col A, H$_2$O:CH$_3$CN (77.5:22.5), FR=2.0.

Analysis calculated for: C$_{30}$H$_{34}$BrF$_3$N$_4$O$_7$S.0.75H$_2$O: C, 48.36; H, 4.80; N, 7.52. Found: C, 48.61; H, 4.89; N, 7.18.

EXAMPLE 96

3(RS)-4-(1-Naphthylsulfonylamino)-1,4-dioxobutyl-L-valyl-N-[3-(1,1,1-trifluoro-4-methyl-2-oxopentyl)]-L-prolinamide (Formula Ib, $R^1$=CH(CH$_3$)CH$_3$,
$R^2$(CH$_3$)$_2$CH—, $R^3$=1-naphthyl-S(O$_2$)NHC(O)(CH$_2$)$_2$,
$R^4$=H, A=CO, n=1)

Using the method of Example 89 material prepared according to the procedure of Example 14 was allowed to react with 1-naphthalenesulfonamide to provide, after purification by flash chromatography (MeOH:CHCl$_3$ (5:95)), the title product (46%); HPLC, $t_R$=4.09 & 6.57, Col A, H$_2$O:CH$_3$CN (60:40), FR=2.0.

Analysis calculated for: C$_{30}$H$_{37}$F$_3$N$_4$O$_7$S.0.5H$_2$O: C, 54.29; H, 5.77; N, 8.44. Found: C, 54.33; H, 6.01; N, 8.09.

EXAMPLE 97

3(RS)-[2-(4-Aminocarbonylphenoxy)-1-oxoethyl]-L-valyl-N-[3-(1,1,1-trifluoro-4-methyl-2-oxopentyl)]-L-prolinamide (Formula Ib, $R^1$=CH(CH$_3$)CH$_3$,
$R^2$=(CH$_3$)$_2$CH—, $R^3$=4-[[H$_2$NC(O)]$\phi$OCH$_2$, $R^4$=H,
A=CO, n=1)

a. 4-Aminocarbonylphenoxyacetic acid methylester

A mixture of p-hydroxybenzamide (3.43 g), methyl bromoacetate (2.37 ml) and K$_2$CO$_3$ (3.45 g) was stirred for 12 hr in 25 ml of DMF. The reaction mixture was diluted with water (150 ml); the solid was filtered, washed with water, and air dried. Crystallization from ethanol gave 3.3 g (63%) of the title compound as white crystals.

b. 4-Aminocarbonylphenoxyacetic acid

A mixture of the product of Example 97a (3.3 g) in 0.5 N NaOH (30 ml) was stirred for 3 hr. The solution was filtered and the filtrate made acidic (pH 1) with 1N HCl. The solid was filtered and air dried to yield 3.0 g (97%) of the title acid as a white powder; mp 255°-256°.

c.

2(RS),3(SR)-[2-(4-aminocarbonylphenoxy)-1-oxoethyl]-L-valyl-N-[3-(1,1,1-trifluoro-2-hydroxy-4-methylpentyl)]-L-prolinamide (Formula VIIb,
$R^1$=CH(CH$_3$)CH$_3$, $R^2$=(CH$_3$)$_2$CH—,
$R^3$=4-[H$_2$NC(O)]$\phi$OCH$_2$, $R^4$=H, A=CO, n=1)

Using the method of Example 32a, material prepared by the procedure of Example 5d was allowed to react with material prepared according to Example 97b to provide the title compound, isolated in 33% yield; TLC, $R_f$=0.27 & 0.31, MeOH:CH$_2$Cl$_2$ (1:9).

d.
3(RS)-[2-(4-Aminocarbonylphenoxy)-1-oxoethyl]-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[H$_2$NC(O)]$\phi$OCH$_2$, $R^4$=H, A=CO, n=1)

Using the method of Example 61c, the product of Example 97c was oxidized to afford, after purification by flash chromatography (MeOH:CH$_2$Cl$_2$ (4:96)), the title product (35%); TLC, $R_f$=0.37, MeOH:CHCl$_3$ (1:9).

Analysis calculated for: C$_{25}$H$_{33}$F$_3$N$_4$O$_6$·1.5H$_2$O: C, 52.72; H, 6.37; N, 9.83. Found: C, 52.78; H, 6.03; N, 9.65.

EXAMPLE 98

3(RS)-(4-Hydroxycarbonylphenyl)methoxycarbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[HOC(O)]$\phi$CH$_2$, $R^4$=H, A=OCO, n=1)

Using the method of Example 14, material prepared according to the procedure of Example 86c was converted into the title product and isolated by preparative TLC (MeOH:CHCl$_3$ (15:85)) in 45% yield; HPLC, $t_R$=2.27 & 3.02, Col A, H$_2$O:CH$_3$CN (60:40), FR=2.0.

Analysis calculated for: C$_{25}$H$_{32}$F$_3$N$_3$O$_7$·2H$_2$O: C, 51.81; H, 6.26; N, 7.25. Found: C, 51.75; H, 5.63; N, 7.15.

EXAMPLE 99

3(RS)-[4-[4-(2-Amino-2-oxoethyl)phenoxy]-1-oxobutyl]-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH, $R^3$=4-[H$_2$NC(O)CH$_2$]$\phi$O(CH$_2$)$_3$, $R^4$=H, A=CO, n=1)

a. 4-(4-Aminocarbonylphenoxy)butanoic acid ethyl ester

A mixture of p-hydroxyphenylacetamide (3.8 g), ethyl 4-bromobutyrate (3.6 ml) and K$_2$CO$_3$ (3.45 g) was stirred for 12 hr in DMF (30 ml). The mixture was diluted with water (100 ml); the solid was filtered and air dried. Crystallization of the solid from ethanol gave 4 g (60%) of the title compound as white crystals; mp 144.5°-145.5°.

b. 4-(4-Aminocarbonylphenoxy)butanoic acid

A mixture of the product of Example 99a (3.97 g) in 1N NaOH (20 ml) was stirred overnight at room temperature. The solution was filtered and made acidic with 1N HCl. The solid was filtered and dried under high vacuum to yield 3 g (82%) of the title compound as a white powder; m.p. 162.5°-164°.

c.
2(RS),3(SR)-[4-[4-(2-Amino-2-oxoethyl)phenoxy]-1-oxobutyl]-L-valyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_3$)$_2$CH—, $R^3$=4-[H$_2$NC(O) CH$_2$]$\phi$O(CH$_2$)$_3$, $R^4$=H, A=CO, N=1)

Using the method of Example 32a, material prepared by the procedure of Example 5d was allowed to react with the product of Example 99b to provide the title compound, isolated in 71% yield; TLC, $R_f$=0.28 & 0.31, MeOH:CHCl$_3$ (1:9).

d.
3(RS)-[4-(2-amino-2-oxoethyl)phenoxy]-1-oxobutyl]-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[H$_2$NC(O)CH$_2$]$\phi$O(CH$_2$)$_3$, $R^4$=H, A=CO, n=1)

Using the method of Example 61c, the product of Example 99c was oxidized to afford, after purification by flash chromatography (MeOH:CH$_2$Cl$_2$ (4:96)), the title product (32%); HPLC, $t_R$=2.11 & 3.01, Col B, H$_2$O: CH$_3$CN: THF :TFA (55: 35: 15:0.1), FR=2.0.

Analysis calculated for: C$_{28}$H$_{39}$F$_3$N$_4$O$_6$·5H$_2$O: C, 56.65; H, 6.79; N, 9.43. Found: C, 56.83; H, 6.98; N, 9.24.

EXAMPLE 100

3(RS)-E-[3-(4-Hydroxycarbonylphenyl)-1-oxoprop-2-enyl]-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=E-4-[HOC(O)]$\phi$CH=CH—, $R^4$=H, A=CO, n=1)

Using the method of Example 14, material prepared according to the procedure of Example 87d was converted into the title product in 88% yield; HPLC, $t_R$=2.6 & 3.4, Col B, H$_2$O:CH$_3$CN: THF:TFA (55:35:15: 0.1), FR=1.5.

Analysis calculated for: C$_{26}$H$_{32}$F$_3$N$_3$O$_6$·0.35H$_2$O: C, 57.21; H, 6.03; N, 7.96. Found: C, 57.40; H, 6.40; N, 7.38.

EXAMPLE 101

3(RS)-[2-(4-Ethoxycarbonylphenoxy)-1-oxoethyl]-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[CH$_3$CH$_2$OC(O)]$\phi$OCH$_2$, $R^4$=H, A=CO, n=1)

a. Ethyl 4-[2-Oxo-2-(phenylmethoxy)ethoxy]benzoate

A mixture of ethyl p-hydroxybenzoate (4.98 g), benzyl bromoacetate (4.75 ml) and K$_2$CO$_3$ (4.14 g) was stirred for 15 hr in 30 ml of DMF. The reaction mixture was diluted with water (200 ml) and extracted with a 1:1 ether:hexane mixture. The combined organic extracts were washed (water, brine), dried (Na$_2$SO$_4$), filtered, and evaporated leaving 9.3 g, (99%) of the title compound as a heavy oil; TLC, $R_f$=0.71, Et$_2$O: hexane (1:1).

b. Ethyl 4-(2-Hydroxy-2-oxoethoxy)benzoate

A solution of the product of Example 101a (2.0 g) in EtOH (50 ml) was hydrogenated at 170,000 Pascals (10 psi) using 10% Pd/C (200 mg). After 20 min the reaction was complete and the reaction mixture was filtered through a pad of Celite ® and concentrated under vacuum. The residue was crystallized from methyl tert-butyl ether/hexane affording 900 mg (63%) of the title compound as fine white needles; mp 129°-130°.

c.
2(RS),3(SR)-[2-(4-Ethoxycarbonylphenoxy)-1-oxoethyl]-L-valyl-N-[3-(1,1,1-trifluoro-2-hydroxy-4-methylpentyl)]-L-prolinamide (Formula VIIb, $R^1$=CH(CH$_3$)CH$_3$, $R^2$=(CH$_3$)$_2$CH—, $R^3$=4-[CH$_3$CH$_2$OC(O)]$\phi$OCH$_2$, $R^4$=H, A=CO, n=1)

Using the method of Example 32a, material prepared by the procedure of Example 5d was allowed to react with the product of Example 101b to provide the title compound, isolated in 92% yield; TLC, $R_f$=0.47 & 0.53, MeOH:CH$_2$Cl$_2$ (1:9).

d.

3(RS)-[2-(4-Ethoxycarbonylphenoxy)-1-oxoethyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH, R$^3$=4-[CH$_3$CH$_2$OC(O)]$\phi$OCH$_2$, R$^4$=H, A=CO, n=1)

Using the method of Example 61c, the product of Example 101c was oxidized to afford, after purification by flash chromatography (MeOH: CH$_2$Cl$_2$ (2: 98)), the title product (41%); TLC, $R_f$=0.37, MeOH:CHCl$_3$ (1:9).

Analysis calculated for: C$_{27}$H$_{36}$F$_3$N$_3$O$_7$: C, 56.74; H, 6.35; N, 7.35. Found: C, 56.40; H, 6.50; N, 7.12.

EXAMPLE 102

3(RS)-[3-(4-Ethoxycarbonylphenyl)-1-oxopropyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH, R$^3$=4-[CH$_3$CH$_2$OC(O)]$\phi$(CH$_2$)$_2$—, R$^4$=H, A=CO, n=1)

a. 4-Ethoxycarbonylbenzenepropanoic acid

A solution of 4-carbethoxycinnamic acid (4.9 g) in EtOH (120 ml) was hydrogenated over 5% Rh/C (485 mg) at atmospheric pressure for 21 hr. The solution filtered and stripped. The residue was crystallized from cyclohexane to afford 2.23 g (46%) of the title compound as white crystals; mp 108.5°–110.5°.

b.

2(RS),3(SR)-[3-(4-Ethoxycarbonylphenyl)-1-oxopropyl]-L-valyl-N-[3-(1,1,1-trifluoro-2-hydroxy-4-methylpentyl)]-L-prolinamide (Formula VIIb, R$^1$=CH(CH$_3$)CH$_3$, R$^2$=(CH$_3$)$_2$CH—, R$^3$=4-[CH$_3$CH$_2$OC(O)]$\phi$(CH$_2$)$_2$—, R$^4$=H, A=CO, n=1)

Using the method of Example 32a, material prepared by the procedure of Example 5d was allowed to react with the product of Example 102a to produce the title compound, isolated in 83% yield after purification by flash chromatography (MeOH:CH$_2$Cl$_2$ (4:96)); TLC, $R_f$=0.33 & 0.38, MeOH:CH$_2$Cl$_2$(5:95).

c.

3(RS)-[3-(4-Ethoxycarbonylphenyl)-1-oxopropyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[CH$_3$CH$_2$OC(O)]$\phi$(CH$_2$)$_2$—, R$^4$=H, A=CO, n=1)

Using the method of Example 84d, the product of Example 102b was oxidized to afford the title product (97%).

Analysis calculated for: C$_{28}$H$_{38}$F$_3$N$_3$O$_{6}$.0.65 H$_2$O: C, 57.85; H, 6.81; N, 7.23. Found: C, 57.89; H, 6.83; N, 6.98.

EXAMPLE 103

3(RS)-4-Hydroxybenzoyl-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-(HO)$\phi$, R$^4$=H, A=CO, n=1)

a.

2(RS),3(SR)-4-Hydroxybenzoyl-L-valyl-N-[3-(1,1,1-trifluoro-2-hydroxy-4-methylpentyl)]-L-prolinamide (Formula VIIb, R$^1$=CH(CH$_3$)CH$_3$, R$^2$=(CH$_3$)$_2$CH—, R$^3$=4-(HO)$\phi$, R$^4$=H, A=CO, n=1)

Using the method of Example 84b, material prepared by the procedure of Example 5d was allowed to react with 4-hydroxybenzoic acid to provide the title compound which was isolated in 65% yield after purification by flash chromatography (EtOAc:Et$_2$O (15:85)); TLC, $R_f$=0.43, EtOAc:Et$_2$O (15:85).

Analysis calculated for: C$_{23}$H$_{32}$F$_3$N$_3$O$_5$.0.6H$_2$O: C, 55.43; H, 6.71; N, 8.43. Found: C, 55.76; H, 6.62; N, 8.03.

b.

3(RS)-4-Hydroxybenzoyl-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-(HO)$\phi$, R$^4$=H, A=CO, n=1)

The product of Example 103a was oxidized by the method of Example 33c with the following, modified workup: The crude residue was dissolved in MeOH and stirred with aq K$_2$CO$_3$ (5 ml) at room temperature for 16 hr. After the mixture was partially concentrated under vacuum, it was acidified with conc HCl and extracted with EtOAc. The EtOAc solution was washed (brine), dried (Na$_2$SO$_4$), filtered, and concentrated to a residue which was purified by flash chromatography (EtOAc:Et$_2$O (1:9)) to afford the title compound in 38% yield; HPCL, $t_R$=3.54 & 4.92, Col A, CH$_3$CN:H$_2$O (35:65), FR=2.0.

Analysis calculated for: C$_{23}$H$_{30}$F$_3$N$_3$O$_5$.1.2 H$_2$O: C, 54.47; H, 6.44; N, 6.29. Found: C, 54.83; H, 6.49; N, 7.89.

EXAMPLE 104

3(RS)-[4-[(4-Chlorophenyl)sulfonylaminocarbonyl]-phenylcarbonyl]-L-valyl-N-[3-(1,1,1-trifluoro-4-methyl-2oxopentyl) ]-L-prolinamide (Formula Ib, R$^1$=CH(CH$_3$)CH$_3$, R$^2$=(CH$_3$)$_2$CH, R$^3$=4-[(4-Cl$\phi$)S(O$_2$)NHC(O)]$\phi$—, R$^4$=H, A=CO, n=1)

Using the method of Example 77b, material prepared according to the procedure of Example 79 was allowed to react with 4-chlorobenzenesulfonamide to provide, after purification by flash chromatography (MeOH:CH$_2$Cl$_2$ (3:97)) and acidification of the chromatographed product with MeOH and 1N HCl as described in Example 121d, the title product (66%), HPLC, $t_R$=4.26 & 6.07, Col A, H$_2$O:CH$_3$CN:THF:TFA (55:35:15:0.1).

EXAMPLE 105

3(RS)-[3-(4-Hydroxycarbonylphenyl)-1-oxopropyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[HOC(O)]$\phi$(CH$_2$)$_2$, R$^4$=H, A=CO, n=1)

Using the method of Example 14, material prepared according to the procedure of Example 102c was converted into the title product in 81% yield; HPLC, $t_R$=2.6 & 3.4, Col B, H$_2$O:CH$_3$CN:THF:TFA (55:35: 15:0.1).

Analysis calculated for: C$_{26}$H$_{34}$F$_3$N$_3$O$_6$: C, 57.66; H, 6.33; N, 7.76. Found: C, 56.98; H, 6.49; N, 7.35.

EXAMPLE 106

3(RS)-[3-[4-[(4-Chlorophenyl)sulfonylaminocarbonyl]-phenyl]-1-oxopropyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[(4-Cl$\phi$)S(O$_2$)NHC(O)]$\phi$(CH$_2$)$_2$, R$^4$=H, A=CO, n=1)

Using the method of Example 77b, material prepared according to the procedure of Example 105 was allowed to react with 4-chlorobenzenesulfonamide to provide, after purification by flash chromatography (MeOH:CH$_2$Cl$_2$(5:95)), the title product (90%); HPLC, $t_R$=3.96 & 5.73, Col B, H$_2$O:CH$_3$CN:THF:TFA (55:35:15: 0.1), FR=3.0.

Analysis calculated for: C$_{32}$H$_{38}$C$_1$F$_3$N$_4$O$_7$S.1.7 H$_2$O: C, 51.53; H, 5.59; N, 7.51. Found: C, 51.72; H, 5.40; N, 7.24.

EXAMPLE 107

3(RS)-E-[3-[4-[(4-Chlorophenyl)sulfonylaminocarbonyl]phenyl]-1-oxoprop-2-enyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=E-[4-[(4-Cl$\phi$)S(O$_2$)NHC(O)]$\phi$—CH=CH—, R$^4$=H, A=CO, n=1)

Using the method of Example 77b, material prepared according to the procedure of Example 100 was allowed to react with 4-chlorobenzenesulfonamide to provide, after purification by flash chromatography (MeOH:CH$_2$Cl$_2$(5:95)), the title product (97%); HPLC, $t_R$=4.73 & 6.68, Col B, H$_2$O:CH$_3$CN:THF:TFA (55:35:15: 0.1), FR=3.0.

Analysis calculated for: C$_{32}$H$_{36}$C$_1$F$_3$N$_4$O$_7$S.1.7 H$_2$O: C, 51.67; H, 5.33; N, 7.53. Found: C, 51.72; H, 5.40; N, 7.24.

EXAMPLE 108

3(RS)-[1-[4-[[(4-Bromophenyl)sulfonyl][phenylmethyl]aminocarbonyl]phenyl]-1-oxomethyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[(4-Br$\phi$)S(O$_2$)N(CH$_2$$\phi$)C(O)]$\phi$—, R$^4$=H, A=CO, n=1)

a. 4-Bromo-N-(phenylmethyl)benzenesulfonamide

4-Bromobenzenesulfonyl chloride (14.05 g, 55 mmol) was added to a stirred solution of benzylamine (5.36 g, 50 mmol) and pyridine (400 ml) under nitrogen at room temperature. The resulting reaction mixture was stirred for 1 hr; then it was poured onto ice/water (800 ml) to form a yellow precipitate which was filtered and recrystallized from EtOH/water to give 9.44 g (53%) of the title compound as off-white needles, mp 116°–117° C.

Analysis calculated for: C$_{13}$H$_{12}$BrNO$_2$S: C, 47.87; H, 3.71; N, 4.29. Found: C, 48.02; H, 3.78; N, 4.25.

b. 1,1-Dimethylethyl 4-[[(4-bromophenyl)sulfonyl]-[phenylmethyl]aminocarbonyl]benzoate DMAP (1.81 g, 14.84 mmol) was added to a stirred solution of the product of Example 108a (4.4 g, 13.49 mml) and CH$_2$Cl$_2$ (150 ml) at room temperature. To the resulting solution, WSCDI (2.84 g, 14.84 mmol) and terephthalic acid mono t-butylester (3.0 g, 13.49 mmol) were successively added. The reaction mixture was stirred at room temperature overnight and concentrated under vacuum to leave a residue which was dissolved in EtOAc. The EtOAc solution was washed (20% aq citric acid solution, brine, water), dried (MgSO$_4$), filtered, and concentrated under vacuum to leave an oily residue. This residue was dissolved in warm EtOH and allowed to cool. The white crystals which formed were filtered, washed with cold EtOH, and dried under high vacuum to give 5.72 g (80%) of the title compound as white crystals; m.p. 120°–122° C.

Analysis calculated for: C$_{25}$H$_{24}$BrNO$_5$S: C, 56.61; H, 4.56; N, 2.64. Found: C, 56.84; H, 4.68; N, 2.60.

c. 4-[[(4-Bromophenyl)sulfonyl][phenylmethyl]aminocarbonyl]benzoic acid

The product of Example 108b (5.30 g, 10 mmol) was added to TFA (50 ml) at 0° and dissolved immediately upon addition. After about 10 min a white precipitate formed; stirring was continued for ½ hr before the mixture was filtered. The collected solid was washed with water and recrystallized from hot absolute EtOH to give 4.0 g (84%) of the title compound as a white powder; m.p. 193°–194° C.

d. 2(RS),3(RS)[1-[4-[[(4-Bromophenyl)sulfonyl][phenylmethyl]aminocarbonyl]phenyl]-1-oxomethyl]-L-valyl-N-[3-(1,1,1-trifluoro-2-hydroxy-4-methylpentyl)]-L-prolinamide (Formula VIIb, R$^1$=CH(CH$_3$)CH$_3$, R$^2$=CH(CH$_3$)CH$_3$, R$^3$=4-[[(4-Br$\phi$)S(O$_2$)][$\phi$CH$_2$]NCO]$\phi$, R$^4$=H, A=CO, n=1

WSCDI (0.44 g, 2.3 mmol) was added to a stirred solution of the product of Example 108c (1.0 g, 2.1 mmol), material prepared according to Example 5d (0.85 g, 2.3 mmol), HOBT (0.28 g, 2.1 mmol) and dry THF under nitrogen at 0°. The resulting reaction mixture was stirred at 0° C. for 15 min; then it was allowed to warm to room temperature and stirred for 4 hr. The THF was removed under vacuum to leave a brownish residue which was dissolved in EtOAc. The EtOAc solution was washed (1N HCl, satd NaHCO$_3$, brine) and dried (MgSO$_4$), filtered, and concentrated under vacuum to leave a residue (1.6 g). A (1.27 g) portion of this residue was recrystallized from methyl t-butyl ether/hexane to give 0.64 g (49% overall yield) of the title compound as a white powder; TLC, R$_f$=0.59 & 0.64, CHCl$_3$:CH$_3$OH (95:5); HPLC; $t_R$=14.34 & 15.26, Col B, H$_2$O:CH$_3$CN:THF:TFA (55:35:15:0.1), FR=3.0.

e. 3(RS)-[1-[4-[[(4-Bromophenyl)sulfonyl][phenylmethyl]aminocarbonyl]phenyl]-1-oxomethyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[[(4-Br$\phi$)S(O$_2$)]N(CH$_2$$\phi$)C(O)]$\phi$, R$^4$=H, A=CO, n=1)

A solution of the product of Example 108d (300 mg, 0.364 mmol) in CH$_2$Cl$_2$ (2 ml) was added to a stirred mixture of a Dess-Martin periodinane (1.54 g, 3.63 mmol) and dry CH$_2$Cl$_2$ (10 ml) under nitrogen at room temperature. To the resulting mixture, TFA (0.41 g, 3.63 mmol) was added; whereupon the mixture immediately became clear; then, after 10 min, became cloudy. Stirring was continued overnight before EtOAc (50 ml) was added, and the resulting mixture was poured into saturated aq NaHCO$_3$ (100 ml) containing 4 g of Na$_2$S$_2$O$_3$. The two phase mixture was stirred vigorously for 10 min. The organic layer was separated, washed (satd NaHCO$_3$ (100 ml), brine (100 ml)), dried (MgSO$_4$), filtered, concentrated under vacuum, and dried under high vacuum to give 0.24 g (80%) of the title compound as a white powder; TLC, R$_f$=0.62 & 0.75, CHCl$_3$: MeOH (95:5); HPLC, t$_R$=14.88 & 21.56, Col B, H$_2$O: CH$_3$CN: THF:TFA (55:35:15:0.1), FR=3.0.

Analysis calculated for: C$_{37}$H$_{40}$BrF$_3$N$_4$O$_7$S.0.25H$_2$O: C, 53.78; H, 4.94; N, 6.78. Found: C, 53.84.; H, 4.98; N, 6.45.

EXAMPLE 109

3R(orS)-(Tricyclo[3.3.1.1$^{3,7}$]dec-1-yl)sulfonyl-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=1-adamantyl, R$^4$=H, A=S(O$_2$), n=1)

From the flash chromatography described in Example 91c was obtained the title compound as the other substantially pure isomer (84%); HPLC, t$_R$=3.89, Col A, H$_2$O:CH$_3$CN (45:55), FR=2.0.

Analysis calculated for: C$_{26}$H$_{40}$F$_3$N$_3$O$_5$S.0.5H$_2$O: C, 54.57; H, 7.22; N, 7.34. Found: C, 54.52; H, 7.15; N, 7.33.

EXAMPLE 110

3S (orR)-[4-(Phenylsulfonylaminocarbonyl)-phenylaminocarbonyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[$\phi$S(O$_2$)NHC(O)]$\phi$, R$^4$=H, A=NHCO, n=1)

The two diastereomers of Example 58 were separated by MPLC on a LiChroprep ® RP-8 column (Merck, Size B 40–63 μm) using MeOH:H$_2$O (50:50) as eluent. The fractions collected were analyzed by HPLC, and the appropriate fractions were combined and lyophilized to give the title product; HPLC, t$_R$=4.5, Col B, H$_2$O: CH$_3$CN:THF:TFA (55:35:15:0.1), FR=2.0.

EXAMPLE 111

3S(or R)-Phenylmethoxycarbonyl-L-phenylglycyl-N-[3-(1,1,1-trifluoro-4-methyl-2-oxopentyl)]-L-prolinamide (Formula Ib, R$^1$=CH(CH$_3$)CH$_3$, R$^2$=$\phi$, R$^3$=$\phi$CH$_2$—, R$^4$=H, A=OCO, n=1)

Using the method of Example 61c, the product prepared by the method of Example 92a was oxidized to afford, after purification by flash chromatography (MeOH:CH$_2$Cl$_2$ (1.5:98.5)), the title product (80%) as one substantially pure isomer; TLC, R$_f$=0.26, pentane: MeOH:Et$_2$O (25:1:99).

Analysis calculated for: C$_{27}$H$_{30}$F$_3$N$_3$O: C, 60.78; H, 5.67; N, 7.88. Found: C, 60.64; H, 5.85; N, 7.96.

EXAMPLE 112

3R(orS)-Phenylmethoxycarbonyl-L-phenylglycyl-N-[3-(1,1,1-trifluoro-4-methyl-2-oxopentyl)]-L-prolinamide (Formula Ib, R$^1$=CH(CH$_3$)CH$_3$, R$^2$=$\phi$, R$^3$=$\phi$CH$_2$—, R$^4$=H, A=OCO, n=1)

From the flash chromatography described in Example 111 was obtained the title product (83%) as the other substantially pure isomer; TLC, R$_f$=0.30, pentane:MeOH:Et$_2$O (25:1:99).

Analysis calculated for: C$_{27}$H$_{30}$F$_3$N$_3$O$_5$: C, 60.78; H, 5.67; N, 7.88. Found: C, 59.43; H, 5.65; N, 7.48.

EXAMPLE 113

3R(orS)-[4-[(4-Bromophenyl)sulfonylaminocarbonyl]-phenylcarbonyl]-L-valyl-N-[3-(1,1,1-trifluoro-4-methyl-2-oxo-pentyl)]-L-prolinamide (Formula Ib, R$^1$=CH(CH$_3$)CH$_3$, R$^2$=(CH$_3$)$_2$CH—, R$^3$=4-[4-(Br$\phi$)S(O$_2$)NHC(O)]$\phi$, R$^4$=H, A=CO, n=1)

The product of Example 95b (0.5 g, 0.7 mmol) was chromatographed by MPLC on a LiChroprep ® RP-8 column (Merck, size B 40–63 μm) using MeOH:H$_2$O (60: 40) as eluent. The fractions collected were evaluated by HPLC, combined, and lyophilized to give two products. The title product (0.147 g) was obtained as a substantially pure isomer; HPLC, t$_R$=12.38, Col B, H$_2$O: CH$_3$CN: T}{F: TFA (55: 35: 15:0.1), FR=3.0.

EXAMPLE 114

3S (or R)-[4-[(4-Bromophenyl)sulfonylaminocarbonyl]phenylcarbonyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[(4-Br$\phi$)S(O$_2$)NHC(O)]$\phi$, R$^4$=H, A=CO, n=1)

The other product obtained in the separation described in Example 113 was the title product (0.065 g), obtained as a substantially pure isomer; HPLC, t$_R$=8.44, Col B, H$_2$O:CH$_3$CN:THF:TFA (55:35:15:0.1), FR=3.0.

EXAMPLE 115

3S(or R)-[4-[(4-Chlorophenyl)sulfonylaminocarbonyl]phenylcarbonyl]-L-valyl-N-[3-(1,1,1-trifluoro-4-methyl-2-oxopentyl)]-L-prolinamide (Formula Ib, R$^1$=CH(CH$_3$)CH$_3$, R$^2$=(CH$_3$)$_2$CH—, R$^3$=4-[(4-Cl$\phi$)S(O$_2$)NHC(O)]$\phi$, R$^4$=H, A=CO, n=1)

A portion of material prepared as described in Example 104 (544.8 mg) was dissolved in H$_2$O:CH$_3$CN: THF (2.2 ml:3.3 ml:0.5 ml) and was separated by MPLC on a Lobar ® size B LiChroprep ® RP-8 column using H$_2$O: CH$_3$CN:THF:TFA (55:32.5:12.5:0.1). After analysis by HPLC, the appropriate fractions were combined, concentrated under vacuum, and dried under high vacuum at 43° to afford the title compound (255 mg) as a white amorphous solid; HPLC, t$_R$=5.76, Col B, H$_2$O:CH$_3$CN:THF: TFA (55:32.5:12.5:0.1), FR=3.0.

Analysis calculated for: C$_{30}$H$_{34}$C$_1$F$_3$N$_4$O$_7$S.1.3H$_2$O: C, 50.71; H, 5.19; N, 7.89. Found: C, 50.88; H, 4.87: N, 7.70.

EXAMPLE 116

3R(or
S)-[4-[(4-Chlorophenyl)sulfonylaminocarbonyl]-phenyl]carbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=(CH$_3$)$_2$CH—, $R^3$=4-[(4-Cl$\phi$)S(O$_2$)NHC(O)]$\phi$, $R^4$=H, A=CO, n=1)

A portion of material prepared as described in Example 104 (573.8 mg) was dissolved in H$_2$O:THF (2 ml:3 ml) and was separated by MPLC on a Lobar® size B LiChroprep® RP-8 column using THF:H$_2$O:TFA (41:59:0.1) as eluent. After analysis by HPLC, the appropriate fractions were combined and lyophilized to afford the title compound (51.8 mg) as a substantially pure isomer (99:1 by HPLC); HPLC, $t_R$=8.8, Col B, H$_2$O:CH$_3$CN: THF:TFA (55:32.5:12.5:0.1), FR=3.0.

EXAMPLE 117

3S(or
R)-Phenylmethoxycarbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)CH$_3$, $R^3$=$\phi$CH$_2$ $R^4$=H, A=OCO, n=1)

A portion of material prepared according to the method of Example 11 (10 g, 0.02 mol) was separated into its individual substantially optically pure isomers by flash chromatography (1 kg of silica gel, Et$_2$O:hexane (80:20)). Combination of the appropriate fractions afforded the title compound (3.17 g) as a substantially pure isomer; HPLC, $t_R$=5.65, Col A, H$_2$O:CH$_3$CN (55:45), FR=2.0.

Analysis calculated for: C$_{24}$H$_{32}$F$_3$N$_3$O$_5$.H$_2$O: C, 55.47; H, 6.46; N, 8.08. Found: C, 55.50; H, 6.77; N, 7.99.

EXAMPLE 118

3R(or
S)-Phenylmethoxycarbonyl-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)CH$_3$, $R^3$=$\phi$CH$_2$, $R^4$=H, A=OCO, n=1)

From the separation described in Example 117 combination of the appropriate fractions afforded the title compound (3.67 g) as the other a substantially pure isomer.

Analysis calculated for: C$_{24}$H$_{32}$F$_3$N$_3$O$_5$: C, 57.71; H, 6.46; N, 8.41. Found: C, 57.61; H, 6.34; N, 7.96.

EXAMPLE 119

3S(or
R)-[(4-Carboxyphenyl)aminocarbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)CH$_3$, $R^3$=4-(HOOC)$\phi$, $R^4$=H, A=NHCO, n=1)

A portion of a product prepared as described in Example 16 (500 mg) was separated by MPLC on a Lobar® size B LiChroprep® RP-8 column using MeOH:H$_2$O (1:1) as eluent. After analysis by HPLC, the appropriate fractions were combined to afford the title compound (150 mg) as a substantially pure isomer; HPLC, $t_R$=6.58, Col A, CH$_3$CN:H$_2$O (25:75), FR=2.0.

EXAMPLE 120

3R(or
S)-[(4-Carboxyphenyl)aminocarbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)CH$_3$, $R^3$=4-(HOOC)$\phi$, $R^4$=H, A=NHCO, n=1)

By combination of the appropriate fractions from the separation described in Example 119, the title compound was obtained as a highly enriched isomer (220 mg) in a ratio of 90.4:9.5 with the isomer described in Example 119; HPLC, $t_R$=11.09, Col A, CH$_3$CN:H$_2$O (25:75), FR=2.0.

EXAMPLE 121

3(RS)-[4-[(4-Chlorophenyl)sulfonylaminocarbonyl]-phenylcarbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)CH$_3$, $R^3$=4-[(4-Cl$\phi$)S(O$_2$)NHCO]$\phi$, $R^4$=H, A=CO, n=1)

A preferred method for conversion of material prepared using the method of Example 5d into the title compound is as follows:

a. 1,1-Dimethylethyl 4-[(4-chlorophenyl)sulfonylaminocarbonyl]benzoate

A 5-liter 3-neck round bottom flask was equipped with a mechanical stirrer and nitrogen inlet. CH$_2$Cl$_2$ (2 liters) was placed in the reaction flask and terephthalic acid mono-t-butyl ester (127.5 g, 0.574 mol), DMAP (70.06 g, 0.574 mol), and 4-chlorobenzenesulfonamide (110.04 g, 0.574 mol) were added in that order using CH$_2$Cl$_2$ (400 ml) to wash down the solids. WSCDI (110.10 g, 0.574 mol) was added in portions over 10 min using CH$_2$Cl$_2$ (100 ml) to wash down the solid. After the reaction mixture was stirred overnight at room temperature, it was concentrated under vacuum to dryness. The residue was partioned between EtOAc and water. The EtOAc solution was washed (20% aq citric acid, satd aq NaHCO$_3$, brine), dried (Na$_2$SO$_4$), and concentrated under vacuum to a white solid. After drying in a vacuum oven at 50°, the title product (227 g, 100%) was obtained in a sufficiently pure state to be used directly for the next step; TLC, $R_f$=0.43, MeOH:CHCl$_3$ (15:85). (Further purification was possible by recrystallization from EtOH:water; m.p. above 300°).

b. 4-[(4-Chlorophenyl)sulfonylaminocarbonyl]benzenecarboxylic acid

A 3-liter 3-neck round bottom flask was equipped with a mechanical stirrer and a CaCl$_2$ drying tube. TFA (1300 g) was added and cooled to 0°; and the product of Example 121a (79.5 g, 0.20 mol) was added. Initially, the solid dissolved, giving a clear solution. After 10–15 min, a heavy precipitate of product formed, and it was difficult to stir the reaction mixture. Vigorous stirring with the mechanical stirrer was essential to drive the reaction to completion. The reaction mixture was stirred at 0°-5° for 1 hr before it was poured onto 1500 ml of ice/water and stirred for 2 hr. The resulting solid was filtered and dried. The white solid (61.5 g, 91%) obtained was recrystallized from 1600 ml absolute EtOH/1600 ml H$_2$O to yield the title product (54 g, 80%) as white needles; m.p.=286°-288°; TLC, $R_f$=0.7, MeOH:CHCl$_3$: AcOH (10:90:1).

c.
2(RS),3(SR)-[4-[(4-Chlorophenyl)sulfonylaminocarbonyl]phenylcarbonyl]-L-valyl-N-[3-(1,1,1-trifluoro-2-hydroxy-4-methylpentyl)]-L-prolinamide (Formula VIIb, $R^1$=CH(CH$_3$)CH$_3$, $R^2$=CH(CH$_3$)CH$_3$, $R^3$=4-[(4Cl-$\phi$)S(O$_2$)NHCO]$\phi$, $R^4$=H, A=CO, n=1)

A 250 ml 3-neck round bottom flask was equipped with a magnetic stirrer and nitrogen inlet. To CH$_2$Cl$_2$ (125 ml) in the reaction flask, the product of Example 121b (5.45 g, 16.07 mmol), DMAP (1.96 g, 16.07 mmol), and material prepared according to Example 5d (6.20 g, 16.87 mmol) were added using CH$_2$Cl$_2$ (20 ml) to wash down the solids; then, WSCDI (3.24 g, 16.87 mmol) was added using CH$_2$Cl$_2$ (5 ml) to wash down the solid. After the reaction mixture had been stirred for 5 hr, it was washed (1N HCl, satd aq NaHCO$_3$, brine), dried (Na$_2$SO$_4$), and concentrated under vacuum to afford a crude product (11.0 g, 100%) as a white solid. A portion (3.39 g) of this crude product was dissolved in MeOH (40 ml) and diluted with water (9 ml). The resulting solution was saturated with K$_2$CO$_3$ and stirred overnight at room temperature. After most of the MeOH had been removed under vacuum, the residue was partitioned between EtOAc and water. The EtOAc solution was washed (satd aq NaHCO$_3$, brine), dried (Na$_2$SO$_4$), and concentrated to afford a substantially pure title product (3.13 g, 92%); TLC, $R_f$=0.38 & 0.46, MeOH:CHCl$_3$:AcOH (5:95:1); HPLC, $t_R$=6.20 & 6.25, Col A, H$_2$O:CH$_3$CN:THF:TFA (55:35:15:0.1), FR=3.0.

d.
3(RS)-[4-[(4-Chlorophenyl)sulfonylaminocarbonyl]-phenylcarbonyl]-L-valyl-N-[3-(1,1,1-trifluoro-4-methyl-2-oxopentyl)]-L-prolinamide (Formula Ib, $R^1$=CH(CH$_3$)CH$_3$, $R^2$=CH(CH$_3$)CH$_3$, $R^3$=4-[(4-Cl$\phi$)S(O$_2$)NHCO]$\phi$, $R^4$=H, A=CO, n=1)

To a stirred solution of Dess-Martin periodinane (636 g, 1.50 mol) in CH$_2$Cl$_2$ (5 liter) was added product prepared using the method of Example 121c (351 g, 0.50 mol) in THF (500 ml), and the resulting suspension was diluted with CH$_2$Cl$_2$ (2 liter), followed by the addition of TFA (171 g, 1.50 mol). After the reaction mixture had been stirred overnight at room temperature, the CH$_2$Cl$_2$ was removed under vacuum, the residue was diluted with EtOAc and treated with a 1:1 mixture of satd aq NaHCO$_3$ and satd aq Na$_2$S$_2$O$_3$. When all the solid had dissolved, the aq layer was separated and the EtOAc layer was washed (a mixture of satd aq NaHCO$_3$:satd aq Na$_2$SO$_3$ (1:1), satd aq NaHCO$_3$, brine), dried (Na$_2$SO$_4$) and concentrated under vacuum. The residue was dissolved in MeOH (1.5 liter) and treated with 1N HCl (1.5 liter), and the MeOH was removed under vacuum. The aq suspension remaining was extracted with CH$_2$Cl$_2$, and the combined CH$_2$Cl$_2$ extracts washed (brine), dried (Na$_2$SO$_4$), and concentrated under vacuum to afford, after purification by flash chromatography (gradient, Et$_2$O to Et$_2$O:MeOH (95:5)) and acidification of the chromatographed product with MeOH 1N HCl as described above, the title product (37%); HPLC, $t_R$=6.68 & 9.27, Col B, H$_2$O:CH$_3$CN:THF:TFA (55:35:15:0.1), FR=2.0.

Analysis calculated for: C$_{30}$H$_{34}$Cl$_1$F$_3$N$_4$O$_7$S: C, 52.44; H, 4.99; N, 8.15. Found: C, 52.31; H, 5.20; N, 8.20.

EXAMPLE 122

3(RS)-N$^2$,N$^6$-Di(phenylmethoxycarbonyl)-L-lysyl-L-valyl-N-[3-(1,1,1-trifluoro-4-methyl-2-oxopentyl)]-L-prolinamide (Formula Ic, $R^1$=CH(CH$_3$)CH$_3$, $R^2$=CH(CH$_3$)CH$_3$, $R^3$=$\phi$CH$_2$, $R^4$=H, $R^5$=$\phi$CH$_2$OCONH(CH$_2$)$_4$, $R^6$=H, A=OCO, n=1)

Using the method of Example 54b, the product of Example 28a was oxidized to afford, after purification by flash chromatography (hexane:Et$_2$O (1:1), then Et$_2$O, then Et$_2$O:EtOAc (3:1)), the title product (56%); HPLC, $t_R$=4.19 & 6.02, Col A, CH$_3$CN:H$_2$O (60:40), FR=1.5.

Analysis calculated for: C$_{38}$H$_{50}$F$_3$N$_5$O$_8$.0.5H$_2$O: C, 59.21; H, 6.67; N, 9.03. Found: C, 58.93; H, 6.62; N, 8.75.

EXAMPLE 123

3(RS)-[1,4-Dioxo-4-(phenylsulfonylamino)butyl]-L-leucyl-L-valyl-N-[3-(1,1,1-trifluoro-4-methyl-2-oxopentyl)]-L-prolinamide (Formula Ic, $R^1$=CH(CH$_3$)CH$_3$, $R^2$=CH(CH$_3$)CH$_3$, $R^3$=$\phi$S(O$_2$)NHCO(CH$_2$)$_2$, $R^4$=H, $R^5$=(CH$_2$)$_3$CH$_3$, $R^6$=H, A=CO, n=1)

A solution of the product of Example 24 (0.5 g, 0.87 mmol), benzenesulfonamide (0.14 g, 0.87 mmol), DMAP (0.11 g, 0.87 mmol) and DCC (0.18 g, 0.87 mmol) in CH$_2$Cl$_2$ (20 ml) was stirred for four days at room temperature. The reaction mixture was filtered and concentrated under vacuum to give a crude product. The product was purified by flash chromatography on Baker pH 5.0 silica gel (gradient, CHCl$_3$ to MeOH:CHCl$_3$ (2:98) to MeOH:CHCl$_3$ (5:95)) to give the title product (0.37 g); HPLC, $t_R$=3.84 & 5.03, Col A, H$_2$O:CH$_3$CN (65:35), FR=1.0.

Analysis calculated for: C$_{32}$H$_{46}$F$_3$N$_5$O$_8$S: C, 52.23; H, 6.57; N, 9.52. Found: C, 51.94; H, 6.29; N, 9.37.

EXAMPLE 124

3(RS)-[4-(Methylsulfonylamino)-1,4-dioxobutyl]-L-leucyl-L-valyl-N-[3-(1,1,1-trifluoro-4-methyl-2-oxopentyl)]-L-prolinamide (Formula Ic, $R^1$=CH(CH$_3$)CH$_3$, $R^2$=CH(CH$_3$)CH$_3$, $R^3$=CH$_3$S(O$_2$)NHCO(CH$_2$)$_2$, $R^4$=H, $R^5$=(CH$_2$)$_3$CH$_3$, $R^6$=H, A=CO, n=1)

A solution of the product of Example 24 (0.5 g, 0.87 mmol), methanesulfonamide (0.082 g, 0.87 mmol), DMAP (0.11 g, 0.87 mmol) and DCC (0.18 g, 0.87 mmol) in CH$_2$Cl$_2$ (20 ml) was stirred for four days at room temperature. The reaction was filtered and concentrated under vacuum to give a crude product which was partially purified by flash chromatography on Baker pH 5.5 silica gel (gradient, CHCl$_3$, MeOH:CHCl$_3$ (1:99) to (2.5:97.5)). The partially purified product was partitioned between EtOAc and a mixture of aqueous 1N HCl and brine. The organic phase was dried (Na$_2$SO$_4$), filtered, and concentrated to give the title product (0.28 g); HPLC, $t_R$=5.99 & 8.95, Col A, H$_2$O: CH$_3$CN (65:35), FR=1.0.

Analysis calculated for: C$_{27}$H$_{44}$F$_3$N$_5$O$_8$S: C, 49.46; H, 6.76; N, 10.68. Found: C, 49.07; H, 6.79; N, 10.43.

EXAMPLE 125

3(RS)-N²-[1,4-Dioxo-4-(phenylsulfonylamino)butyl]-N⁶-phenylmethoxycarbonyl-L-lysyl-L-valyl-N-[3-(1,1,1-trifluoro-4-methyl-2-oxopentyl)]-L-prolinamide (Formula Ic, $R^1$=CH(CH$_3$)CH$_3$, $R^2$=CH(CH$_3$)CH$_3$, $R^3$=$\phi$S(O$_2$)NHCO(CH$_2$)$_2$, $R^4$=H, $R^5$=$\phi$CH$_2$OCONH(CH$_2$)$_4$, $R^6$=H, A=CO, n=1)

A solution of the product of Example 27 (493 mg, 0.670 mmol), benzenesulfonamide (117 mg, 0.745 mmol), DMAP (91 mg, 0.745 mmol), and DCC (153 mg, 0.745 mmol) in CH$_2$Cl$_2$ (20 ml) was stirred at room temperature for 24 hr. The solution was diluted with EtOAc, washed (water), dried (MgSO$_4$), filtered, and concentrated under vacuum. The crude product was purified by flash chromatography on Baker pH 5.5 silica gel (CH$_3$OH:CHCl$_3$ (2.5:97.5)) to afford the title product (243 mg) as a white powder; TLC, $R_f$=0.50, CH$_3$OH:CHCl$_3$:AcOH (5:94:1).

Analysis calculated for: C$_{40}$H$_{53}$F$_3$N$_6$O$_{10}$S.0.75H$_2$O: C, 54.56; H, 6.24; N, 9.54. Found: C, 54.52; H, 6.23; N, 9.48.

EXAMPLE 126

3(RS)-[1,4-Dioxo-4-[(tricyclo[3.3.1.1³,⁷]dec-1-yl)sulfonylamino]butyl]-L-leucyl-L-valyl-N-[3-(1,1,1-trifluoro-4-methyl-2-oxopentyl)]-L-prolinamide (Formula Ic $R^1$=CH(CH$_3$)CH$_3$, $R^2$=CH(CH$_3$)CH$_3$, $R^3$=(1-adamantyl-S(O$_2$)NHCO(CH$_2$)$_2$, $R^4$=H, $R^5$=(CH$_2$)$_3$CH$_3$, $R^6$=H, A=CO, n=1)

a. 1-Adamantanesulfinamide

To the product of Example 82a (10.0g, 45.7 mmol) was slowly added conc ammonium hydroxide (300 ml) and the mixture was heated to reflux for three hr. After distillation of the ammonium hydroxide, the residue was taken up in water and extracted with Et$_2$O. The Et$_2$O layer was washed (brine), dried (Na$_2$SO$_4$), filtered, and concentrated under vacuum. The crude product was purified by suction chromatography on silica gel (Et$_2$O to EtOAc) to give the product (4.2g) as a white solid; m.p.139°–141° (Lit. 141°–142°).

b. 1-Adamantanesulfonamide

To a solution of the product of Example 126a (4.0 g, 20.0 mmol) in acetone (150 ml) at reflux was added a satd acetone solution of KMnO$_4$ until a faint violet color persisted. The solution was cooled, filtered through Celite® and concentrated under vacuum to give the product (3.2g) as a solid; m.p.=191°–193° (Lit. 197°–198°); TLC, $R_f$=0.80, EtOAc.

c. 3(RS)-[1,4-Dioxo-4-[(tricyclo[3.3.1.1³,⁷]dec-1-yl)sulfonylamino]butyl]-L-leucyl-L-valyl-N-[3-(1,1,1-trifluoro-4-methyl-2-oxopentyl)]-L-prolinamide (Formula Ic, $R^1$=CH(CH$_3$)CH$_3$, $R^2$=CH(CH$_3$)CH$_3$, $R^3$=(1-adamantyl)S(O$_2$)NHCO(CH$_2$)$_2$, $R^4$=H, $R^5$=(CH$_2$)$_3$CH$_3$, $R^6$=H, A=CO, n=1)

A solution of the product of Example 24 (300 mg, 0.51 mmol), DMAP (62 mg, 0.51 mmol), WSCDI (99 mg, 0.51 mmol) and the product of Example 126b (110 mg, 0.51 mmol) in CH$_2$Cl$_2$ (30 ml) was stirred at room temperature for 16 hr. The CH$_2$Cl$_2$ solution was washed (1N HCl, brine), dried (MgSO$_4$), filtered, and concentrated under vacuum. The crude product was purified by preparative TLC (MeOH:CHCl$_3$ (1:9)) to give the title product as a solid; TLC, $R_f$=0.56, MeOH:CHCl$_3$ (5:95); HPLC, $t_R$=4.23 & 7.05, Col A, H$_2$O:CH$_3$CN (1:1), FR=2.0.

Analysis calculated for: C$_{36}$H$_{56}$F$_3$N$_5$O$_8$S.1.2H$_2$O: C, 54.22; H, 7.38; N, 7.78. Found: C, 54.28; H, 7.84; N, 7.71.

EXAMPLE 127

3(RS)-[4-(Phenylcarbonylaminosulfonyl)phenyl]carbonyl-L-valyl-N-[3-(1,1,1-trifluor-4-methyl-2-oxopentyl)]-L-prolinamide (Formula Ib, $R^1$=CH(CH$_3$)CH$_3$, $R^2$=CH(CH$_3$)CH$_3$, $R^3$=4-[$\phi$CONHS(O$_2$)]$\phi$—, $R^4$=H, A=CO n=1)

a. N-(4-Methylphenylsulfonyl)benzamide p-Toluenesulfonyl isocyanate (1.00g, 5.07 mmol) was added to a reaction vessel containing AlCl$_3$ (1.69 g, 12.68 mmol) and benzene (35 ml). The reaction mixture was stirred under N$_2$ and at room temperature for 3.5 hours before it was poured into crushed ice (100 ml) containing conc HCL (25 ml). The resulting mixture was stirred for 10 min and partitioned with ether (100 ml). After the aqueous layer was separated, the remaining organic layer was washed with H$_2$O (2×50 ml) and brine (1×50 ml), dried (Na$_2$SO$_4$) and concentrated in vacuo to give the crude product (1.40 g). Purification by ether trituration (200 ml) afforded 1.12 g (80%) of the product; TLC, $R_f$=0.68, CH$_2$Cl$_2$:MeOH:HOAc (94.5:5:0.5).

b. 4-(Phenylcarbonylaminosulfonyl)benzoic acid

Potassium permanganate (1.67g, 10.56 mmol) was added in four equal portions to a preheated reaction vessel (85°) containing the product of Example 127a, (0.97 g, 3.52 mmol) and 0.25M MgSO$_4$ (70 ml). The reaction was stirred at 85° for 2 hours. The hot reaction mixture was filtered through diatomaceous earth and acidified to pH 4.0 with 20% H$_2$SO$_4$. The product, which precipitated out of solution as a white powder, was filtered, washed with cold H$_2$O (100 ml) and dried under high vacuum overnight to afford 1.00g (93%); TLC, $R_f$=0.34, CH$_2$Cl$_2$:MeOH:HOAc (94.5; 5:0.5).

c. 2(RS),3(SR)-[4-(Phenylcarbonylaminosulfonyl)phenyl]carbonyl-L-valyl-N-[3-(1,1,1-trifluoro-2-hydroxy-4-methylpentyl)]-L-prolinamide (Formula VIIb, $R^1$=CH(CH$_3$)CH$_3$, $R^2$=CH(CH$_3$)CH$_3$, $R^3$=4-[$\phi$CONHS(O$_2$)]$\phi$—, $R^4$=H, A=CO, n=1)

WSCDI (0.47 g, 2.45 mmol) was added to a reaction vessel containing the product of Example 127b (0.62 g, 2.04 mmol), the product of Example 5d (0.75 g, 2.04 mmol), HOBT (0.33 g, 2.45 mmol) and dry THF:DMF (8:1, 40 ml). The reaction was stirred overnight under N$_2$ and at room temperature before it was concentrated in vacuo and the resulting syrup was redissolved in CH$_2$Cl$_2$. The organic phase was washed with 1N HCl (2×50 ml) and brine (1×50ml), dried (Na$_2$SO$_4$) and concentrated in vacuo to give the crude product (1.38 g). The crude product was purified by flash chromatography on acidic silica gel, eluting with MeOH:CH$_2$Cl$_2$ (5:95) to give 1.17 g (87.31%) of the product; TLC, $R_f$=0.21–0.32, CH$_2$Cl$_2$:MeOH:HOAc (94.5:5:0.5).

d. 3(RS)-[4-(Phenylcarbonylaminosulfonyl)phenyl]carbonyl-L-valyl-N-[3-(1,1,1-trifluor-4-methyl-2-oxopentyl)]-L-prolinamide (Formula Ib, $R^1$=CH(CH$_3$)CH$_3$, $R^2$=CH(CH$_3$)CH$_3$, $R^3$=4-[$\phi$CONHS(O$_2$)]$\phi$—, $R^4$=H, A=CO, n=1)

TFA (261 mg, 176 ul, 2.29 mmol) was added to a reaction vessel containing the product of Example 127c, (600 mg, 0.92 mmol), Dess-Martin periodinane (972 mg, 2.29 mmol) and CH$_2$Cl$_2$ (30 ml). The reaction mixture was stirred under N$_2$ and at room temperature overnight. The reaction mixture was partitioned between EtOAc (75 ml) and satd NaHCO$_3$ (50 ml) containing Na$_2$S$_2$O$_3$ (2.53 g, 16.03 mmol). After the organic layer was separated, the remaining aqueous layer was acidified to pH 2.0 with 6N HCl. The aqueous layer wa extracted with CH$_2$Cl$_2$. The CH$_2$Cl$_2$ solution was concentrated in vacuo to give the crude product (300 mg), which was purified by dissolving it in ether and reprecipitating the product with hexane to afford 123 mg , (20.5%); TLC, $R_f$=0.30–0.43, CH$_2$Cl$_2$:MeOH: HOAc (94. 5:5:0.5).

Analysis calculated for: C$_{30}$H$_{35}$F$_3$N$_4$O$_7$S.2.5 H$_2$O: C, 51.64; H, 5.78; N, 8.03. Found: C, 51.31; H, 5.14; N, 8.12.

Alternatively, the title product may be prepared by coupling benzoic acid with 3(RS)-[4-aminosulfonylphenyl)carbonyl]-L-valyl-N-[3-(1,1,1-trifluoro-4-methyl-2-oxopentyl)]-L-prolinamide using a similar procedure to the one described in Example 89. The sulfonamide was prepared as follows:

e. 2(RS),3(SR)-[(4-Aminosulfonylphenyl)carbonyl]-L-valyl-N-[3-(2-hydroxy-4-methyl-1,1,1-trifluoropentyl)]-L-prolinamide To a reaction vessel containing 4-carboxybenzene sulfonamide (1.24 g, 6.16 mmol), the product of Example 5d (1.49 g, 4.06 mmol), DMAP (0.60 g, 4.88 mmol) and DMF:CH$_2$Cl$_2$ (1:1, 40 ml) was added WSCDI (0.94 g, 4.88 mmol). The reaction was stirred overnight under N$_2$ and at room temperature before it was washed with 1N HCl (2×50 ml) and brine (1×50 ml), dried (Na$_2$SO$_4$), and concentrated under vacuum to give the crude product (3.11 g). The crude product was purified by flash chromatography on acidic silica gel (MeOH:CH$_2$Cl$_2$ (15:85)) to afford the pure product (0.52 g, 24.8%); TLC, $R_f$=0.49–0.65, CH$_2$Cl$_2$:MeOH:HOAc (89.5:10:0.5).

f. 3(RS)-[(4-Aminosulfonylphenyl)carbonyl]-L-valyl-N-[3-(1,1,1-trifluoro-4-methyl-2-oxopentyl)]-L-prolinamide To a reaction vessel containing the product of Example 127e (250 mg, 0.454 mmol), Dess-Martin periodinane (324 mg, 0.76 mmol) and CH$_2$Cl$_2$ (10 ml) was added TFA (86.7 mg, 0.76 mmol, 58.5 μl). After the reaction was stirred under N$_2$ and at room temperature for 3 hours, it was partitioned between EtOAc (50 ml) and satd NaHCO$_3$ (50 ml) containing Na$_2$S$_2$O$_3$ (841 mg, 5.32 mmol). After the organic phase was separated, the aqueous layer was extrated with EtOAc (2×50 ml). The combined organic phase was washed with brine (2×50 ml), dried (Na$_2$SO$_4$), and concentrated under vacuum to provide a crude product (230 mg). The crude product was purified by flash chromatography (acidic silica gel; MeOH:CH$_2$Cl$_2$ (10:90)) to give pure product (180 mg, 72.3%); TLC, $R_f$=0.60–0.69, MeOH:CH$_2$Cl$_2$ (10:90).

Analysis calculated for: C$_{23}$H$_{31}$F$_3$N$_4$O$_6$S.0.5 H$_2$O: C, 49.54; H, 5.78; N, 10.05. Found: C, 49.53; H, 5.77; N, 9.51.

What is claimed is:

1. A compound of the formula V

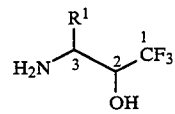

wherein $R^1$ is an alkyl group containing 1 to 5 carbon atoms and the acid-addition salts thereof.

2. A compound as claimed in claim 1 wherein $R^1$ is isopropyl, and the acid addition salts thereof.

* * * * *